US011912765B2

United States Patent
Orwar et al.

(10) Patent No.: US 11,912,765 B2
(45) Date of Patent: Feb. 27, 2024

(54) METHODS FOR EPITOPE SELECTION

(71) Applicant: OBLIQUE THERAPEUTICS AB, Gothenburg (SE)

(72) Inventors: Owe Orwar, Hovås (SE); Carolina Trkulja, Borås (SE)

(73) Assignee: OBLIQUE THERAPEUTICS AB, Gothenburg (SE)

( * ) Notice: Subject to any disclaimer, the term of this patent is extended or adjusted under 35 U.S.C. 154(b) by 280 days.

(21) Appl. No.: 17/488,692

(22) Filed: Sep. 29, 2021

(65) Prior Publication Data

US 2022/0073607 A1    Mar. 10, 2022

Related U.S. Application Data

(62) Division of application No. 15/562,610, filed as application No. PCT/EP2016/057164 on Mar. 31, 2016, now Pat. No. 11,161,901.

(Continued)

(51) Int. Cl.
*C40B 50/06* (2006.01)
*C07K 16/28* (2006.01)
(Continued)

(52) U.S. Cl.
CPC ............ *C07K 16/28* (2013.01); *C07K 14/705* (2013.01); *C07K 16/00* (2013.01);
(Continued)

(58) Field of Classification Search
None
See application file for complete search history.

(56) References Cited

U.S. PATENT DOCUMENTS

| 11,408,883 B2 | 8/2022 | Orwar et al. |
| 2004/0002118 A1 | 1/2004 | Smilansky |

(Continued)

FOREIGN PATENT DOCUMENTS

| EP | 2 174 908 | 4/2010 |
| EP | 2 186 879 | 5/2010 |

(Continued)

OTHER PUBLICATIONS

Wolff, A. et al., "The aminoterminal domain of alpha-tubulin probed by monoclonal antibodies. Recoginition of a rarely exposed epitope by the monoclonal antibody 111 B52 C2", Biology of the Cell, vol. 63, pp. 319-326, 1988.

(Continued)

*Primary Examiner* — Christian C Boesen
(74) *Attorney, Agent, or Firm* — Wenderoth, Lind & Ponack, L.L.P.

(57) ABSTRACT

The present invention relates to certain new methods to select epitopes for antibodies. The present invention also provides a method of generating an antibody (e.g. a functional antibody) to a protein, said method comprising (i) identifying an antigenic epitope in said protein by exposing the protein to limited or restricted proteolysis by contacting the protein with at least one protease to form at least one digested, deconstructed or truncated version of the protein and at least one surface-exposed peptide that is cleaved off from the protein by the action of said protease and generating an antigenic epitope based on said surface-exposed peptide; and (ii) raising an antibody against the antigenic epitope. The present invention also provides antigenic epitopes and antibodies against such epitopes.

35 Claims, 19 Drawing Sheets

Specification includes a Sequence Listing.

Related U.S. Application Data

(60) Provisional application No. 62/283,118, filed on Aug. 21, 2015, provisional application No. 62/140,955, filed on Mar. 31, 2015.

(51) Int. Cl.
   *C40B 30/04* (2006.01)
   *C07K 14/705* (2006.01)
   *C07K 16/00* (2006.01)

(52) U.S. Cl.
   CPC ...... *C12Y 304/21004* (2013.01); *C40B 30/04* (2013.01); *C07K 2317/34* (2013.01); *C07K 2317/76* (2013.01)

(56) References Cited

U.S. PATENT DOCUMENTS

| | | |
|---|---|---|
| 2004/0072251 A1 | 4/2004 | Anderson |
| 2004/0185038 A1 | 9/2004 | Carr et al. |
| 2006/0292639 A1 | 12/2006 | Mansson et al. |
| 2008/0146502 A1 | 6/2008 | Collier et al. |
| 2012/0052592 A9 | 3/2012 | Tsuyoshi et al. |
| 2012/0128646 A1 | 5/2012 | Haskins et al. |
| 2012/0263728 A1 | 10/2012 | Baker |
| 2015/0241450 A1 | 8/2015 | Liu et al. |
| 2015/0309046 A1 | 10/2015 | Blagoev et al. |

FOREIGN PATENT DOCUMENTS

| | | |
|---|---|---|
| JP | 2008-175814 | 7/2008 |
| WO | 92/07083 | 4/1992 |
| WO | 96/29412 | 9/1996 |
| WO | 2005/019266 | 3/2005 |
| WO | 2006/005472 | 1/2006 |
| WO | 2006/047417 | 5/2006 |
| WO | 2006/068619 | 6/2006 |
| WO | 2008/120684 | 10/2008 |
| WO | 2009/136382 | 11/2009 |
| WO | 2014/165271 | 10/2014 |

OTHER PUBLICATIONS

Golizeh, M. et al., "Optimized proteomic analysis of rat liver microsomes using dual enzyme digestion with 2D-LC-MS/MS", J. Proteomics, vol. 82, pp. 166-178, 2013.

Kwon, J. et al., " Systematic cyanobacterial membrane proteome analysis by combining acid hydrolysis and digestive enzymes with nano-liquid chromatography-Fourier transform mass spectrometry", Journal of Chromatography A., vol. 1217, pp. 285-293, 2010.

Shangguan, L. et al., "Investigation of bi-enzmatic reactor based on hybrid monolith with nanoparticles embedded and its proteolytic characteristics", Journal of Chromatography A., vol. 1388, pp. 158-166, 2015.

Brown, F. et al., "Delineation of a neutralizing subregion within the immunodominant epitope (GH loop) of foot-and-mouth disease virus VP1 which does not contain the RGD motif", Vaccine, vol. 18, pp. 50-56, 2000.

International Preliminary Report on Patentability dated Oct. 3, 2017 in International (PCT) Application No. PCT/EP2016/057164.

Jansson et al., "Microfluidic Flow Cell for Sequential Digestion of Immobilized Proteoliposomes", Analytical Chemistry, 84: 5582-5588 (2012).

Freund et al., "Targeting endogenous nuclear antigens by electrotransfer of monoclonal antibodies in living cells", mAbs, 5(4): 518-522 (2013).

Trkulja, Carolina, "Methods for elucidating membrane protein structure and function", Thesis for the Degree of Doctor of Philosophy, Chalmers University of Technology, Sweden (2015).

Hager-Braun et al., "Determination of protein-derived epitopes by mass spectrometry", Expert Rev. Proteomics, 2(5): 745-756 (2005).

Cabral et al., "Biophysical Studies on BEX3, the p75$^{NTR}$-Associated Cell Death Executor, Reveal a High-Order Oligomer with Partially Folded Regions", PLOS ONE, 10(9): 1-23 (2015).

Cassady-Cain et al., "Biophysical Characterization and Activity of Lymphostatin, a Multifunctional Virulence Factor of Attaching and Effacing *Escherichia coli**", J. Biol. Chem., 291(11): 5803-5816 (2016).

El-Kased et al., "A Novel Mass Spectrometric Epitope Mapping Approach Without Immobilization of the Antibody", Journal of Proteomics & Bioinformatics, 4(1): 001-009 (2011).

Hilton et al., "A new structural insight into XPA-DNA interactions", Bioscience Reports, 34(6): 831-840 (2014).

Lassaux et al., "A Structure-Based Strategy for Epitope Discovery in Burkholderia pseudomallei OppA Antigen", Structure, 21: 167-175 (2013).

Myrum et al., "Arc is a flexible modular protein capable of reversible self-oligomerization", Biochem J., 468: 145-158 (2015).

Rajabi et al., "A comparison of the folding characteristics of free and ribosome-tethered polypeptide chains using limited proteolysis and mass spectrometry", The Protein Society, 24: 1282-1291 (2015).

Saxena et al., "Nucleotide-Induced Conformational Changes in *Escherichia coli* DnaA Protein Are Required for Bacterial ORC to Pre-RC Conversion at the Chromosomal Origin", International Journal of Molecular Sciences, 16: 27897-27911 (2015).

Suckau et al., "Molecular epitope identification by limited proteolysis of an immobilized antigen-antibody complex and mass spectrometric peptide mapping", Proc. Natl. Acad. Sci. USA, 87(24): 9848-9852 (1990).

Zhang et al., "Analysis of Monoclonal Antibody Sequence and Post-translational Modifications by Time-controlled Proteolysis and Tandem Mass Spectrometry*" Molecular & Cellular Proteomics, 15(4): 1479-1488 (2016).

Karlsson et al., "Subcellular localization of an ATPase in anammox bacteria using proteomics and immunogold electron microscopy", FEMS Microbiology Letters, 354: 10-18 (2014).

Jansson et al., "Effect of Cholesterol depletion on the pore dilation of TRPV1", Molecular Pain, 9(1): 1-9 (2013).

Trkulja et al., "Epitope-discovery for sequence-targeting antibody therapeutics", Department of Chemical and Biological Engineering, Chalmers University of Technology, Sweden, pp. 1-15 (2015).

Trkulja et al., "Probing Structure and Function of Ion Channels Using Limited Proteolysis and Microfluidics", Journal of the American Chemical Society, 136(42): 14875-14882 (2014).

Trkulja et al., "Probing Structure and Function of Ion Channels Using Limited Proteolysis and Micro fluidics—Supporting Information", Journal of the American Chemical Society: S1-S28 (2014).

Buckinx et al., "Transient Receptor Potential Vanilloid Type I Channel (TRPVI) Immunolocalization in the Murine Enteric Nervous System Is Affected by the Targeted C-terminal Epitope of the Applied Antibody", Journal of Histochemistry and Cytochemistry, 61(6): 421-432 (2013).

International Search Report and Written Opinion of the International Searching Authority, dated Jun. 7, 2016 in corresponding International Application No. PCT/EP2016/057164.

Kiyotaka Hitomi et al., "Immunological Detection of Proteolytically Activated Epidermal-type Transglutaminase (TGase 3) Using Cleavage-site-specific Antibody", Bioscience Biotechnology and Biochemistry, 2003, vol. 67 (11), pp. 2492-2494.

Bin Yu et al., "Protease Cleavage Sites in HIV-1 gp120 Recognized by Antigen Processing Enzymes Are Conserved and Located at Receptor Binding Sites", Journal of Virology, 2010, vol. 84, No. 3, pp. 1513-1526.

Sharon R. Roberts et al., "The major envelope glycoprotein of the extracellular virion of Autographa californica nuclear polyhedrosis virus possesses at least three distinct neutralizing epitopes", Virus Research, 1993, vol. 28, pp. 285-297.

Marie-Pierre Larvor et al., "Peptide/Antibody Recognition: Synthetic Peptides Derived From the *E. coli* Tryptophan Synthase $\beta_2$ Subunit Interact With High Affinity With an Anti-$\beta_2$ Monoclonal Antibody", Molecular Immunology, 1991, vol. 28, No. 4/5, pp. 523-531.

(56) References Cited

OTHER PUBLICATIONS

Michel Koenig et al., "Detailed Analysis of the Repeat Domain of Dystrophin Reveals Four Potential Hinge Segments That May Confer Flexibility", The Journal of Biological Chemistry, 1990, vol. 265, No. 8, pp. 4560-4566.

B. Friguet et al., "Polypeptide-Antibody Binding Mechanism: Conformational Adaptation Investigated by Equilibrium and Kinetic Analysis", Research in Immunology, 1989, vol. 140 (4), pp. 355-376.

Xuemei Han et al., "Mass Spectrometry for Proteomics", Current Opinion in Chemical Biology, 2008, vol. 12, pp. 483-490.

Stefanescu et al., "Mass spectrometric approaches for elucidation of antigen-antibody recognition structures in molecular immunology", Eur. J. Mass Spectrom, 2007, vol. 13, pp. 69-75.

Mazzoni M.R. et al., "Proteolytic Fragmentation for Epitope Mapping", Methods in Molecular Biology, Epitope Mapping Protocols, Human Press, 2009, Reineke U. and M. Schutkowski eds. pp. 77-86.

Langton, B.C. et al. "Structural Features of an Antigen Required for Cellular Interactions and for T Cell Activation in a MHC-Restricted Response", the Journal of Immunology, 1988, vol. 141, No. 2, pp. 447-456.

Yurchenco, P.D. et al., "Monoclonal Antibodies as Probes of Domain Structure of the Spectrin α Subunit", the Journal of Biological Chemistry, 1982, vol. 257, No. 15, pp. 9102-9107.
Hasan et al., "In Silico Molecular Characterization of Cysteine Protease YopT from *Yersinia pestis* by Homology Modeling and Binding Site Identification", Drug Target Insights, 2014, vol. 8, p. 1-9.
Borley et al., "Evaluation and Use of In-Silico Structure-Based Epitope Prediction with Foot-and-Mouth Disease Virus", PLoS One, 2013, vol. 8(5):e61122, p. 1-14.
Guo, Xiaofeng et al., "Confetti: A Multiprotease Map of the HeLa Proteome for Comprehensive Proteomics", Molecular & Cellular Proteomics, 2014, vol. 13, pp. 1573-1584.
Trier, N.H. et al., "Production and characterization of peptide antibodies", Methods, vol. 56, pp. 136-144, 2012.

C

METHODS FOR EPITOPE SELECTION

TECHNICAL FIELD

The present invention relates to certain new methods to select epitopes of target proteins, utilized for, but not limited to, antibody (e.g. functional antibody) generation. The present invention thus relates in some aspects to a method for generating an antibody. Such methods typically comprise identification of an antigenic epitope and raising an antibody to the antigenic epitope. The invention also relates to antigenic epitopes and antibodies which bind such antigenic epitopes.

BACKGROUND

Antibody therapeutics is growing rapidly much due to the clinical success seen with several monoclonal antibody (mAb) therapies including Humira, Avastin, Herceptin, and the promise of e.g. new cholesterol-lowering mAb treatments targeting PCSK9, such as Alirocumab and Evolocumab. However, all antibodies currently on the market, and all in advanced stage clinical development are generally directed towards extracellular targets, and they are generally discovered and developed using screening platforms focusing on affinity or binding strength. Development of intracellularly acting antibodies, and antibodies directed to "difficult targets", i.e. targets where traditional antibody discovery methodology has failed is, however, a daunting challenge, requiring new technological advancements to discover and develop efficient antibodies. For intracellularly acting antibodies, new tools for internalization of antibodies to cells in the right target organs are also needed. Furthermore, current antibody discovery and development platforms generally lack functional, pharmacological, and mechanism-of-action correlates that can predict the workings of a particular antibody in a given biological system, such as in a medical condition.

Today, strategies towards developing and finding successful antibody therapeutics are not limited to full size monoclonal antibodies. Due to advances in protein engineering, a wide variety of engineered antibody fragments have been derived during the two last decades including Fab fragments, ScFv fragments, diabodies, tetrabodies, antibody fragments functionalized with protein conjugates, as well as bispecific fragments binding to two antigens. These new constructs provide a much larger toolbox when trying to develop antibodies and antibody-derived biologics with high specificity and affinity, deep tissue penetration, high stability and low toxicity. However, one of the main hurdles with antibody therapies still remains and that is their general restriction to extracellular targets. Antibodies are too large and too polar to enter through the cell membrane. Additionally, antibodies are generally unstable in the reducing environment of the cytosol. Several techniques have been developed in order to access intracellular targets, including transport of antibodies across the cell membrane with different transport vectors e.g. transfection reagents and protein transduction domains (PTDs), as well as the expression of the antibody directly within the target cell, so called intrabodies. Intrabodies can be constructed to target different cellular compartments by fusing the genetic sequence of the intrabody with intracellular trafficking signals. The need for efficient delivery vectors is nonetheless a crucial step in intrabody therapy since the genetic material encoding the intrabody still needs to be delivered to the target cell.

The production of monoclonal antibodies by the hybridoma technique was first developed in 1975. Briefly, mammals are injected with the antigen of interest, which triggers their immune response. Splenocytes from the animal spleen are then removed and later fused with immortalized myeloma cells. The cells are diluted down to single cells and separated into multi-well plates. Since one cell gives rise to each separate colony, the produced antibodies in a single well will be monoclonal. The next step is to screen all of the different wells for the best candidate for binding to the antigen.

A huge advantage with smaller antibody fragments compared to full size antibodies, is that they can be produced in different expression systems, e.g. *Escherichia coli*, yeast and mammalian cells, and are no longer limited to production with the hybridoma technique. This enables large-scale production at lower cost and many possibilities to genetically modulate antibody properties. Antibody fragments can be displayed on the surface of a filamentous bacteriophage, a so-called phage display, which can be used to create large antibody libraries, which are screened against the desired antigen. The screening procedure evaluates the antibody candidates that bind to the antigen. It is often repeated in several cycles due to unspecific binding in the first cycles. The conditions during the screening cycles can be changed in order to find the best suitable candidates for a certain environment, e.g. more stable antibodies can be selected by using a harsh environment. Another method to select antibodies with very high affinity is to perform the screening with very low concentration of antigen so that only those antibodies capable of binding during such conditions remain. Several companies have developed their own screening technologies, and often have large antibody libraries, see e.g. Regeneron (regeneron.com) or Alligator bioscience (alligatorscience.se).

SUMMARY

In one aspect, the present invention provides a method of generating an antibody to a protein, said method comprising:
  (i) identifying an antigenic epitope in said protein by exposing the protein to limited or restricted proteolysis by contacting the protein with at least one protease to form at least one digested, deconstructed or truncated version of the protein and at least one surface-exposed peptide that is cleaved off from the protein by the action of said protease and generating an antigenic epitope based on said surface-exposed peptide; and
  (ii) raising an antibody against the antigenic epitope.

In another aspect, the present invention provides a method of generating an antibody to a protein, said method comprising:
  (i) exposing the protein to limited or restricted proteolysis by contacting the protein with at least one protease to form at least one digested, deconstructed or truncated version of the protein and at least one surface-exposed peptide that is cleaved off from the protein by the action of said protease; and
  (ii) identifying an antigenic epitope by identifying a surface-exposed epitope among the at least one surface-exposed peptide that is present in a region of the protein that results in a lack of, or significantly altered, biological function of the protein when the peptide is cleaved off or removed from the protein during the limited or restricted proteolysis; or
    selecting at least one target region within the protein based on bioinformatics and/or known data of biological function of the protein and identifying an antigenic epitope by identifying a surface-exposed epitope among the at least one surface-exposed peptide present in said at least one target region; and (iii) raising an antibody against the antigenic epitope.

In another aspect, the present invention provides a method of identifying an antigenic epitope, said method comprising:

(i) exposing a protein to limited or restricted proteolysis by contacting the protein with at least one protease to form at least one digested, deconstructed or truncated version of the protein and at least one surface-exposed peptide that is cleaved off from the protein by the action of said protease; and (ii) identifying an antigenic epitope by identifying a surface-exposed epitope among the at least one surface-exposed peptide that is present in a region of the protein that results in a lack of, or significantly altered, biological function of the protein when the peptide is cleaved off or removed from the protein during the limited or restricted proteolysis; or selecting at least one target region within the protein based on bioinformatics and/or known data of biological function of the protein and identifying an antigenic epitope by identifying a surface-exposed epitope among the at least one surface-exposed peptide present in said at least one target region.

The present invention relates to methods of detecting and identifying amino acid sequences in proteins where said amino acid sequences are well-exposed, and functionally relevant, at least they are well-exposed. These amino acid sequences which we refer to as "hot spots", thus, may be utilized as antigenic epitopes that guides antibody targeting, discovery, and development. Furthermore, these amino acid sequences can be ranked based on their appearance after proteolytic digestion, and based on functional relevance from already known bioinformatic data or from functional/pharmacological testing. Thus, from a list of several amino acid sequences resulting from a proteolytic digestion, the best suited amino acid sequences (based on functional and structural arguments) can be picked for antigenic epitope discovery and development. The proteolytic digestion is performed under limiting conditions, i.e. the activity of the protease or several proteases is very low such that just one or a few surface-exposed peptides are cleaved off from the target protein at a time. The proteases are thus used as druggability probes for antibody binding to a target protein.

In an embodiment, the antibodies are pharmacologically active. In another embodiment, the antibodies are pharmacologically active and developed for therapeutic usage. More specifically, such methods include proteomic tools to reveal hot spot epitopes of target proteins.

In an aspect of the invention, a protein is digested, deconstructed and/or truncated through protease action and all well-exposed amino acid sequences are used for antigenic epitope generation, and antibodies developed based on said antigenic epitopes are tried for potency, efficacy, pharmacological profiling, and other testing as customary in antibody discovery used in the pharmaceutical industry.

In an aspect of the invention, a protein is digested, deconstructed and/or truncated through protease action and in parallel probed by a functional assay on the digested, deconstructed and/or truncated protein to delineate functionally important regions of the protein. The relevant protein is sometimes denoted target protein herein.

In an embodiment, the digestion, deconstruction and/or truncation of the target protein is performed in parallel by a functional assay to delineate functionally important regions of the target protein to guide epitope selection for antibody generation.

In an embodiment, the digestion, deconstruction and/or truncation, and functional assay of digested, deconstructed and/or truncated protein and native target protein are combined with other bioinformatic and otherwise known facts about protein function to delineate functionally important regions of the target protein to guide epitope selection for antibody generation.

In an embodiment, a single protease may be used to digest, deconstruct and/or truncate the target protein. In another embodiment, multiple proteases may be used to digest, deconstruct and/or truncate the target protein, sequentially one at a time or in parallel. Such proteases are exemplified but not limited to Arg-C proteinase, Asp-N endopeptidase, Clostripain, Glutamyl endopeptidase, Lys-C, Lys-N, Trypsin, Chymotrypsin, Proteinase K and Thermolysin. A region that is easily digested by several proteases should be located in an exposed region of the protein and a region that is only digested by a single protease is probably located in a more hidden region. Alternatively, the protease has unique cleaving specificity or/and physicochemical properties or/and structural features such that it can identify surface-exposed peptides on a target protein that other proteases cannot. Thus, the usage of multiple proteases is preferable, and each different protease can yield complementary or unique information about surface-exposed peptides suitability as antigenic epitopes.

The embodiments enable new methodology/technology for rapid and precise development of pharmacologically active antibodies that can be used for pharmacological studies, e.g. they can be used as a tool for detecting biological compounds in e.g. cell or in vitro assays. More importantly, said antibodies may be used to treat a medical condition in humans and animals. The embodiments can be applied to all proteins, soluble or membrane bound, extracellular or intracellular. The embodiments can furthermore be exploited to yield new fundamental understanding of protein function.

The present invention also provides an antibody generated by a method of the present invention.

The present invention also provides an antigenic epitope identified by a method of the present invention.

The present invention also provides an antibody against an antigenic epitope of the present invention.

Other features and advantages of the invention will be apparent from the following detailed description.

BRIEF DESCRIPTION OF THE DRAWINGS

The embodiments, together with further objects and advantages thereof, may best be understood by making reference to the following description taken together with the accompanying drawings, in which.

Figure 1:
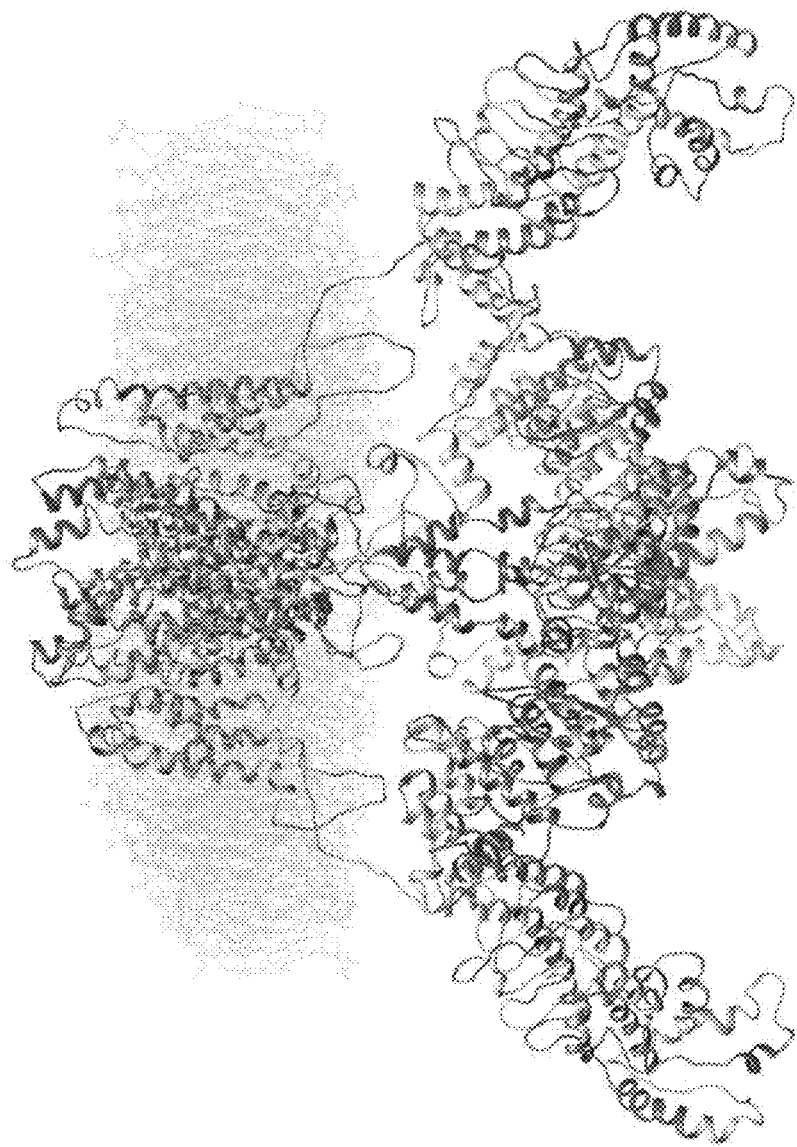
FIG. 1
Figure 1:
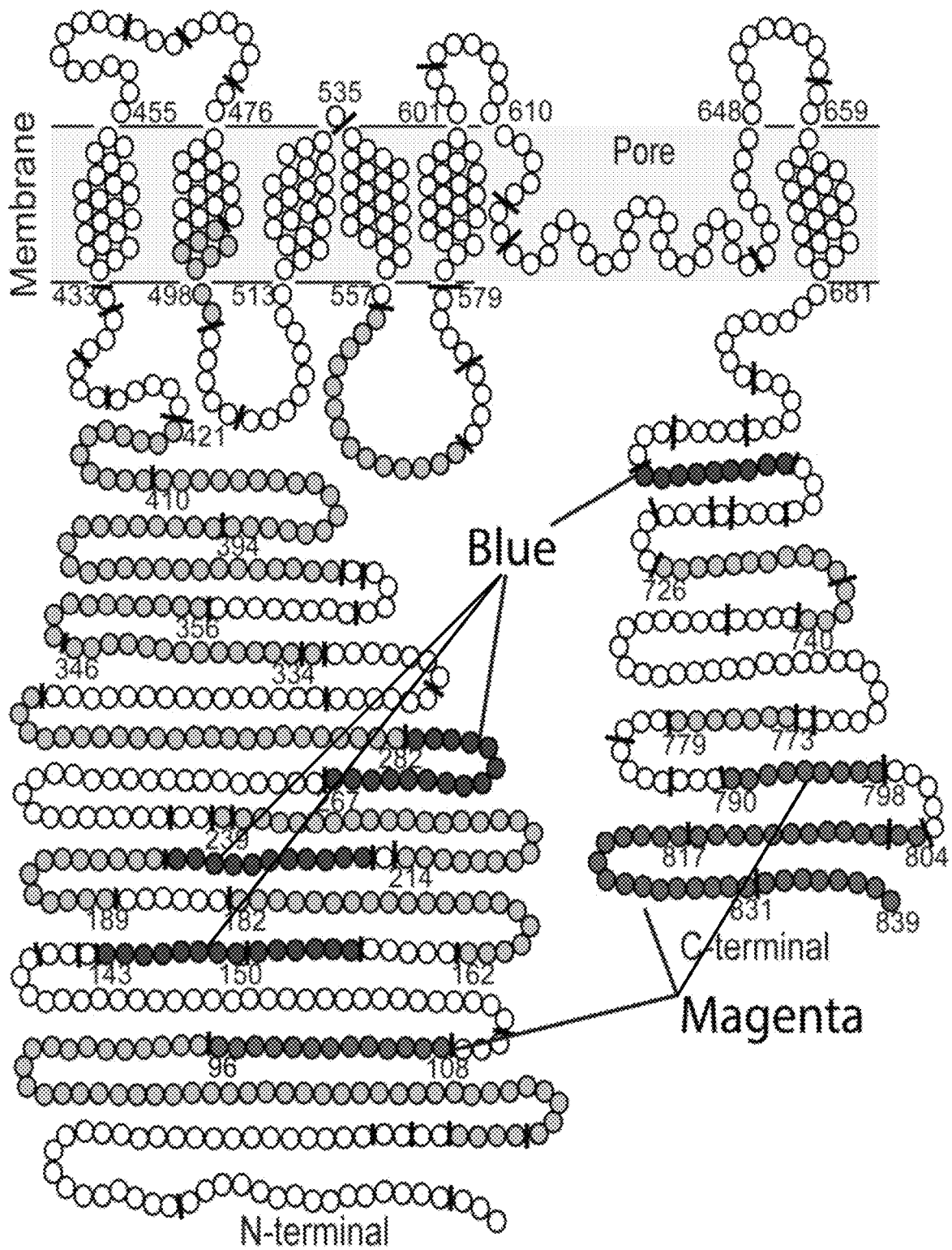
Figure 1:
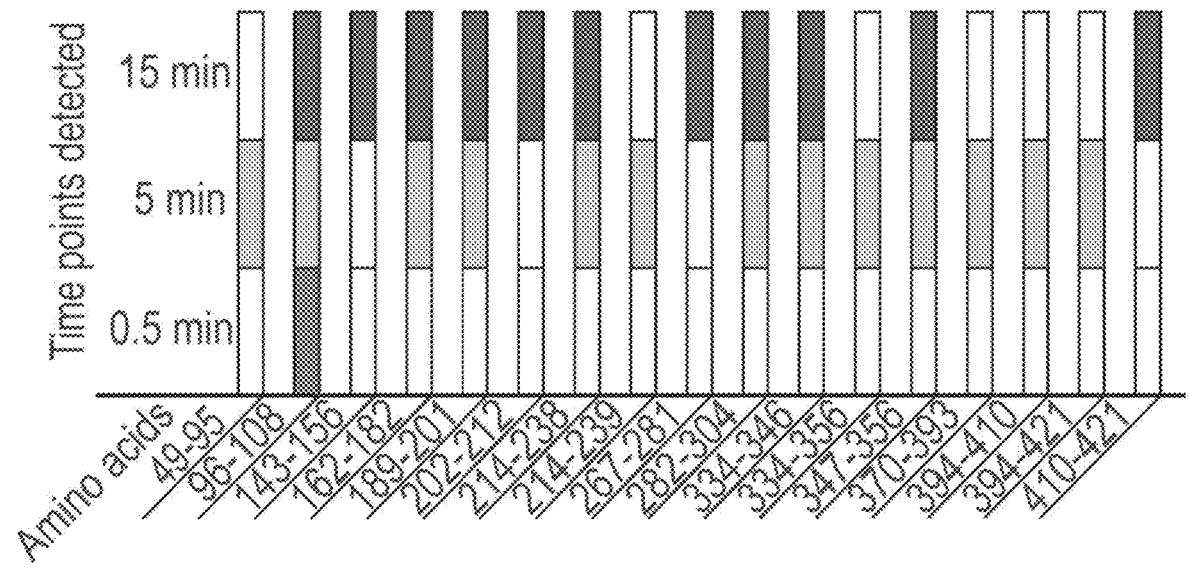
Figure 1:
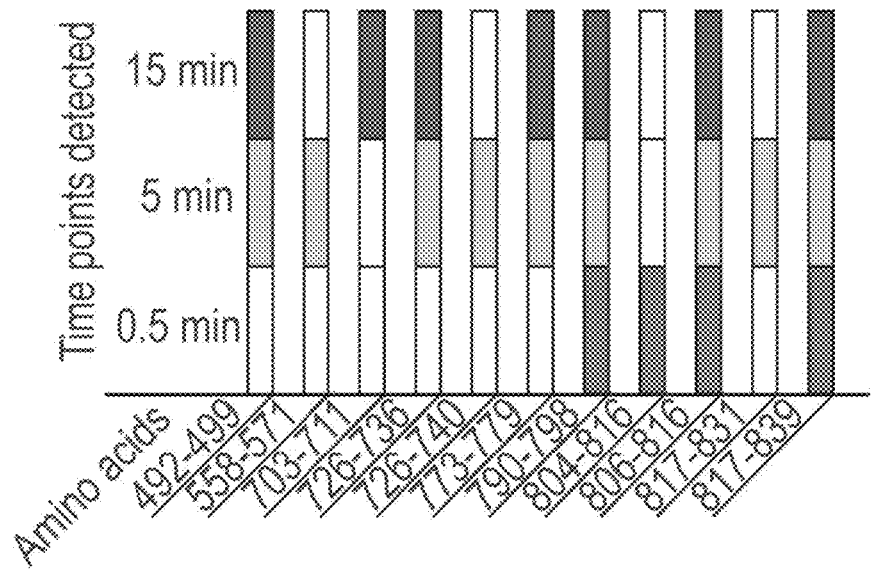

Peptides detected from TRPV1 after limited proteolysis with 5 µg/ml trypsin at room temperature, n=6. A: Location of detected peptides shown in a 3D-model of TRPV1. Peptides were detected after 0.5 min (magenta), 5 min (orange), and 15 min (blue) B: Location of detected peptides shown in a schematic representation of TRPV1. Peptides were detected after 0.5 min (magenta), 5 min (orange), and 15 min (blue). C: Bar plot of detected peptides digested from TRPV1 after limited proteolysis with 5 µg/ml trypsin, showing at which time points they were confirmed.

FIG. 2

Peptides digested from TRPV1 after 5 min exposure to 5 μg/ml, 20 μg/ml or 40 μg/ml trypsin (Tr) and the change in current response after their removal. A-C: Location of digested peptides from TRPV1, showing peptides digested within the flow cell (cyan) and peptides digested within the flow cell followed by a complete digestion overnight (yellow). D: Representative traces of inside-out recordings of TRPV1 when activated with 1 μM capsaicin (Cap), followed by 5 min exposure to either buffer or trypsin and an additional activation with capsaicin. From top to bottom: 5 min exposure to buffer, 5 μg/ml, 20 μg/ml and 40 μg/ml trypsin respectively. Traces have been digitally filtered at 100 Hz for figure presentation purposes only.

FIG. 3

Electrophysiological patch clamp recordings of TRPV1 function showing the current trace time integral for the second activation with capsaicin, calculated as a percentage of the integral for the first activation with capsaicin after treatment with either buffer n=11, or antibody n=6. Data is presented as mean±SEM.

FIG. 4

Location of the antigen determinant (red) for OTV1, peptide aa96-117, visualized in a surface model of hTRPV1. A: Side view of TRPV1 where each monomer is colored in alternating blue and purple. B: Top view of TRPV1 where each monomer is colored in alternating blue and purple.

FIG. 5

Location of the antigen determinant (red) for OTV2, peptide aa785-799, visualized in a surface model of hTRPV1. A: Side view of TRPV1 where two monomers have been omitted for viewing purposes. B: Bottom view of TRPV1 where each monomer is colored in alternating blue and purple.

FIG. 6

Localization of OTV1 (left) and OTV2 (right) in fixed cells with (A) and without (B) the expression of TRPV1. OTV1 and OTV2 were visualized using a goat anti-rabbit Alexa 488 secondary antibody. The intensity values along a line segment (black) crossing a cell is given beneath each image. Different laser settings were used for OTV1 and OTV2 and comparisons between the antibodies shouldn't be made.

FIG. 7

Electrophysiological patch clamp recordings of TRPV1 function after treatment with antibody. A: the current trace time-integral for the second activation with capsaicin, calculated as a percentage of the integral for the first activation with capsaicin, after treatment with either buffer (n=11) or OTV1 (n=6). B: The current trace time-integral for the second activation with capsaicin in the presence of calmodulin (CaM) and OTV2, calculated as a percentage of the integral for the first activation with capsaicin, after treatment with either only calmodulin (n=11) or calmodulin and OTV2. Treatment with OTV2 is separated into measurements within 15 minutes of tip-sonication (n=4) and measurements within 30 minutes of tip-sonication (n=7). Data is presented as mean±SEM.

FIG. 8

A: TRPV1 mediated YO-PRO uptake after electroporation with OTV1 in calcium free PBS. Top: Fluorescence intensity for OTV1 (n=11) and control (n=11). Bottom: Corresponding fluorescence intensity rate for OTV1 and control. B: TRPV1 mediated YO-PRO uptake after electroporation with OTV2 in the presence of 50 μM $Ca^{2+}$. Top: Fluorescence intensity for OTV2 (n=9) and control (n=7). Bottom: Corresponding fluorescence intensity rate for OTV2 (green) and control (red). Data is presented as mean±SEM.

FIG. 9

Validation of internalization of antibodies through electroporation, with fluorescence. Cells were electroporated, fixed, permeabilized and incubated with a goat antirabbit Alexa 488 secondary antibody. Fluorescence intensities were measured with confocal microscopy. Intensities are compared between electroporated and non-electroporated cells subjected to either OTV1 or OTV2, as well as cells only subjected to the secondary antibody. Different laser setting were used between OTV1 and OTV2 and comparisons in intensity values shouldn't be made. Data is presented as mean±SEM.

FIG. 10

Peptides detected from TRPV1 after limited proteolysis with trypsin. Location of detected peptides shown in a 3D-model of TRPV1. Experimental details are given in Example 3. Peptides digested first are shown in black. Peptides digested late are shown in grey.

FIG. 11

Peptides detected from TRPV1 after limited proteolysis with Asp-N. Location of detected peptides shown in a 3D-model of TRPV1. Experimental details are given in Example 3. Peptides digested first are shown in black. Peptides digested late are shown in grey.

FIG. 12

Peptides detected from TRPV1 after limited proteolysis with Chymotrypsin. Location of detected peptides shown in a 3D-model of TRPV1. Experimental details are given in Example 3. Peptides digested first are shown in black. Peptides digested late are shown in grey.

FIG. 13

Peptides detected from TRPV1 after limited proteolysis with pepsin. Location of detected peptides shown in a 3D-model of TRPV1. Experimental details are given in Example 3. Peptides digested first are shown in black. Peptides digested late are shown in grey.

FIG. 14

Peptides detected from TRPV1 after limited proteolysis with Proteinase K. Location of detected peptides shown in a 3D-model of TRPV1. Experimental details are given in Example 3. Peptides digested first are shown in black. Peptides digested late are shown in grey.

DETAILED DESCRIPTION

The foregoing and other aspects of the present invention will now be described in more detail with respect to the description and methodologies provided herein. It should be appreciated that the invention may be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents, and other references mentioned herein are incorporated by reference. The references cited herein are not admitted to be prior art to the claimed invention. In the case of conflict, the present specification, including definitions, will control. In addition, the materials, methods, and examples are illustrative only and are not intended to be limiting.

The terminology used in the description of the invention herein is for the purpose of describing particular embodiments only and is not intended to be limiting of the invention. As used in the description of the embodiments of the invention, the singular forms "a," "an" and "the" are intended to include the plural forms as well, unless the context clearly indicates otherwise. Also, as used herein, "and/or" refers to and encompasses any and all possible combinations of one or more of the associated listed items. Furthermore, the term "about," as used herein when referring to a measurable value such as an amount of a compound, dose, time, temperature, and the like, is meant to encompass variations of 20%, 10%, 5%, 1%, 0.5%, or even 0.1% of the specified amount. When a range is employed (e.g. a range from x to y) it is it meant that the measurable value is a range from about x to about y, or any range therein, such as about x1 to about y1, etc. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Unless otherwise defined, all terms, including technical and scientific terms used in the description, have the same meaning as commonly understood by one of ordinary skill in the art to which this invention belongs.

In one aspect, the present invention provides a method of generating an antibody to a protein, said method comprising:
  (i) identifying an antigenic epitope in said protein by exposing the protein to limited or restricted proteolysis by contacting the protein with at least one protease to form at least one digested, deconstructed or truncated version of the protein and at least one surface-exposed peptide that is cleaved off from the protein by the action of said protease and generating an antigenic epitope based on said surface-exposed peptide; and
  (ii) raising an antibody against the antigenic epitope.

In another aspect, the present invention provides a method of generating an antibody to a protein, said method comprising:
  (i) exposing the protein to limited or restricted proteolysis by contacting the protein with at least one protease to form at least one digested, deconstructed or truncated version of the protein and at least one surface-exposed peptide that is cleaved off from the protein by the action of said protease; and
  (ii) identifying an antigenic epitope by identifying a surface-exposed epitope among the at least one surface-exposed peptide that is present in a region of the protein that results in a lack of, or significantly altered, biological function of the protein when the peptide is cleaved off or removed from the protein during the limited or restricted proteolysis; or
    selecting at least one target region within the protein based on bioinformatics and/or known data of biological function of the protein and identifying an antigenic epitope by identifying a surface-exposed epitope among the at least one surface-exposed peptide present in said at least one target region; and
  (iii) raising an antibody against the antigenic epitope.

Alternatively viewed, the present invention provides a method of generating an antibody to a protein, said method comprising:
  (i) exposing the protein to limited or restricted proteolysis by contacting the protein with at least one protease to form at least one digested, deconstructed or truncated version of the protein and at least one surface exposed peptide that is cleaved off from the protein by the action of said protease; and
  (ii) identifying an antigenic epitope by identifying a surface-exposed peptide that is cleaved off that has an amino acid sequence that is, or that is predicted to be, of functional importance to said protein, and generating an antigenic epitope based on said surface-exposed peptide; and
  (iii) raising an antibody against said antigenic epitope.

In another aspect, the invention provides a method of generating an antibody to a protein, said method comprising:
  (i) identifying a surface-exposed peptide in said protein by exposing the protein to limited or restricted proteolysis by contacting the protein with at least one protease to form at least one digested, deconstructed or truncated version of the protein and at least one peptide that is cleaved off from the protein by the action of said protease; and
  (ii) constructing a linear or conformational antigenic epitope based on the at least one surface-exposed peptide; and
  (iii) raising an antibody against the antigenic epitope.

In another aspect, the invention provides a method of generating an antibody to a protein, said method comprising:
  (i) identifying a surface-exposed peptide in said protein by exposing the protein to limited or restricted proteolysis by contacting the protein with at least one protease to form at least one digested, deconstructed or truncated version of the protein and at least one surface-exposed peptide that is cleaved off from the protein by the action of said protease; and
  (ii) identifying a surface-exposed peptide that when cleaved off or removed from the protein during the limited or restricted proteolysis, results in a lack of, or significantly altered, biological function of said protein; or selecting at least one of the identified surface-exposed peptides of (i) based on correlation of said surface-exposed peptides with bioinformatics and/or known data of biological function of the protein; and
  (iii) constructing a linear or conformational antigenic epitope based on the at least one surface-exposed peptide; and
  (iv) raising an antibody against the antigenic epitope.

In another aspect, the present invention provides a method of generating an antibody to a protein, said method comprising:
  (i) identifying an antigenic epitope in said protein by exposing the protein to limited or restricted proteolysis by contacting the protein with at least one protease to form at least one digested, deconstructed or truncated version of the protein and at least one surface-exposed peptide that is cleaved off from the protein by the action of said protease; and
  (ii) raising an antibody against the antigenic epitope.

A method of generating an antibody in accordance with the present invention may, in another aspect, be alternatively viewed as a method for the production of an antibody that specifically binds to a protein. Exemplary and preferred embodiments of methods of generating an antibody described herein also apply, mutatis mutandis, to methods for the production of an antibody that specifically binds to a protein.

In another aspect, the present invention provides a method of identifying an antigenic epitope, said method comprising:
(i) exposing a protein to limited or restricted proteolysis by contacting the protein with at least one protease to form at least one digested, deconstructed or truncated version of the protein and at least one surface-exposed peptide that is cleaved off from the protein by the action of said protease; and
(ii) identifying an antigenic epitope by identifying a surface-exposed epitope among the at least one surface-exposed peptide that is present in a region of the protein that results in a lack of, or significantly altered, biological function of the protein when the peptide is cleaved off or removed from the protein during the limited or restricted proteolysis; or
selecting at least one target region within the protein based on bioinformatics and/or known data of biological function of the protein and identifying an antigenic epitope by identifying a surface-exposed epitope among the at least one surface-exposed peptide present in said at least one target region.

Optionally, this method further comprises a step of raising an antibody against said antigenic epitope.

Alternatively viewed, the present invention provides a method of identifying an antigenic epitope, said method comprising:
(i) exposing a protein to limited or restricted proteolysis by contacting the protein with at least one protease to form at least one digested, deconstructed or truncated version of the protein and at least one surface-exposed peptide that is cleaved off from the protein by the action of said protease; and
(ii) identifying an antigenic epitope by identifying a surface-exposed peptide that is cleaved off that has an amino acid sequence that is, or that is predicted to be, of functional importance to said protein, and generating an antigenic epitope based on said surface-exposed peptide.

Optionally, this method further comprises a step of raising an antibody against said antigenic epitope.

Detailed knowledge about surface-exposed functionally active epitopes within a protein could aid the development of efficient antibodies and decrease the need for elaborate screening procedures by lowering the amount of antibody candidates. A possible method to evaluate surface topology of a protein is to restrict the activity of a protease to digest only the most flexible and surface-exposed parts of the protein, by performing limited and controlled proteolysis. The idea is to slow down the kinetics of protease activity so much that peptides are cleaved off one at the time, or at most a few at the time. The cleaved off peptides can then be ranked based on order of appearance after a protease challenge. The peptides that are cleaved off the protein first are well exposed by the protein, and can be easily accessed by the protease. We give these peptides a high rank, and we hypothesize that peptides easily cleaved off by a protease are also easily recognized by an antibody. The peptides that are cleaved off late we give a low rank, and all peptides in between are given from high to low scores based on appearance in time after a protease challenge. Thus, the method is amino acid sequence based, and since we know the sequence we know specifically where the antibody will bind to said target protein. In a second step, as we know the specific amino acid sequences that are targeted in a protein, we can investigate from published data or other known bioinformatic data or from pharmacological studies of truncated proteins the functional significance of said amino acid sequence. If the amino acid sequence coincides or touches or overlaps with a known amino acid sequence having functional importance, eg binding site, modulatory site, structurally important site, channel region etcetera, then said peptide is given a high score and judged a good candidate for antigenic epitope and subsequent antibody development. This can be achieved, specifically, by controlling the activity of a protease using e.g. low temperatures, low concentrations and/or short digestion times. When limited proteolysis have been performed on proteins with known structure, mainly three structural determinants have been recognized as having impact on where the proteolytic activity occurs. These include flexibility, surface exposure and the number of local interactions. In order for the peptide chain to enter the active site within the protease, flexibility and the ability of the protein to locally unfold is required. Surface exposure renders a cleavage site more likely for proteolysis, due to the fact that regions at the surface tend to more easily unfold as well as impose less steric hindrance. The amount of local interactions in the term of hydrogen bonds and disulphide bridges is also important. Less local interactions favor proteolysis. All three of these structural determinants are usually correlated within the protein. Hence, limited proteolysis will mainly cleave surface exposed regions given that the protein chain can unfold locally. It has been used as a method to determine surface exposed regions in proteins with unknown detailed structure.

The lipid-based protein immobilization (LPI) technology enables flexible chemistry to be performed on membrane proteins. By deriving proteoliposomes from cells and immobilize them within the flow cell, a stationary phase of membrane proteins is created, which can be subjected to several rounds of solutions and different types of chemical modulations, e.g. by enzymes. A sequential tryptic digestion protocol for proteomic characterization has been developed, where the peptides resulting from stepwise enzymatic digestion of the proteoliposomes are analyzed with liquid chromatography with tandem mass spectrometry (LC-MS/MS) [1-3].

In some embodiments of methods of the present invention, the protein is a protein (e.g. a membrane protein) that is present in (e.g. in the lipid bilayer of) a proteoliposome (e.g. in a proteoliposome derived from cells for example human cells). Accordingly, in some embodiments, limited proteolysis is performed on proteoliposomes. Proteoliposomes are lipid vesicles comprising proteins. Proteoliposomes can be reconstituted from purified membrane proteins and lipids or can be directly derived from the cell membrane (e.g. through blebbing) or through lysis of the cell. Preferably, proteoliposomes are derived from (prepared from) cell membranes of lysed cells. Proteoliposomes may be obtained from any cell type of interest. A convenient cell type is Chinese hamster ovary (CHO) cells.

Methods of preparing proteoliposomes are known in the art and any of these may be used (e.g. the method described in Jansson et al. *Anal. Chem.*, 2012, 84:5582-5588). An exemplary and preferred method for preparing proteoliposomes is described in the Examples herein. Typically, proteoliposomes having a diameter of about 50 nm to about 150 nm are preferred.

Using proteoliposomes derived from (prepared from) cell membranes of lysed cells is preferred as proteoliposomes prepared in such a manner (e.g. using a method referred to in the Examples) may present intracellular portions (or domains) of membrane proteins on the exterior of the proteoliposome, thus making available for proteolytic cleavage (and thus antigenic epitope identification) some parts of the protein that would be otherwise inaccessible to a protease.

In one aspect, we have developed a targeted antibody technology by utilizing the LPI microfluidic platform [1, 4] to generate potential epitope candidates. This is a mechanism-, rather than screening-, based methodology. Briefly, the LPI technology, enables flexible chemistry, such as limited proteolysis, to be performed on membrane proteins. By deriving proteoliposomes from cells and immobilize them within the flow cell, a stationary phase of membrane proteins is created. A sequential digestion protocol for proteomic characterization have been developed, where the peptides resulting from stepwise enzymatic digestion of the proteoliposomes are analyzed with LC-MS/MS. Such peptides, generated from a kinetically controlled digestion within the LPI flow cell, elucidates exposed and accessible regions within the target protein, regions that have the potential of being accessible to antibody binding. These potential epitopes are further correlated against known functional data, in order to find epitopes that will yield antibodies with both excellent binding characteristics and biological efficacy. Finally, the chosen epitopes/peptides may be used to immunize a host animal in order to produce antibodies. It should be mentioned that other methods and techniques to perform limited proteolytic digestion are known in the art, and might be used eg for soluable proteins.

In some embodiments of the present invention, the protein (e.g. a membrane protein) is immobilized (e.g. on a solid support) prior to limited or restricted proteolysis to create a stationary phase of the protein. Thus, in some embodiments the protein is surface-bound.

In some embodiments, the protein (e.g. membrane protein) is present in (or is presented on) a proteoliposome (e.g. a proteoliposome derived from cells) and said proteoliposome is immobilized (e.g. on a solid support) prior to limited or restricted proteolysis to create a stationary phase of the protein.

In some embodiments of methods of the present invention, the protein is a membrane protein that is present in a proteoliposome derived from cells, wherein said proteoliposome is immobilized in a flow cell to create a stationary phase of membrane proteins. Suitable flow cells are known in the art, for example, the flow cell described by Jansson et al. (*Anal. Chem.*, 2012, 84:5582-5588).

In some embodiments, the protein (e.g. membrane protein) is present in (or is presented on) a proteoliposome (e.g. a proteoliposome derived from cells) and said proteoliposome is in a suspension (e.g. suspended in a solution).

In some embodiments, said protein is in (or presented on) a protein-containing lipid vesicle that is surface-bound or in a suspension (e.g. suspended in a solution).

In some embodiments, said protein may be part of, or presented on, any appropriate entity such that its functional or natural conformation is preserved, e.g. part of a lipid bilayer or membrane or on a scaffold or particle.

In some embodiments, said protein is in (or presented on) a particle, such as a nanoparticle, or any other colloidal particle that is surface-bound or in a suspension (e.g. suspended in a solution).

In some embodiments, said protein is in (or presented on) a scaffold or other chemical entity such as a caging compound, that is surface-bound or in a suspension (e.g. suspended in a solution).

In some embodiments, said protein is in (or is presented on) an intact cell (biological cell e.g. human cell) that is surface-bound or in a suspension (e.g. suspended in a solution).

"In" in the context proteins in proteoliposomes, protein containing vesicles or intact cells includes proteins that extend to (and thus are exposed to) the exterior of the proteoliposome, protein containing lipid vesicle or cell.

In some embodiments, said protein is in a solution. The solution may be a solution of purified protein or may contain a mixture of proteins.

In some embodiments, cells (e.g. CHO cells) overexpress the protein, for example via a regulatable (e.g. Tetracycline regulatable) expression system. In some embodiments, proteoliposomes derived from such cells are used.

We examined peptides generated from limited proteolysis of the transient receptor potential vanilloid 1 (TRPV1) ion channel with the purpose of finding potential epitopes for development of biologically active antibodies that have the capability of modulating the function of this ion channel. TRPV1 was subjected to limited proteolysis with two different proteases and the digested peptides were correlated with functional data. We have, using this information, developed two polyclonal antibodies, OTV1 and OTV2, acting on the intracellular side of the human TRPV1 (hTRPV1) ion channel. Both antibodies are pharmacologically active and their targeted epitope regions were chosen based on their ease of digestion (or surface exposure (highly ranked peptides after limited proteolysis)) as well as functional importance. OTV1 displays strong inhibitory action on the protein when stimulated with the agonist capsaicin. OTV2 interferes with calmodulin/$Ca^{2+}$ dependent desensitization of TRPV1, which is a process that is triggered by calcium influx through TRPV1. The efficacy of OTV1 and OTV2 was studied both with inside-out patch clamp, where the intracellular side of TRPV1 could be exposed to antibody solution and with a TRPV1-mediated fluorescence uptake assay after the antibodies were electroporated inside living cells.

Methods that use the LPI flow cell in combination with an open-volume microfluidic flow cell for fast solution exchange suitable for patch clamp experiments has previously been described. The beauty of this is that cell membranes can be turned inside out, and intracellular domains of an ion channel can be interrogated directly. In this approach one can obtain correlated structural and functional data using limited and controlled proteolysis. TRPV1 is a cation channel, which is expressed in nociceptive primary sensory neurons. A detailed crystal structure is not available for the full-length protein, but the ankyrin repeat domain (ARD) of the N-terminus has successfully been crystallized for rat TRPV1. Peptides digested at short time scales when performing limited proteolysis on TRPV1 has been compared to known functionally active regions. A third of the detected peptides contained residues that have been proposed to be functionally important.

A screening of TRPV1 surface topology as described in the survey of the field was performed by immobilizing proteoliposomes containing TRPV1 within the flow cell and further expose them to limited trypsin proteolysis [1, 4]. The activity of trypsin was controlled by using different digestion times at room temperature. A sequential protocol was used with cumulative incubation times and the digested peptides were detected with LC-MS/MS. An increasing number of peptides were detected with time, highlighting regions of the proteins that were accessible and easily digested, as well more rigid regions. This is illustrated in FIG. 1. Several of the regions that were observed with LC-MS/MS as cleaved-off peptides after limited proteolysis of TRPV1 in the LPI flow cell correlate with known interaction sites for calmodulin, ATP and PIP2.

Figure 2:
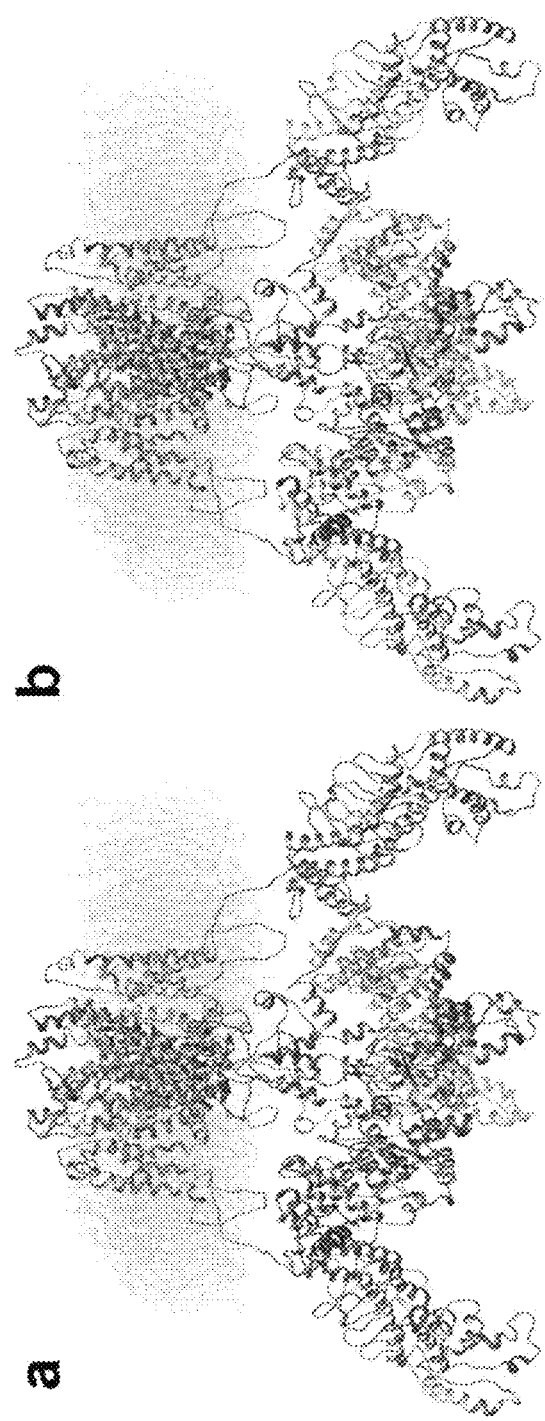
Figure 2:
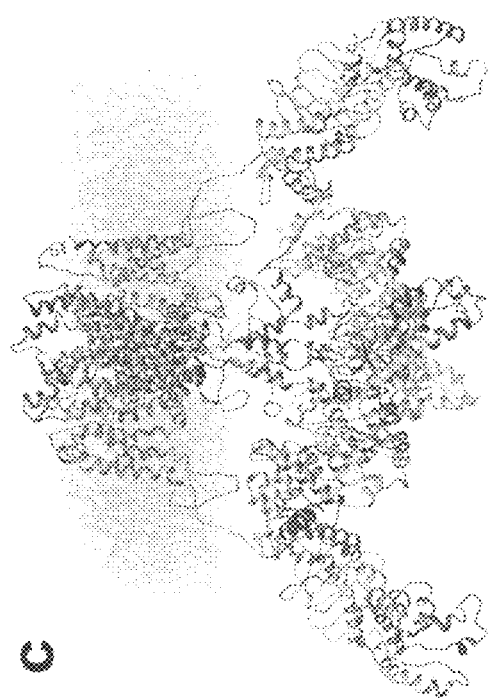
Figure 2:
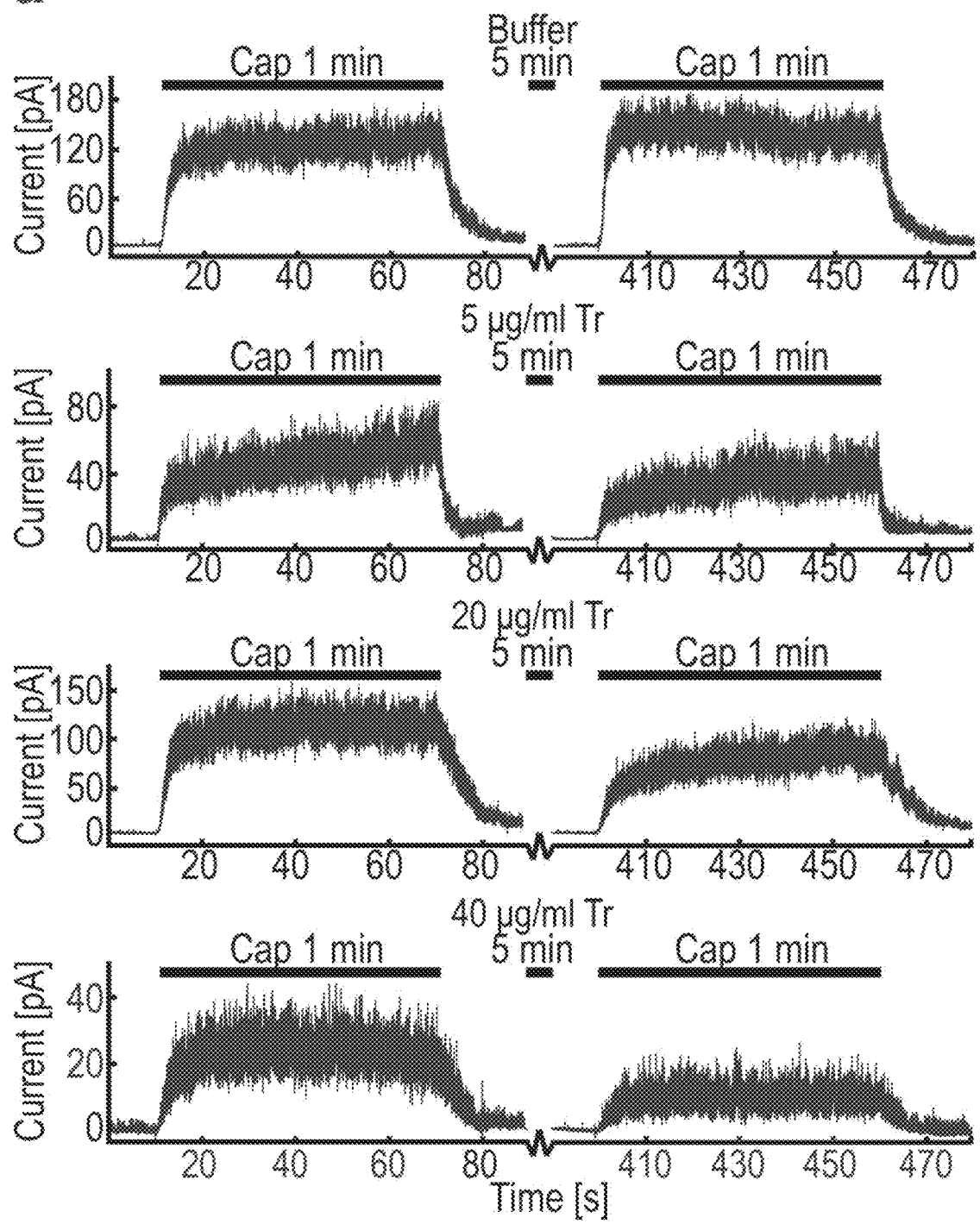

We have also tested the functionality of TRPV1 after removal of different structural segments with tryptic digestion [4]. The activity of the TRPV1 ion channel was tested with inside-out patch-clamp recordings and flow cell digestions followed by proteomic analysis evaluated the structural effects of chemical truncation. We have used the inside-out patch-clamp recording configuration, allowing the intracellular part of TRPV1 to be exposed to trypsin and determined a decrease in current response with increasing trypsin concentration (FIG. 2).

We demonstrate that the ion channel TRPV1 can be exposed to limited and controlled trypsin proteolysis in two different microfluidic flow cells under identical experimental conditions. In one instance, patch-clamp recording was performed for pharmacological studies, which obtained information on channel function dynamics in an open-volume microfluidic device. This design allows the patch-clamp pipette and cell patch to gain access to the superfusion channels. In another instance, a closed-volume equivalent flow cell was used to digest off peptides from the ion channel without causing dilution of the sample. The cleaved-off peptides were identified with LC-MS/MS. The data from the two experiments were then compared and the structure-function relationship could be evaluated. Using this methodological approach we have identified highly flexible regions of TRPV1 as well as key regions that affect functional channel properties during activation with its agonist capsaicin.

This type of methodology can also be used for other proteins (i.e. non-TRPV1 proteins).

MKKWSSTDLGAAADPLQKDTCPDPLDGDPNSRPPPAKPQLSTAKSRTRLFGKGDSEEAFPVDCPHEEGELDSCPTITVSPVITIQRPGDGPTGARLLSQDSVAASTEKTLRLYDRRSIFEAVAQNNCQDLESLLLFLQKSKKHLTDNEFKDPETGKTCLLKAMLNLHDGQNTTIPLLLEIARQTDSLKELVNASYTDSYYKGQTALHIAIERRNMALVTLLVENGADVQAAAHGDFFKKTKGRPGFYFGELPLSLA ACTNQLGIVKFLLQNSWQTADISARDSVGNTVLHALVEVADNTADNTKFVTSMYNEILMLGAKL HPTLKLEELTNKKGMTPLALAAGTGKIGVLAYILQREIQEPECRHLSRKFTEWAYGPVHSSLYDL SCIDTCEKNSVLEVIAYSSSETPNRHDMLLVEPLNRLLQDKWDRFVKRIFYFNFLVYCLYMIIFT MAAYYRPVDGLPPFKMEKTGDYFRVTGEILSVLGGVYFFFRGIQYFLQRRPSMKTLFVDSYSE MLFFLQSLFMLATVVLYFSHLKEYVASMVFSLALGVVTNMLYYTRGFQQMGIYAVMIEKMILRDL CRFMFVYIVFLFGFSTAVVTLIEDGKNDSLPSESTSHRWRGPACRPPDSSYNSLYSTCLELFKF TIGMGDLEFTENYDFKAVFIILLLAYVILTYILLLNM-LIALMGETVNKIAQESKNIWKLQRAITILDTE KSFLKCMRKAFRSGKLLQVGYTPDGKDDYRWCFRVDEVNVVTTWNTNVGIINEDPGNCEGVK RTLSFSLRSSRVSGRHWKNFALVPLLREASARDRQSAQPEEVYLRQFSGSLKPEDAEVFKSPA ASGEK

The present invention therefore enables functional studies of specific epitopes, or evaluation of putative binding sites for novel antibodies, for a target membrane protein residing in its native lipid environment.

In accordance with the present invention, an antigenic epitope is typically based on a surface-exposed peptide that has been cleaved off from a protein during limited or restricted proteolysis. Alternatively viewed, a surface-exposed peptide is typically used to generate an antigenic epitope.

In this regard, an antigenic epitope may comprise the amino acid sequence of the surface-exposed peptide or a sequence substantially homologous thereto. The antigenic epitope may consist of the amino acid sequence of the surface-exposed peptide or a sequence substantially homologous thereto. The antigenic epitope may overlap with the amino acid sequence of the surface-exposed peptide or a sequence substantially homologous thereto.

Amino acid sequences that are "substantially homologous" to surface-exposed peptides include sequences having, or sequences comprising a sequence that has, 1, 2, or 3 amino acid substitutions (preferably 1 or 2, more preferably 1) compared with the amino acid sequence of the given surface-exposed peptide.

Amino acid sequences that are "substantially homologous" to surface-exposed peptides include sequences that comprise (or consist of) at least 5 or at least 6 consecutive amino acids of the surface-exposed peptides (or comprise or consist of at least 7, at least 8, at least 9, at least 10, at least 11, at least 12, at least 15, at least 20 or at least 25) consecutive amino acids of the surface-exposed peptide). Six amino acids is a typical length of peptide/protein sequence that is recognized or bound by an antibody.

Amino acid sequences that are "substantially homologous" to surface-exposed peptides include sequences having, or sequences comprising a sequence that has, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 98% sequence identity to the given surface-exposed peptide sequence. Sequence identities of at least 70%, at least 75%, at least 80%, at least 85%, at least 90%, at least 95%, or at least 98% are preferred.

An antigenic epitope may comprise (or consist of) an elongated version of a surface-exposed peptide, or an elongated version of an amino acid sequence substantially homologous to the surface-exposed peptide. For example, one or more additional amino acids (e.g. at least 2, at least 3, at least 4, at least 5, at least 6, at least 7, at least 8 or at least 9, at least 10, at least 15 or at least 20 amino acids) may be present at one end or both ends of the surface-exposed peptide sequence (or sequence substantially homologous thereto).

An antigenic epitope may comprise (or consist of) a truncated version of a surface-exposed peptide, or a truncated version of an amino acid sequence substantially homologous to the surface-exposed peptide. For example, one or more amino acids (e.g. at least 2, at least 3, at least 4, at least 5, at least 6, at least 7, at least 8 or at 9, at least 10) may be absent from one end or both ends of the surface-exposed peptide sequence (or sequence substantially homologous thereto).

An antigenic epitope may be a cyclic peptide, e.g. substantially homologous to one or several surface-exposed peptides where the surface-exposed peptides are positioned close to each other in space.

Antigenic epitopes may be at least 5, or at least 6 or at least 7 amino acids in length, for example 6 to 10, 6 to 12, 6 to 15, 6 to 20, 6 to 25, 6 to 30, 6 to 40, 6 to 50, 6 to 60, or 6 to 75 amino acids in length. Antigenic epitopes may be, for example, 5 to 7 or 5 to 8 or 5 to 9 (e.g. 7 to 9 amino acids) in length.

Homology (e.g. sequence identity) may be assessed by any convenient method. However, for determining the degree of homology (e.g. identity) between sequences, computer programs that make multiple alignments of sequences are useful, for instance Clustal W (Thompson, Higgins, Gibson, *Nucleic Acids Res.*, 22:4673-4680, 1994). If desired, the Clustal W algorithm can be used together with BLOSUM 62 scoring matrix (Henikoff and Henikoff, *Proc. Natl. Acad. Sci. USA*, 89:10915-10919, 1992) and a gap opening penalty of 10 and gap extension penalty of 0.1, so that the highest order match is obtained between two sequences wherein at least 50% of the total length of one of the sequences is involved in the alignment. Other methods that may be used to align sequences are the alignment method of Needleman and Wunsch (Needleman and Wunsch, *J. Mol. Biol.*, 48:443, 1970) as revised by Smith and Waterman (Smith and Waterman, *Adv. Appl. Math.*, 2:482, 1981) so that the highest order match is obtained between the two sequences and the number of identical amino acids is determined between the two sequences. Other methods to calculate the percentage identity between two amino acid sequences are generally art recognized and include, for example, those described by Carillo and Lipton (Carillo and Lipton, *SIAM J. Applied Math.*, 48:1073, 1988) and those described in Computational Molecular Biology, Lesk, e.d. Oxford University Press, New York, 1988, Biocomputing: Informatics and Genomics Projects.

Generally, computer programs will be employed for such calculations. Programs that compare and align pairs of sequences, like ALIGN (Myers and Miller, *CABIOS*, 4:11-17, 1988), FASTA (Pearson and Lipman, *Proc. Natl. Acad. Sci. USA*, 85:2444-2448, 1988; Pearson, Methods in Enzymology, 183:63-98, 1990) and gapped BLAST (Altschul et al., *Nucleic Acids Res.*, 25:3389-3402, 1997), BLASTP, BLASTN, or GCG (Devereux, Haeberli, Smithies, *Nucleic Acids Res.*, 12:387, 1984) are also useful for this purpose. Furthermore, the Dali server at the European Bioinformatics institute offers structure-based alignments of protein sequences (Holm, *Trends in Biochemical Sciences*, 20:478-480, 1995; Holm, *J. Mol. Biol.*, 233:123-38, 1993; Holm, *Nucleic Acid Res.*, 26:316-9, 1998).

Antigenic epitopes in accordance with the present invention may be linear epitopes or conformational epitopes.

In some embodiments, antigenic epitopes in accordance with the present invention may be cyclized epitopes.

A common technique used for preparing linear antigenic epitopes used for immunization is Fmoc SPPS (Solid Phase Peptide Synthesis). In SPPS, small porous beads are treated with functional linkers on which peptide chains can be built using repeated cycles of wash-coupling-wash. The synthesized peptide is then released from the beads using chemical cleavage. For synthesis of cyclic peptides, common methods utilize cyclization by formation of a disulphide bridge (where the bridge is formed bridge by two cysteines), or by formation of a "head-to-tail" bridge where the bridge consists of a typical peptide bond. Cyclic peptides can be formed on a solid support. Antibodies against conformational epitopes are commonly raised using the entire protein or larger parts of the protein.

Limited or restricted proteolysis includes proteolytic digestion of a protein that does not go to completion. Thus, via limited or restricted proteolysis a given protein may only be partially digested (or partially deconstructed or partially truncated). Limited or restricted proteolysis may be considered as partial proteolysis. If a given protein has a certain number of potential cleavage points for a given protease (i.e. sites recognizable by a given protease for cleavage), under limited or restricted proteolysis the protease may cleave only at a subset of those cleavage sites.

Limited or restricted proteolysis also includes proteolysis done under limiting conditions whereby the kinetics of protease activity is slowed down to the extent that peptides are cleaved off from the protein one at the time, or at most a few at a time. In some embodiments the kinetic activity of said at least one protease is slowed down so much that said surface-exposed peptides are cleaved off one at a time or at most a few at a time, for example at most 8 (1, 2, 3, 4, 5, 6, 7 or 8) at a time (e.g. at most 8 peptides or at most 8 unique peptides in a sample, e.g. as described elsewhere herein), or at most 7 (1, 2, 3, 4, 5, 6 or 7) at a time (e.g. at most 7 peptides or at most 7 unique peptides in a sample, e.g. as described elsewhere herein), or at most 5 (1, 2, 3, 4 or 5) at a time (e.g. at most 5 peptides or at most 5 unique peptides in a sample, e.g. as described elsewhere herein). In some such embodiments, the proteolysis reaction may go to completion such that the protein is exhausted of peptides that can be cleaved off by a given protease.

As described elsewhere herein, typically, limited or restricted proteolysis results in only the most flexible and/or surface-exposed parts of the protein being cleaved by the protease.

In some embodiments of the present invention, said at least one protease is used under conditions which result in at most 8 surface exposed peptides (e.g. 1, 2, 3, 4, 5, 6, 7 or 8 surface-exposed peptides) being cleaved off from the protein by the action of said protease (e.g. at most 8 peptides or at most 8 unique peptides in a sample, e.g. as described elsewhere herein).

In a preferred embodiment, said at least one protease is used under conditions which result in at most 7 surface-exposed peptides (e.g. 1, 2, 3, 4, 5, 6 or 7 surface-exposed peptides) or at most 5 surface-exposed peptides (e.g. 1, 2, 3, 4 or 5 surface exposed peptides) being cleaved off from the protein by the action of said protease (e.g. at most 7 or at most 5 peptides or at most 7 or at most 5 unique peptides in a sample, e.g. as described elsewhere herein).

Limited or restricted proteolysis in accordance with the present invention can typically be achieved by reducing the protease activity, for example by slowing down the kinetics of protease activity to the extent that peptides are cleaved off from the protein one at the time, or at most a few at a time. In some embodiments the kinetic activity of said at least one protease is slowed down so much that said surface-exposed peptides are cleaved off one at a time or at most a few at a time, for example at most 8 (1, 2, 3, 4, 5, 6, 7 or 8) at a time, or most 7 at a time (1, 2, 3, 4, 5, 6 or 7), or at most 5 (1, 2, 3, 4 or 5) at a time, e.g. as described above.

Any suitable conditions may be used for limited or restricted proteolysis in order to result in only the most flexible and/or surface surface-exposed parts of the protein being cleaved by the protease, for example to result in at most 8 surface exposed peptides, or at most 7 surface exposed peptides, or at most 5 surface exposed peptides being cleaved off by the protease. Conditions which lead to limited or restricted proteolysis may be established by varying the temperature of the digestion reaction and/or the concentration of the protease and/or the duration of the digestion reaction and/or the buffer conditions. The number of peptides being cleaved off from the peptide under particular conditions can be determined by a person skilled in the art (e.g. by mass spectrometry or protein chemistry or biochemistry). Suitable ways of establishing appropriate conditions for limited or restricted proteolysis are also described elsewhere herein. Appropriate limited or restricted proteolysis conditions can be established for different proteins or for different proteases or for the particular combination of protein and protease being used. Particularly preferred conditions for limited or restricted proteolysis are described in the Examples herein. Conditions used for limited or restricted proteolysis typically do not alter (or do not significantly alter) the native configuration (native form) of the protein. Cofactors of the protein may be, but are not necessarily, present during limited or restricted proteolysis.

Appropriate conditions for limited or restricted proteolysis may differ depending on the protease and/or protein but are generally conditions that are suboptimal for the protease in question, e.g. such that the kinetics of protease activity is significantly slowed down or reduced.

Conditions which confer (or provide) a low proteolytic activity of the protease (e.g. a lower or significantly lower than optimal proteolytic activity) are generally used. Such conditions include, but are not limited to, using a low concentration of the protease and/or a working temperature that is suboptimal for the protease in question and/or a non-standard or suboptimal buffer for the protease in question and/or a short contact (incubation) time for the protease with the protein.

In some embodiments, limited or restricted proteolysis (e.g. using trypsin or e.g. using a protease with an optimum working temperature of for example 37° C. or above) is performed at room temperature (e.g. about 20° C. or 17-23° C.).

In some embodiments, limited or restricted proteolysis is performed at a temperature that is at least 2° C., at least 5° C., at least 10° C., or at least 20° C. above or below, or significantly above or below, (preferably below) the optimum working temperature of the protease being used.

In some embodiments, a concentration of up to 5 µg/ml protease (e.g. trypsin) is used for limited or restricted proteolysis. In some embodiments, the limited proteolysis reaction is allowed to proceed for up to or less than 5 minutes, 10 minutes, 15 minutes, 30 minutes, one hour or five hours, with the shorter incubation times generally being preferred. In some such embodiments, limited proteolysis is performed at room temperature. Thus, in some embodiments, limited proteolysis is performed with a concentration of up to 5 µg/ml protease (e.g. about 5 µg/ml protease) for up to about 5 minutes (e.g. about 5 minutes) at room temperature.

In some embodiments, proteolytic digestion reactions may be stopped using formic acid or aqueous ammonia. For example, trypsin, Asp-N, Proteinase K and chymotrypsin may be stopped using formic acid and pepsin may be stopped using aqueous ammonia.

In some embodiments of the present invention, the cleaved off surface exposed peptides are ranked based on order of appearance after being contacted with said at least one protease, wherein the surface exposed peptides that are cleaved off first (or early) and detected in the first (or early) sampling points are given a high rank and the surface exposed peptides that are cleaved off late and detected in subsequent sampling points are given a low rank. Highly-ranked peptides, coming off the target protein quickly, also having functional significance may typically be used for epitope development, immunization and subsequent antibody generation.

In some embodiments of the invention, the surface exposed peptides that are cleaved off under conditions of low (less harsh) proteolytic activity as described herein (e.g. low(er) concentration of protease, low(er) temperature of incubation, and/or short(er) time of incubation, generally easily digested peptides) are given a high rank and the surface exposed peptides that are cleaved off under conditions of high (more harsh) proteolytic activity as described herein (e.g. high(er) concentration of protease, high(er) temperature of incubation and/or long(er) temperature of incubation, generally less easily digested peptides) are given a low rank.

In some embodiments, multiple samples of proteolytically digested material (or eluate from the proteolytic digestion reaction) may be taken during a limited or restricted proteolysis reaction (e.g. sequentially) and/or multiple samples (e.g. multiple limited or restricted proteolysis reactions) may be processed (or run) separately (e.g. processed or run in parallel).

In some embodiments, multiple samples of proteolytically digested material (or eluate from the proteolytic digestion reaction) are taken (or obtained) at time intervals (e.g. 1 minute, 2.5 minutes or 5 minute intervals) during limited or restricted proteolysis of the protein. In some such embodiments, the protease and/or (typically "and") the protease concentration (and/or other conditions that may effect proteolysis as described elsewhere herein) may be constant for (or in) each of the samples, with the samples varying based on the time (or duration) of contact (or incubation) with the protease. In some such embodiments, samples may be obtained in sequence (sequential digestion).

In some embodiments, multiple samples (e.g. multiple limited or restricted digestion reactions) are processed (or run) separately, with each sample having different proteolytic conditions or proteolytic activities for limited or restricted proteolysis of the protein, for example as discussed elsewhere herein, e.g. different proteases and/or different protease concentrations and/or different temperatures and/or different times of incubation may be used in different samples. In some such embodiments, the time (or duration) of the contact (or incubation) with the protease is typically (and preferably) constant for (or in) each of the samples. In some such embodiments, samples may be processed (or run) in parallel.

In some embodiments of methods of the invention, the number of surface exposed peptides being cleaved off from the protein by the action of said protease is controlled by time at a constant concentration of protease and several samples are taken over time, or the number of surface exposed peptides being cleaved off from the protein by the action of said protease is controlled by the concentration of the protease at constant time, and several samples can be taken (or run) at several different concentrations of the protease, or the number of surface exposed peptides being cleaved off from the protein by the action of said protease is controlled by both time and concentration of said protease.

Each sample (or preferred samples) may preferably contain one or a few peptides (e.g. up to 8 peptides or up to 8 unique peptides) that have been cleaved off from the protein. Thus, one or a few peptides (e.g. up to 8 peptides or up to 8 unique peptides) that have been cleaved off from the protein may be detected in each sample. A unique peptide is a peptide that is not present in a previous sample or not present in a sample with weaker (or less harsh) proteolytic conditions (e.g. is distinct from or different from peptides present in a previous sample or in a sample with weaker proteolytic conditions). Accordingly, a sample that contains up to 8 unique peptides may contain greater than 8 different peptides, but one or more of these peptides may have been detected in a previous sample or in a sample with weaker proteolytic conditions (and thus one or more of these peptides may be a non-unique peptide).

Ideally, and preferably, each sample would contain only a single cleaved off peptide. For example, a single cleaved off peptide may be detected in the first sample (or sampling point) and a single cleaved off peptide may be detected in one or more subsequent samples (or sampling points). In other examples, multiple cleaved off peptides (e.g. up to 8 peptides or up to 8 unique peptides) may be detected in the first and/or subsequent samples (sampling points). Conditions that yield one or a few cleaved off peptides per sample (e.g. up to 8 peptides or up to 8 unique peptides per sample) can be established by using short sampling intervals, different protease concentrations, different buffer compositions, different temperatures, different salt concentrations, or protease inhibitors (or a combination thereof). Cleaved-off peptides may be ranked based on the sample (sampling point) in which they appear. For example, under conditions which result in the detection of only one peptide per sampling point, the peptide in the first sample taken is given the highest rank, the peptide in the second sample taken is given rank 2, etc. Using conditions whereby only a single cleaved off peptide is detected at each sampling point, ranking of individual peptides is possible. Using conditions whereby multiple cleaved off peptides are detected at each sampling point, ranking of groups of peptides is possible.

In some embodiments, higher ranked surface-exposed peptides (cleaved off peptides) are preferred. In some embodiments, the surface-exposed peptide (e.g. a high rank peptide) in accordance with the invention is a cleaved off peptide that is detected in (or present in) the first sample taken. In some embodiments, a surface-exposed peptide in accordance with the invention (e.g. a high ranked peptide) is a cleaved off peptide that is one of the top 8 ranked peptides (e.g. top 8 ranked unique peptides) or is present in a sample containing one of the top 8 ranked peptides (e.g. top 7 ranked, or top 5 ranked) peptides (e.g. top 8, top 7 or top 5 ranked unique peptides) in terms of its order of appearance in a sample(s) taken during limited or restricted proteolysis of the protein. Such peptides may be detected in (or present in) the first sample taken, or may be present in one or more subsequently taken samples.

Peptides that are cleaved off from the protein first (or early) (e.g. those in the first sample taken (first sampling point) as described above or those that are ranked in the top 8 peptides (e.g. top 8 ranked unique peptides) based on order of appearance during limited or restricted proteolysis as described above) are typically those that are well exposed (e.g. surface exposed) and thus are easily accessed by the protease. Such first (or early) digested peptides are given a high rank (e.g. the first appearing peptide is given rank 1, the second given rank 2, etc.). Peptides that are cleaved off from the protein later (e.g. in a later sampling point than the early peptides) are typically those that are not as well exposed and thus are not as easily accessed by the protease. Such later digested peptides are given a lower rank. In the present invention, peptides having a high rank are typically preferred.

In some embodiments, cleaved off peptides (surface exposed peptides) having amino acid sequences that are most exposed at the surface of the protein are preferred for antigenic epitope development.

In some embodiments, peptides (cleaved-off peptides) may be ranked based on their functional importance, or predicted functional importance, to the protein. Typically, those peptides having amino acid sequences that are functionally important, or predicted to be of functional importance, to the protein are given a higher rank than those that are not, or not predicted to be, of functional importance. In some embodiments, it is the higher ranked peptides that are preferred.

In some embodiments, peptides having amino acid sequences that are functionally important, or that are predicted to be functionally important, to the protein (e.g. have a high rank for functional importance) and which additionally have a high rank based on surface exposure (e.g. a peptide in the first sample taken (first sampling point) as described above or those that are ranked in the top 8 peptides (e.g. top 8 ranked unique peptides) based on order of appearance during limited or restricted proteolysis as described above) are preferred for antigenic epitope development (or put another way are preferred peptides upon which to base an antigenic epitope).

In some embodiments, peptides having amino acid sequences that are functionally important, or that are predicted to be functionally important, to the protein (e.g. have a high rank for functional importance), but which do not additionally have a high rank based on surface exposure (e.g. are not peptides in the first sample taken (first sampling point) as described above or those that are ranked in the top 8 peptides (e.g. top 8 ranked unique peptides) based on order of appearance during limited or restricted proteolysis as described above) may be used for antigenic epitope development.

In some embodiments, peptides having amino acid sequences that are not functionally important, or that are not predicted to be functionally important, to the protein (e.g. have a low rank for functional importance) but which have a high rank based on surface exposure (e.g. a peptide in the first sample taken (first sampling point) as described above or those that are ranked in the top 8 peptides (e.g. top 8 ranked unique peptides) based on order of appearance during limited or restricted proteolysis as described above) may be used for antigenic epitope development.

In some embodiments, an antigenic epitope is based on a surface exposed peptide that is cleaved off first (or early) from said protein (e.g. a peptide in the first sample taken (first sampling point) as described above or a peptide that is ranked in the top 8 peptides (e.g. top 8 ranked unique peptides), based on order of appearance during limited or restricted proteolysis as described above), irrespective of the functional importance, or predicted functional importance, of the amino acid sequence of the cleaved off peptide.

In some embodiments, an antigenic epitope is based on a surface exposed peptide that is ranked in the top 8 peptides (e.g. top 8 ranked unique peptides), based on order of appearance during limited or restricted proteolysis, of those peptides that additionally have an amino acid sequence that is functionally important, or predicted to be of functional importance, to the protein. These peptides are not necessarily (but may be) the same as the set of the absolute top ranked 8 peptides based on order of appearance alone (as described above).

In some embodiments, a region of interest on a protein is identified or selected which is, or is predicted to be, functionally important to the protein, and an antigenic epitope is based on a surface exposed peptide that is ranked in the top 8 peptides (e.g. top 8 ranked unique peptides), based on order of appearance during limited or restricted proteolysis, of those peptides that additionally have an amino acid sequence that cleaved off from said region of interest. These peptides are not necessarily (but may be) the same as the set of the absolute top ranked 8 peptides based on order of appearance alone (as described above).

In some embodiments, antigenic epitopes for antibody generation are based on the amino acid sequence of a peptide (surface exposed peptide) that has been cleaved off first (or early) (e.g. a peptide in the first sample taken (first sampling point) as described above or a peptide that is ranked in the top 8 peptides (e.g. top 8 ranked unique peptides) based on order of appearance during limited or restricted proteolysis as described above) from said protein by the action of the protease during limited proteolysis and thus which has a high rank.

Thus, in some embodiments, methods of the invention comprise picking a surface exposed peptide having a high rank (e.g. a peptide in the first sample taken (first sampling point) as described above or a peptide that is ranked in the top 8 peptides (e.g. top 8 ranked unique peptides) based on order of appearance during limited or restricted proteolysis as described above) for antigenic epitope development and raising an antibody against said antigenic epitope that is based on (or developed from) said surface-exposed peptide.

In some embodiments, methods of the invention comprise picking a surface exposed peptide having a high rank (e.g. a peptide in the first sample taken (first sampling point) as described above or a peptide that is ranked in the top 8 peptides (e.g. top 8 ranked unique peptides based on order of appearance during limited or restricted proteolysis as described above), constructing an antigenic epitope based on said surface-exposed peptide and raising an antibody against said antigenic epitope.

In some embodiments, methods of the invention comprise picking a surface exposed peptide having a high rank (e.g. a peptide in the first sample taken (first sampling point) as described above or a peptide that is ranked in the top 8 peptides (e.g. top 8 ranked unique peptides) based on order of appearance during limited or restricted proteolysis as described above) and correlating it with a defined biological property (or biological function) of the protein, constructing an antigenic epitope based on said surface-exposed peptide and raising an antibody against said antigenic epitope. Peptides having an amino acid sequence which correlates with a defined biological property (or function) of the protein are typically preferred.

Any means for identifying the cleaved off peptides (surface-exposed peptides) may be employed. In some embodiments, cleaved off peptides are identified using mass spectrometry. In some embodiments, liquid chromatography in combination with mass spectrometry is used. Preferably, cleaved off peptides (surface-exposed peptides) are identified with LC-MS/MS (liquid chromatography-tandem mass spectrometry). Exemplary and preferred mass spectrometry methodologies are described in the Examples. Tandem mass-spectra may be searched by MASCOT (Matrix Science, London, UK) against an appropriate database, e.g. as described in the Examples.

A digested, deconstructed or truncated protein as referred to herein is a protein that has been cleaved at one or more sites along its length by a protease. Such proteolytic cleavage results in one or more peptides (surface exposed peptides) being cleaved off from (i.e. released from) the protein. Thus, a surface exposed peptide is a peptide that has been cleaved off from a protein by the action of the protease. The term "surface exposed" reflects the fact that, typically, in the context of the full-length protein (i.e. the uncleaved protein), the portion of the protein that corresponds to the cleaved off (released) peptide sequence is well exposed and accessible to the protease.

The present invention provides new methods for therapeutic antibody discovery, and new pharmacologically active antibodies directed to the human TRPV1 protein.

The present invention relates to methods of detecting epitopes on proteins that are well exposed and thus may be utilized as guides for antibody targeting.

Some methods of the present invention comprise a step of identifying an antigenic epitope by identifying a surface-exposed peptide that is cleaved off that has an amino acid sequence that is, or that is predicted to be, of functional importance (e.g. biological importance) to said protein, and generating an antigenic epitope based on such a surface-exposed peptide. In some embodiments, an antibody is raised against such an antigenic epitope.

Identifying whether or not a surface-exposed peptide that is cleaved off from said protein has an amino acid sequence that is, or is predicted to be of functional importance to said protein can be done by any suitable means and a person skilled in the art will readily be able to do this.

For example, in some embodiments, a protein that is digested, deconstructed or truncated during limited or restricted proteolysis is tested in a functional assay to assess whether its function or functional activity (e.g. biological function) has been altered. This may be done by comparing the level of functional activity of the digested, deconstructed or truncated protein to the level of functional activity of the protein that has not been subjected to limited or restricted proteolysis (the level of functional activity of the protein that has not been subjected to limited or restricted proteolysis can be considered a control level). If the biological function of a protein is altered after (or during) the limited or restricted proteolysis, this indicates that the cleaved off-peptide(s) (surface exposed peptide(s)) has been cleaved off (released) from a region of the protein that is of functional relevance to the protein (e.g. that is of biological importance). Accordingly, cleaved-off surface exposed peptides can be correlated with functional data to assess the functional importance of the surface-exposed peptides to the protein. The cleaved off peptide(s) can be identified (e.g. the sequence(s) of the cleaved off peptide(s) can be identified), e.g. in a parallel experiment, as described elsewhere herein (e.g. by LC-MS/MS). If the cleaving off of a peptide (surface-exposed peptide) from the protein results in an alteration of the functional activity of the protein, this indicates that the surface-exposed peptide may be particularly useful for antigenic epitope generation in the present invention. Alternatively viewed, an antigenic epitope based on such a surface-exposed peptide may be particularly useful and preferred for antibody generation.

In one embodiment the protein is TRPV1 and the assay to determine the functional importance of the cleaved off peptides to TRPV1 is an inside-out patch-clamp assay as described elsewhere herein.

An "altered" or "alteration in" function or functional activity can be any measurable alteration, preferably a significant alteration, more preferably a statistically significant alteration. An "altered" function or "alteration in function" may be an increase or decrease in function. Exemplary alterations in function are alterations of $\geq 2\%$, $\geq 3\%$, $\geq 5\%$, $\geq 10\%$, $\geq 25\%$, $\geq 50\%$, $\geq 75\%$, $\geq 100\%$, $\geq 200\%$, $\geq 300\%$, $\geq 400\%$, $\geq 500\%$, $\geq 600\%$, $\geq 700\%$, $\geq 800\%$, $\geq 900\%$, $\geq 1000\%$, $\geq 2000\%$, $\geq 5000\%$, or $\geq 10,000\%$. Alterations are typically as assessed in comparison to an appropriate control level of function or functional activity, for example in comparison to the function or functional activity of the equivalent protein that has not been subjected to limited or restricted proteolysis.

In some embodiments, an antigenic epitope is based on the amino acid sequence of a surface-exposed peptide that, when cleaved off from the protein, results in an alteration in the function or functional activity of the protein.

In some embodiments, whether or not the surface-exposed peptide sequence is of functional importance (e.g.

biological importance) is predicted or determined by bioinformatic means and/or by using other information (e.g. in academic literature) that is already known about functionally important regions of the protein. Accordingly, cleaved off surface exposed peptides can be correlated with data that is known about functionally important regions of the protein to predict or determine the functional importance of the cleaved off peptide to the protein. If the amino acid sequence of the surface-exposed peptide is known to be (or is predicted to be) of functional importance, this indicates that the surface-exposed peptide may be particularly useful for antigenic epitope generation in the present invention. Alternatively viewed, an antigenic epitope based on such a surface-exposed peptide may be particularly useful and preferred for antibody generation.

Thus, in some embodiments, an antigenic epitope is based on the amino acid sequence of a surface exposed peptide that is known to be (or is predicted to be) functionally important, e.g. based on bioinformatic analysis and/or based on other information (e.g. in academic literature) that is already known about functionally important regions of the protein.

In some embodiments, the antigenic epitope is an antigenic epitope of TRPV1 that is based on the amino acid sequence of a surface exposed peptide that correlates with (or corresponds to) a calmodulin binding sequence of TRPV1 or the capsaicin binding site of TRPV1.

In some embodiments, a functional assay to determine the functional importance of a surface-exposed peptide is performed in addition to predicting or determining the functional importance of a surface-exposed peptide by bioinformatic means and/or by using other information (e.g. in academic literature) that is already known about functionally important regions of the protein.

"Bioinformatic means", "bioinformatic analysis", "bioinformatic data" and "bioinformatic information" includes, but is not limited to, database searching (e.g. BLAST searching), structural modeling, or structural biology and data/information obtained thereby.

Function (e.g. biological function) can include any biological or physiologically relevant function for the protein in question. Function (e.g. biological function) includes, but is not limited to the capability of the protein to bind to a target (such as a ligand or receptor) or other binding partner e.g. a cofactor, signalling activity, enzymatic activity of the protein, and ion channel activity, transporter activity, release e.g. insulin release and uptake machinery, etc. Thus, functionally relevant or functionally important regions of the protein include, but are not limited to, regions that confer the ability of the protein to bind to a target (such as a ligand or receptor) or other binding partner e.g. a cofactor, regions that confer signalling activity, regions that have an enzymatic activity of the protein, regions that confer ion channel activity, regions conferring transporter activity and regions conferring release and uptake of molecules (e.g. insulin).

In one embodiment, a method of the invention further comprises a step of in silico generation of a set of putative peptides (e.g. all putative peptides) that could be cleaved off from the protein by one or more protease (e.g. by using a computer program that can identify cleavage points in a protein based on the known recognition sequence(s) of said one or more proteases), and optionally filtering said in silico generated set of putative peptides to remove peptides that have previously been described (e.g. in sequence databases for example BLAST searching or in other literature) thereby obtaining a filtered list of putative peptides, comparing said filtered list of putative peptides to a list of peptides identified by limited or restricted proteolysis of the protein, identifying the peptides that are common to both said filtered list and said list of peptides identified by limited or restricted proteolysis of the protein, identifying (or constructing) an antigenic epitope based on a peptide common to both lists, and optionally raising an antibody to said antigenic epitope.

In another aspect, the present invention provides a method of identifying an antigenic epitope, said method comprising:
(i) exposing a first protein to limited or restricted proteolysis by contacting the first protein with at least one protease to form at least one digested, deconstructed or truncated version of the first protein and at least one surface-exposed peptide that is cleaved off from the first protein by the action of said protease;
(ii) identifying an amino acid sequence of a region (or part or portion) of a second protein that is identical to or substantially homologous to the amino acid sequence of a surface-exposed peptide that is cleaved off from the first protein; and
(iii) generating an antigenic epitope based on the amino acid sequence of said region (or part or portion) of said second protein that is identical to or substantially homologous to the amino acid sequence of a surface-exposed peptide that is cleaved off from the first protein; and optionally
(iv) raising an antibody against the antigenic epitope.

Exemplary types of substantially homologous sequence are discussed elsewhere herein. Such a method can facilitate antigenic epitope generation for a protein (a second protein) based on limited or restricted proteolysis performed on a different protein (a first protein). This may be particularly useful when the first and second proteins are in the same protein family or otherwise related, for example data from limited or restricted proteolysis performed on TRPV1 may be used to identify a TRPV2 antigenic epitope. Determining (or identifying) substantially homologous proteins on a second protein may be done using any suitable means (e.g. computer programs) and a skilled person will familiar with these. Purely by way of example, the EMBOSS Needle program provided by EMBL-EBI is a suitable computer program. EMBOSS Needle reads two input sequences and writes their optimal global sequence alignment, the computation using the Needleman-Wunsch alignment algorithm to find the optimum alignment (including gaps) of two sequences along their entire length.

In some embodiments of the invention, an antigenic epitope is not based on a surface exposed peptide that has an amino acid sequence that is conserved with another protein (s) (e.g. an evolutionarily conserved sequence or a sequence that is identical to or substantially homologous to the amino acid sequence of the surface exposed peptide). This may minimise the cross-reactivity (or non-specific binding) of the antibodies raised against such antigenic epitopes. Put another way, antigenic epitopes based on unique amino acid sequences (or sequences not found in other proteins) can be used in some embodiments The present invention relates to methods of detecting epitopes on proteins that are functionally relevant and thus may be utilized as guides for antibody targeting. More specifically, such methods include proteomic tools to reveal hot spot epitopes of target proteins. These epitopes that potentially can be used as antigens in the production of antibodies are denoted antigenic epitopes herein.

In an aspect of the invention, a protein is digested, deconstructed and/or truncated through protease action and in parallel probed by one or more functional assays on the digested, deconstructed and/or truncated protein to delineate functionally important region(s) of the protein.

In an embodiment the digestion, deconstruction and/or truncation of the protein may be performed in parallel by functional assay(s) to delineate functionally important regions of the protein to guide epitope selection for antibody generation.

In an embodiment, a single protease may be used to digest, deconstruct and/or truncate the protein. In another embodiment, multiple proteases may be used to digest, deconstruct and/or truncate the target protein, sequentially one at a time or in parallel. Such proteases are exemplified but not limited to Arg-C proteinase, Asp-N endopeptidase, Clostripain, Glutamyl endopeptidase, Lys-C, Lys-N, Trypsin, Chymotrypsin, Proteinase K and Thermolysin. A region that is easily digested by several proteases should be located in an exposed region of the protein and a region that is only digested by a single protease is probably located in a more hidden region. Alternatively, the protease has unique cleaving specificity or/and physicochemical properties or/and structural features such that it can identify surface-exposed peptides on a target protein that other proteases cannot. Thus, the usage of multiple proteases is preferable, and each different protease can yield complementary or unique information about surface-exposed peptides suitability as antigenic epitopes.

Sequential use of multiple proteases means that different proteases are incubated with the protein one after another, i.e. one protease is incubated, followed by another at a later time point, and optionally one or more other different proteases at a later time point(s).

Sequential use of a single protease means that the same protease (e.g. the same concentration of protease) is incubated with the protein several times, e.g. at several different (sequential) time points or that several samples are taken over time from the proteolytic digest reaction, and the appearance of new or unique peptides generated in the reaction are detected and followed over time.

Parallel use means that multiple separate, single-protease digestion reactions are performed, each with a different protease, or with the same protease but different proteolytic conditions, for example as described elsewhere herein e.g. different protease concentrations and/or temperatures and/or time points.

Multiple proteases may be used in order to identify overlapping, complementary or unique surface-exposed peptides. In this context "overlapping" means that a surface-exposed peptide identified via limited or restricted proteolysis with one protease has an amino acid sequence which overlaps (partially or fully) with the amino acid sequence of a surface-exposed peptide identified via limited or restricted proteolysis with one or more other (i.e. different) proteases. In this context, "complementary" means that a surface-exposed peptide identified via limited or restricted proteolysis with one protease has an amino acid sequence which, in the context of the entire protein sequence (i.e. the entire protein sequence before limited or restricted proteolysis), lies next to or close to (or even partially overlaps with) the amino acid sequence of a surface-exposed peptide identified via limited or restricted proteolysis with one or more other (i.e. different) proteases. A "unique" surface exposed peptide is surface-exposed peptide that is only identified after limited or restricted proteolysis with one or few (the minority) of the proteases tested.

Without wishing to be bound by theory, a region of the protein that is cleaved by more than one protease is likely to be in a well exposed (e.g. surface exposed) region of the protein and thus surface-exposed peptides from a region of the protein that is cleaved by more than one protease may represent particularly useful surface-exposed peptides upon which to base antigenic epitopes.

Using multiple proteases includes, but is not limited to, using 2, 3, 4, 5 proteases.

In some embodiments of methods of the present invention, the protease is selected from the group consisting of trypsin, Arg-C proteinase, Asp-N endopeptidase, Clostripain, Glutamyl endopeptidase, Lys-C, Lys-N, Chymotrypsin, Proteinase K, Thermolysin, Pepsin, Caspase 1, Caspase 2, Caspase 3, Caspase 4, Caspase 5, Caspase 6, Caspase 7, Caspase 8, Caspase 9, Caspase 10, Enterokinase, Factor Xa, GranzymeB, Neutrophil elastase, Proline-endopeptidase, Staphylococcal peptidase I, and Thrombin.

In some preferred embodiments, the protease is selected from the group consisting of trypsin, Asp-N endopeptidase, Chymotrypsin, pepsin and Proteinase K. In a preferred embodiment, the protease is trypsin.

In yet another aspect of the invention a cocktail of several proteases are used together in single, or multiple challenges spaced in time with constant or varying concentration of one or several of the proteases. Thus, in some embodiments a single cocktail (mixture) of multiple proteases is used.

If multiple proteases are used a rank-ordered list may be generated for each individual protease.

This method will yield new fundamental understanding of protein function, and new methodology/technology for rapid and precise development of pharmacologically active antibodies that can be used to treat a medical condition in humans and/or animals. The method can be generalized to all proteins, soluble or membrane bound, extracellular or intracellular.

The list of epitopes generated by the proposed method is preferably sorted versus curated bioinformatics data and functional assay(s). The method preferably uses input data from both experiments, and bioinformatic information. In an embodiment, focus will be on membrane, and membrane-associated proteins. Such proteins are exemplified but not limited to the human nociceptor TRPV1, other ion channels in the TRP superfamily, as well as some excitatory amino acids receptors including the NMDA receptor, and G-proteins. These proteins (e.g. ion channels) have the advantage that they can be studied directly in a detailed way using, for example, patch clamp. Other classes of proteins of interest are related to oncogenic proteins, including the oncogenic small GTPases KRAS, NRAS and HRAS. KRAS is a key protein in several metastatic malignancies including pancreatic carcinoma, colon carcinoma, and lung carcinoma. GTPase activity can e.g. be studied by radioisotopic labeling of GTP followed by measurement of free 32P after GTP hydrolysis to GDP or pull-down assays followed by western blot. Yet other interesting protein classes are immunomodulatory proteins involved in immunomodulation in cancer therapy such as PD1, PDL1, CD 40 just as a few examples.

A "protein" in accordance with the present invention may be any protein.

In some embodiments of the present invention, the protein is a membrane bound protein, a soluble (e.g. circulating) protein, an extracellular protein or an intracellular protein.

In some embodiments, the protein is a membrane or a membrane associated protein.

In some embodiments, the protein is an ion channel, e.g. an ion channel in the TRP superfamily (e.g. TRPV1 or TRPV2). In a preferred embodiment, the protein is TRPV1.

In some embodiments, the protein is an excitatory amino acid receptor. In some such embodiments the protein is the NMDA receptor or a G-protein.

In some embodiments, the protein is an oncogenic protein. In some such embodiments the protein is an oncogenic small GTPase selected from the group consisting of KRAS, NRAS and HRAS.

In some embodiments, the protein is an immunomodulatory protein. In some such embodiments the protein is selected from the group consisting of PD1, PDL1, CD40, OX40, VISTA, LAG-3, TIM-3, GITR and CD20.

In some embodiments, the protein is any protein of the human proteome. Put another way, human proteins are preferred.

The usage of a single, or multiprotease limited digestion protocol to these targets will lead to the discovery of new antibodies directed to hot spot epitopes. Different proteases will produce different cleaved off peptides. In an embodiment, membrane proteins are deconstructed and effects of this piece-by-piece truncation are probed for effect on protein function. Rare spots only observed with certain proteases will also be identified. The identified data will then be analyzed against curated bioinformatic data and also from functional assays of truncated proteins, to recognize functionally important regions of the protein in question.

An aspect of the embodiments relates to a method of identifying an antigenic epitope in a protein. The method comprises exposing the protein to limited or restricted proteolysis by contacting the protein to at least one protease to form at least one digested, deconstructed or truncated version of the protein and at least one surface-exposed peptide. In another embodiment, the method also comprises probing the at least one digested, deconstructed or truncated version of the protein in a functional assay that tests, checks or verifies at least one biological function of the protein. The method further comprises identifying an antigenic epitope in the protein as a surface-exposed peptide among the at least one surface-exposed peptide and present in a region of the protein involved in exerting the biological function of the protein as determined based on the functional assay.

In an embodiment, exposing the protein to the limited or restricted proteolysis comprises contacting the protein to the at least one protease i) at a selected temperature or temperature range, ii) at a selected concentration or concentration range of the at least one protease (relative to a concentration of the protein) and/or ii) during a selected duration. This in turn enables the at least one protease to cleave surface-exposed regions of the protein but not non-flexible and/or internal regions of the protein.

Exposing the protein to limited or restricted proteolysis by contacting the protein to at least one protease implies that the protein is exposed to a mild proteolysis. As a consequence, in particular surface exposed and flexible peptide portion(s) of the protein will be cleaved off from the amino acid sequence by the action of the at least one protease. The temperature, concentration and/or duration used in the proteolysis typically depends on the particular protease(s) and the current protein. Thus, in an embodiment a set of candidate proteolysis conditions are first tested in order to select or identify a suitable temperature, concentration of protease and/or duration used to digest, and buffer conditions to deconstruct or truncate the protein and get at least one surface-exposed peptide. For instance, proteolysis can be performed at multiple, i.e. at least two, different reaction temperatures, at multiple different protease concentrations (relative the concentration of the protein) and/or at multiple different reaction durations, including different buffer conditions, as shown in FIG. 1 in order to identify the most appropriate proteolysis conditions for the current combination of protein and protease(s).

A suitable protease condition is, for instance, temperature, concentration and/or duration that results in the digestions, deconstruction or truncation of the protein into one or at most N surface-exposed peptides. A typical value of the parameter N is 7, preferably 6 or 5, more preferably 4 or 3 or even more preferably 2 or 1.

In an embodiment, the functional assay tests, checks or verifies at least one biological function of the protein. Non-limiting examples of such biological function include the capability of the protein to bind to a target, such as a ligand or receptor; enzymatic activity of the protein; ion channel activity; etc.

In an embodiment, exposing the protein to the limited or restricted proteolysis comprises exposing the protein to the limited or restricted proteolysis by contacting the protein to multiple proteases to form multiple digested, deconstructed or truncated versions of the protein and multiple surface-exposed peptides. In a particular embodiment, the protein is contacted to the multiple proteases serially, i.e. one after another. In another particular embodiment, the protein is contacted to the multiple proteases in parallel.

In an embodiment, identifying the antigenic epitope comprises identifying a surface-exposed epitope among the at least one surface-exposed peptide that is present in region that results in lack of or significantly altered biological function of the protein when the region is cleaved off or removed from the protein during the limited or restricted proteolysis.

In an embodiment, the method also comprises selecting at least one target region within the protein based on bioinformatics and/or known data of biological function of the protein. In such a case, identifying the antigenic epitope comprises identifying a surface-exposed peptide among at least one surface-exposed peptide present in a region of the protein among the at least one target region.

In this embodiment, bioinformatics and/or other known data of the biological function is used to guide the antigenic epitope selection. This means that only surface-exposed peptides that are present in one of the selected target regions(s) are used as candidates when identifying or selecting the antigenic epitope. Accordingly, the number of candidates can be reduced by removed or omitting surface-exposed peptides that are present in regions known to lack any biological function and/or known to not be involved in exerting the biological function of the protein.

Another aspect of the embodiments relates to an antigenic epitope identified according to the above described method of identifying an antigenic epitope in a protein.

In one embodiment, the present invention provides an antigenic epitope of TRPV1 comprising (or consisting of) an amino acid sequence selected from the group consisting of:
LLSQDSVAASTEK (SEQ ID NO:2);
LLSQDSVAASTEKTLR (SEQ ID NO:3); and
QFSGSLKPEDAEVFKSPAASGEK (SEQ ID NO:4),
or a sequence substantially homologous thereto.

In another embodiment, the present invention provides an antigenic epitope of TRPV1 comprising (or consisting of) an amino acid sequence selected from the group consisting of:
LLSQDSVAASTEKTLRLYDRRS (SEQ ID NO:5); and
GRHWKNFALVPLLRE (SEQ ID NO:6).

In one embodiment, the present invention provides an antigenic epitope of TRPV1 comprising (or consisting of) an amino acid sequence of LVENGADVQAAAHGDF (SEQ ID NO:7), or a sequence substantially homologous thereto.

In another embodiment, the present invention provides an antigenic epitope of TRPV1 comprising (or consisting of) an amino acid sequence selected from the group consisting of:

DGPTGARLLSQ (SEQ ID NO:8); and
DAEVFKSPAASGEK (SEQ ID NO:9),
or a sequence substantially homologous thereto.

In another embodiment, the present invention provides an antigenic epitope of TRPV1 comprising (or consisting of) an amino acid sequence selected from the group consisting of:
SQDSVAASTEKTL (SEQ ID NO:10); and
SGSLKPEDAEVF (SEQ ID NO:11),
or a sequence substantially homologous thereto.

In one embodiment, the present invention provides an antigenic epitope of TRPV1 comprising (or consisting of) an amino acid selected from the group consisting of:
VSPVITIQRPGD (SEQ ID NO:12);
VSPVITIQRPGDGPTGA (SEQ ID NO:13);
LNLHDGQNTTIPLLL (SEQ ID NO:14);
YTDSYYKGQ (SEQ ID NO:15)
SLPSESTSH (SEQ ID NO:16)
EDPGNCEGVKR (SEQ ID NO:17)
DRQSAQPEEVYLR (SEQ ID NO:18); and
QSAQPEEVYLR (SEQ ID NO:19),
or a sequence substantially homologous thereto.

In some embodiments, the present invention provides an antigenic epitope of TRPV1 comprising an amino acid sequence as set out under the second heading (the heading marked with a double asterisk(**)) in each of Tables 2, 3, 4, 5, and 6 in the Example 3 herein, or a sequence substantially homologous thereto. Such peptides, digested using a higher proteolytic activity (or harsher or stronger proteolytic conditions) are generally less preferred than peptides digested using a lower proteolytic activity (or less harsh or weaker proteolytic conditions) (e.g. shorter time and/or lower concentration e.g. as set out under the first heading (the heading marked with a single asterisk (*) in each of Tables 2, 3, 4, 5, and 6), but may be of particular interest if they are, or are predicted to be, of functional importance to the protein. The peptides set out under the second headings in Tables 2, 3, 4, 5 and 6 (**) may be considered peptides that are digested late and the peptides set out under the first headings in Tables 2, 3, 4, 5 and 6 (*) may be considered peptides that are digested first.

In the context of the above antigenic epitopes of TRPV1, said substantially homologous sequence may be a sequence containing 1, 2, 3, 4, 5 or 6 (preferably 1, 2 or 3) amino acid substitutions or deletions compared to the given amino acid sequence, or is a sequence having at least 70% sequence identity to the given amino acid sequence, or is a sequence having at least 6 consecutive amino acids of the given amino acid sequence. Other examples of "substantially homologous" sequences are described elsewhere herein in relation to amino acid sequences that are "substantially homologous" to surface-exposed peptides and these examples of "substantially homologous" sequence are also applicable to the specific peptide sequences mentioned above. The specific peptide sequences mentioned above are surface-exposed peptide sequences.

In some embodiments, the present invention provides an antigenic epitope that comprises (or consists of) an elongated, truncated or cyclic version of a peptide sequence mentioned above (or a sequence substantially homologous thereto). Elongated, truncated and cyclic versions of peptides are discussed elsewhere herein in the context of elongated, truncated and cyclic surface-exposed peptides and that discussion is also applicable to the peptide sequences mentioned above. The specific peptide sequences mentioned above are surface-exposed peptide sequences.

In one embodiment, the present invention provides an antigenic epitope of TRPV2 comprising (or consisting of) an amino acid selected from the group consisting of:
FAPQIRVNLNYRKGTG (SEQ ID NO:20);
ASQPDPNRFDRDR (SEQ ID NO:21)
LNLKDGVNACILPLL (SEQ ID NO:22)
CTDDYYRGH (SEQ ID NO:23)
LVENGANVHARACGRF (SEQ ID NO:24)
EDPSGAGVPR (SEQ ID NO:25); and
GASEENYVPVQLLQS (SEQ ID NO:26),
or a sequence substantially homologous thereto. Exemplary substantially homologous sequences are discussed elsewhere herein.

A further aspect of the embodiments relates to a conjugate configured to be used for production of antibodies. The conjugate comprises at least one antigenic epitope as defined above coupled to or admixed with a peptide carrier.

Thus, in one aspect, the invention provides a conjugate comprising an antigenic epitope of, or identified by (or produced by), the present invention. Conjugates may comprise an antigenic epitope and any distinct entity (i.e. any entity distinct from the antigenic epitope), for example a label or a peptide carrier. Conjugates typically comprise an antigenic epitope and a peptide carrier, wherein said antigenic epitope is coupled to, or admixed with, said peptide carrier.

In an embodiment, the peptide carrier is selected from the group consisting of keyhole limpet hemocyanin (KLH) and ovalbumin. The coupling can, for instance, be a covalent coupling or a disulphide bridge. In one embodiment keyhole limpet hemocyanin is a preferred peptide carrier.

In some embodiments, an antigenic epitope may be provided with a cysteine residue at its N- or C-terminus (preferably N-terminus). Such a cysteine residue may facilitate coupling of the antigenic epitope to a peptide carrier (e.g. KLH).

Yet another aspect of the embodiments relates to the use of an antigenic epitope and/or a conjugate according to above for production of an antibody that specifically binds to a protein.

Still another aspect of the embodiments relates to a method for production of an antibody that specifically binds to a protein. The method comprises raising an antibody against an antigenic epitope and/or a conjugate according to above and isolating the antibody. Isolating the antibody may comprise isolating the antibody from the cell (e.g. host cell) in which it was generated or produced and/or from growth medium/supernatant.

In a particular embodiment, the method comprises exposing the protein to limited or restricted proteolysis by contacting the protein to at least one protease to form at least one digested, deconstructed or truncated version of the protein and at least one surface-exposed peptide. The method also comprises probing the at least one digested, deconstructed or truncated version of the protein in a functional assay that tests, checks or verifies at least one biological function of the protein. The method further comprises identifying an antigenic epitope in the protein as a surface-exposed peptide among the at least one surface-exposed peptide and present in a region of the protein involved in exerting the biological function of the protein as determined based on the functional assay. The method further comprises raising an antibody against the antigenic epitope and isolating the antibody.

Raising the antibody against the antigenic epitope can be performed according techniques known in the art including, for instance, the hybridoma technique, the phage-display technology, etc. as previously described herein.

A further aspect of the embodiments relates to an antibody against an antigenic epitope and/or a conjugate according to above. The antibody specifically binds to the protein.

Thus, in one aspect, the present invention provides an antibody generated by (or produced by) a method of the present invention.

In another aspect, the present invention provides an antibody against an antigenic epitope of the invention. Alternatively viewed, the present invention provides an antibody which binds to an antigenic epitope of the invention. Alternatively viewed, the present invention provides an antibody which specifically binds to an antigenic epitope of the invention.

By way of example, the invention provides an antibody against an antigenic epitope comprising (or consisting of) an amino acid sequence selected from the group consisting of LLSQDSVAASTEKTLRLYDRRS (SEQ ID NO:5) and GRHWKNFALVPLLRE (SEQ ID NO:6). In one embodiment, an antibody against an antigenic epitope comprising (or consisting of) the amino acid sequence LLSQDSVAASTEKTLRLYDRRS (SEQ ID NO:5) is an antagonistic (inhibitory) antibody against TRPV1, preferably having one or more of the functional properties described in the Example section for the antibody OTV1. This epitope corresponds to an amino acid sequence that is located in the N-terminal intracellular domain of TRPV1. In one embodiment, an antibody against an antigenic epitope comprising (or consisting of) the amino acid sequence GRHWKNFALVPLLRE (SEQ ID NO:6) is an agonistic antibody against TRPV1, preferably having one or more of the functional properties described in the Example section for the antibody OTV2. This epitope corresponds to an amino acid sequence that is located in the C-terminal intracellular domain of TRPV1.

In some embodiments, an antibody may be against an intracellular TRPV1 epitope (or domain). In some such embodiments, an antibody may be an antagonistic (inhibitory) antibody against an intracellular TRPV1 epitope (or domain). In other such embodiments, an antibody may be an agonistic antibody against an intracellular TRPV1 epitope (or domain).

In an embodiment, the binding of the antibody to the protein results in lack of or significantly altered biological function of the protein.

Thus, the antibody may be a functional antibody, e.g. an agonistic antibody or an antagonistic antibody (e.g. an antagonistic or agonistic antibody against TRPV1 or TRPV2). An antagonistic antibody is capable of binding to a protein and inhibiting or reducing a function of the protein. An agonistic antibody is capable of binding to a protein and potentiating or increasing a function of the protein. In the case of TRPV1 or TRPV2 (or any other ion channel) the function concerned may be ion transport activity. For example, the ability of an antibody to block (reduce) or enhance (increase) capsaicin or calmodulin binding may be assessed. Antibodies with such capabilities form preferred embodiments of the invention.

A related aspect of the embodiments defines an antibody according to above for use as a medicament.

The antibody against the antigenic epitope and/or conjugate may be obtained by immunizing an animal with one or more antigenic epitopes and/or one or more conjugates according to the embodiments. The immunized animal may be selected from the group comprising humans, mice, rats, rabbits, sheep, non-human primates, goat, horse and poultry.

The antibody according to the embodiments may also be obtained by in vitro immunization methods using one or more antigenic epitopes and/or one or more conjugates according to the embodiments.

The antibody according to the invention may be a polyclonal antibody or a monoclonal antibody.

The antibody may be a ligand, one or more fragments of an antibody, such as a Fab (Fragment Antigen Binding) fragment, a F(ab)'2 fragment (a fragment containing two Fab), a ScFv fragment (single-chain variable fragment), a diabody, a tetrabody, or an intact antibody.

An antibody of the invention is typically capable of binding (e.g. specifically binding) to the full-length version of the protein against which it is directed, for example the full-length version of the protein in its native form (e.g. in or on cells).

In some embodiments, the antibody is an antibody against one of the proteins (or types of proteins) described elsewhere herein.

Antibodies and antigenic epitopes may be isolated or purified. The term "isolated" or "purified" as used in this context refers to such molecules when isolated from, purified from, or substantially free of their natural environment, e.g., isolated from or purified from an organism (if indeed they occur naturally), or refers to such molecules when produced by a technical process, i.e., includes recombinant and synthetically produced molecules. Thus, the term "isolated" or "purified" typically refers to an antibody or antigenic epitope substantially free of cellular material or other proteins from the source from which it is derived. In some embodiments, such isolated or purified molecules are substantially free of culture medium when produced by recombinant techniques, or chemical precursors or other chemicals when chemically synthesized.

The functional effect of antibodies generated by the present invention on their target protein may be assessed, and a skilled person will readily be able to determine suitable assays to use, e.g. based on the nature of the target protein. For example, if the antibody is an antibody against TRPV1 (or any other ion channel), the functional effect of the antibody may be assessed e.g. using the electrophysiology and/or YO-PRO uptake assay described in Example 2 herein.

The methods of the invention can be used to generate an antibody which can then be isolated, produced or manufactured for various downstream uses. Thus, a further aspect of the present invention provides a method of producing or manufacturing and/or isolating an antibody.

When one or more antibodies have been generated, produced, selected, identified, isolated and/or purified using the methods of the invention, these antibodies, or a component, fragment, variant, or derivative thereof may be manufactured and if desired formulated with at least one pharmaceutically acceptable carrier or excipient. Such manufactured molecules, or components, fragments, variants, or derivatives thereof, are also encompassed by the present invention. Alternatively, these molecules may take the form of nucleic acids encoding said antibodies, which nucleic acids may in turn be incorporated into an appropriate expression vector and/or be contained in a suitable host cell. Thus, nucleic acid molecules encoding said antibodies, or expression vectors containing said nucleic acid molecules form further aspects of the invention.

Once a particular antibody, or a component, fragment, variant, or derivative thereof, has been generated or produced in accordance with the present invention, the expression vector encoding the antibody can readily be used (or adapted for use) to produce sufficient quantities of the molecule by expression in appropriate host cells or systems and isolating the antibodies from the host cell or system or from the growth medium or supernatant thereof, as appropriate. For polyclonal antibodies, antibodies may be isolated or purified from the serum of an immunized animal.

Thus, a yet further aspect of the invention provides a method of producing or manufacturing an antibody comprising the steps of generating or producing an antibody according to the methods of the invention as described above, manufacturing or producing said antibody, or a component, fragment, variant, or derivative thereof and optionally formulating said manufactured antibody with at least one pharmaceutically acceptable carrier or excipient.

Said variants or derivatives of an antibody include peptoid equivalents, molecules with a non-peptidic synthetic backbone and polypeptides related to or derived from the original identified polypeptide wherein the amino acid sequence has been modified by single or multiple amino acid substitutions, additions and/or deletions which may alternatively or additionally include the substitution with or addition of amino acids which have been chemically modified, e.g. by deglycosylation or glycosylation. Conveniently, such derivatives or variants may have at least 60, 70, 80, 90, 95 or 99% sequence identity to the original polypeptide from which they are derived.

As the invention relates to the generation of antibodies, said variants or derivatives further include the conversion of one format of antibody molecule into another format (e.g. conversion from Fab to scFv or vice versa, or the conversion between any format of antibody molecules described elsewhere herein, e.g. the conversion to any other type of antibody fragment as described herein), or the conversion of an antibody molecule to a particular class of antibody molecule (e.g. the conversion of an antibody molecule to IgG or a subclass thereof, e.g. IgG1 or IgG3, which are particularly suitable for therapeutic antibodies) or the humanization or the formation of a chimeric version of any antibody.

Said variants or derivatives further include the association of antibodies with further functional components which may for example be useful in the downstream applications of said antibodies. For example the antibodies may be associated with components which target them to a particular site in the body, or with detectable moieties useful for example in imaging or other diagnostic applications, or with a payload such as a radio-isotope, toxin or chemotherapeutic agent in the form of an immunoconjugate.

Clearly, the main requirement for such components, fragments, variants, or derivative binding partner molecules or target entities is that they retain their original functional activity in terms of binding ability or have improved functional activity.

The antibody molecules generated or produced or manufactured using the methods of the present invention may be used in any methods where antibodies specific to a target entity (for example antibodies specific to a particular antigen) are required. Thus, the antibodies can be used as molecular tools and a further aspect of the invention provides a reagent which comprises such antibodies as defined herein. In addition, such molecules can be used for in vivo therapeutic or prophylactic applications, in vivo or in vitro diagnostic or imaging applications, or in vitro assays.

Other features and advantages of the present invention are apparent from the examples below. The provided examples illustrate different components and methodology useful in practicing the present invention. The examples do not limit the claimed invention. Based on the present disclosure the skilled artisan can identify and employ other components and methodology useful for practicing the present invention.

EXAMPLES

Example 1

In this example we describe a successful approach where we have discovered and developed a polyclonal antibody-OTV1-acting on the intracellular side of the human TRPV1 ion channel, based on the proposed invention and including methods. The antibody is pharmacologically active, and displays strong inhibitory action on the protein when stimulated with the agonist capsaicin. To the best of our knowledge, this is the first time an inhibitory antibody targeting the intracellular domains of TRPV1 is discovered. This proves that the concept has a high probability of working, and that even better and optimized antibodies could be identified if the starting matrix of epitopes originating from much richer multiprotease datasets would be available. The antibody was selected out of a number of hits from limited proteolysis and bioinformatic analyses. The antibody was the first selected and it showed strong evidence of efficacy. This is a significant advancement, and complimentary to current antibody identification efforts since no screening step is needed as it directly results in unique epitopes that can be targeted by a pharmacologically active antibody.

Figure 3:
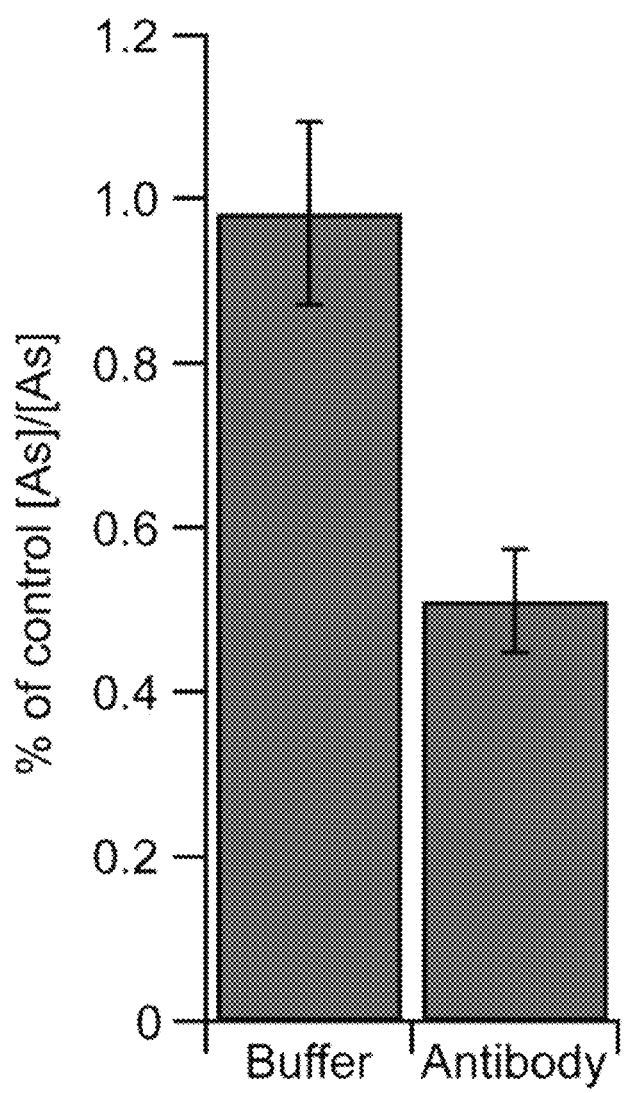

The targeted epitope region was chosen based on limited digestion of the target protein using optimized protocols in the LPI microfluidic platform, and was further optimized. A polyclonal antibody was generated by modifying the target peptide epitope with a cysteine-residue and link it to Keyhole Limpet Hemocyanin (KLH). The production of the specific antibody was performed by immunization of specific pathogen free (SPF) rabbits following injection of KLH with linked specific peptide. The antibodies were purified and subjected to an ELISA test according to standard protocols. An antibody titer against the linear epitope was performed with ELISA, resulting in a concentration of 0.25 µg/ml. The efficacy of the antibody against native TRPV1 was studied with inside-out patch clamp, where the intracellular side of TRPV1 could be exposed to antibody solution. Inside out recordings were performed using a microfluidic device for patch clamp recordings (Dynaflow, Cellectricon AB, Goteborg, Sweden). Current amplitudes were measured by exposing patches, containing several ion channels, to capsaicin, with and without antibody. Controls were exposed to 1 µM capsaicin for 30 s followed by buffer for 70 s and then again 1 µM capsaicin for 30 s. Antibody treated patches were exposed to 1 µM capsaicin for 30 s followed by 0.14 mg/ml antibody for 70 s and then 1 µM capsaicin together with 0.14 mg/ml antibody for 30 s. For all measurements, activity with antibody was compared to activity after exposure to only buffer, in order to exclude any effects of desensitization or potentiation. Current-time integrated areas were calculated and the ratio between the integrated areas for the second and first current were calculated and compared between treatments. A 50% decrease in current response were observed for cells treated with antibody compared to only buffer (FIG. 3). Statistical significance was calculated with Student's T-test ($p>0.05$).

Example 2

The therapeutic mAb market is rapidly growing and is predicted to be worth about 125 billion USD in 2020. Novel mAbs are continuously reaching regulatory approvals, and presently, immunobased mAbs such as PD1 inhibitors, are much discussed since they are considerably improving the outcomes in certain types of difficult metastatic cancers. However, the discovery of novel antibodies for therapeutic purposes relies largely on screening, and is done blindly. The focus is on affinity, and a subset of antibodies showing good binding characteristics are subsequently tested for biological effects. The specifics around the binding interaction, antigen determinants, and mechanisms of action remain unknown.

We present a method that selects antigen epitopes based on a limited proteolytic kinetic challenge using a microfluidics approach and mass spectrometry. The proteolytic step is done so slowly that, after a protease challenge, the antigen tears off a single or a few peptides at the time. First coming peptides are easily accessible to a pAb or mAb, and are therefore favored over late coming peptides residing in regions of the protein that would be more difficult to reach. These peptides are then rank-ordered and cross-correlated for sequence-based functional significance using curated bioinformatic data. Highly-ranked peptides, coming off the target protein quickly, also having functional significance are used for epitope development, immunization and subsequent antibody generation. Also, the truncated proteins can be used for pharmacological testing. This method relies on sequence-based information, and is a pharmacological, mechanism-of-action based approach to antibody discovery, and can be used both for intracellular, circulating, and extracellular targets. We have used this method to develop two antibodies, one activating-addressing a calmodulin-binding sequence, and one inhibiting, addressing the capsaicin binding site in the N-terminus of the intracellular region of the human TRPV1 ion channel.

Two important parameters when developing therapeutic antibodies are binding affinity and biological efficacy. Antibodies are large proteins of approximately 150 kDa and binds primarily to antigenic sites located on the protein surface. Localization of amino acids in vicinity of the surface of native protein structures can guide the identification and prediction of these sites. We used limited proteolysis to probe surface-exposure and flexibility of a protein. It is a method where the activity of a protease is limited by control of the temperature, the concentration and/or the digestion time. Only flexible regions that can unfold locally and accommodate the protease, surface-exposed regions and regions with few local interactions such as hydrogen bonds and disulphide bridges, will be digested under such conditions. We used several proteases in tandem in order to maximize retrieval of structural information. Regions that are easily digested by several proteases should be located in the most exposed, most accessible regions of the protein and be of high suitability for further antibody development. Regions that are only digested by a single protease is likely located in a hidden region of the protein and less accessible. The physiochemical properties of the protease, able to reach and digest these regions, could potentially guide antibody development in such cases. We ranked digested peptides based on their ease of digestion depending on which parameters were used to limit the proteolysis. That could be the time point they were digested, which concentration or temperature that was used. Peptides digested from each protease were then correlated with each other, in order to find those peptides that originate from the most accessible regions of the protein.

During conventional antibody development, biological efficacy is generally tested after positive binding is confirmed between antibody and antigen. We believe that antibody development will benefit from an early mechanistic driven approach by focusing the immunization on accessible sites in or in vicinity of a biological active site rather than creating antibodies targeting all possible antigenic sites. This minimizes the screening procedures as well as the risk of optimizing antibodies that have a high binding affinity to regions distant from a biological active site. We wanted to find accessible epitopes that also had a functional importance for the target protein. This was done by comparing the ranked peptides from limited proteolysis with bioinformatics data.

We demonstrated our mechanism driven approach using the human TRPV1 ion channel as a model protein. TRPV1 is an ion channel sensitive to noxious stimuli such as low pH, high temperatures (T>42° C.), capsaicin, and several inflammatory mediators. The TRPV1 ion channel is mainly located in nociceptive neurons of the peripheral nervous system where it is arranged in a tetrameric conformation. Each of its four monomers consist of six transmembrane region with both the N- and C-termini facing the intracellular side of the plasma membrane. The pore region is comprised of the 5th and 6th transmembrane region. The intracellular part of TRPV1 holds many regulatory regions important for heat activation, sensitization and desensitization.

Epitope Generation

Figure 4:
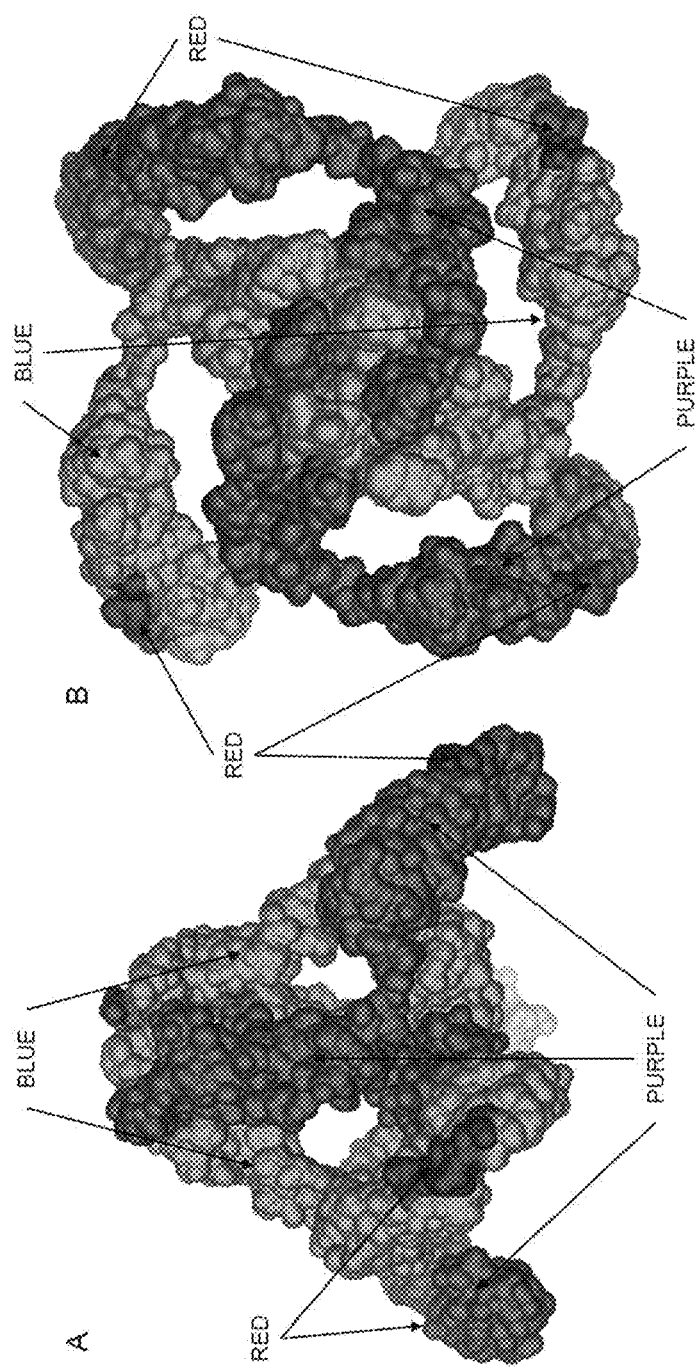
Figure 5:
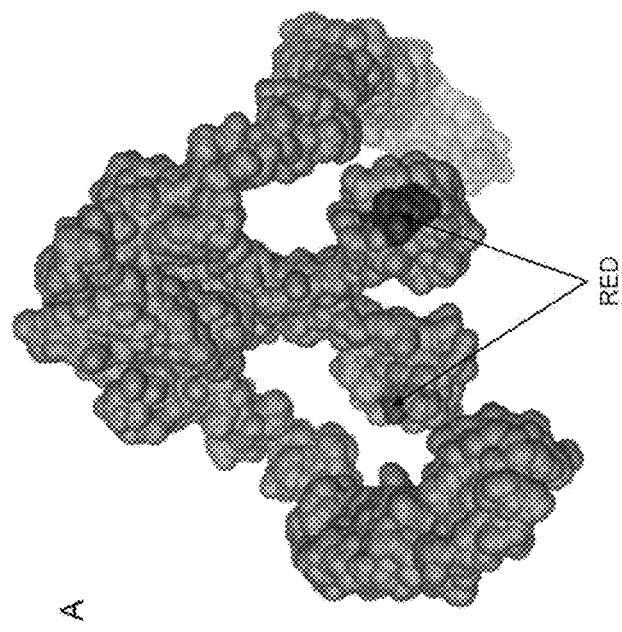
Figure 5:
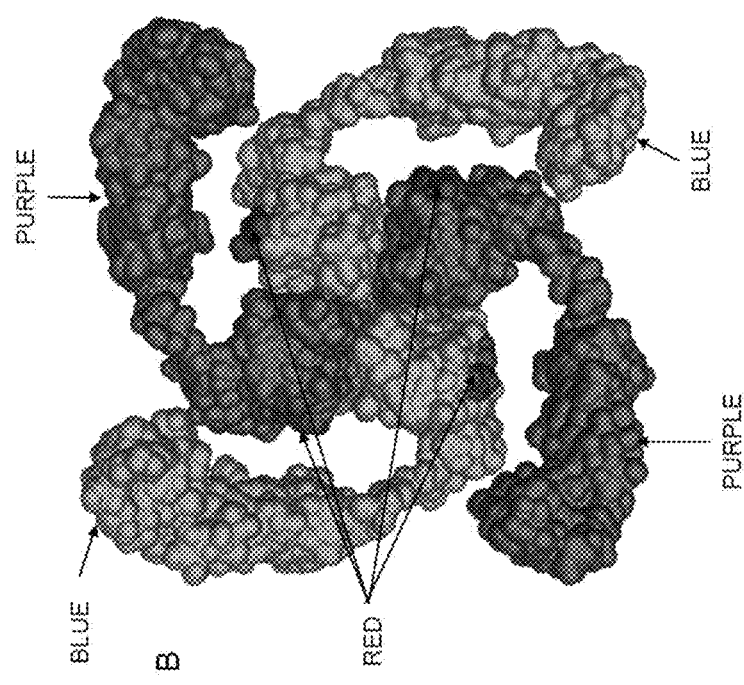

Proteoliposomes containing TRPV1 were derived from CHO cells and subjected to limited proteolysis within the LPI flow cell, using trypsin and Asp-N separately. The activity of the proteases were limited to the extent that only a few peptides were digested, by the use of room temperature and low concentrations. Digested peptides were then detected with liquid chromatography with tandem mass spectrometry (LC-MS/MS). Three peptides were detected after proteolysis with trypsin and one peptide after proteolysis with Asp-N. The peptides were compared to known functional data and several of the peptides correlated with functionally important regions as listed in Table 1. Two peptides were chosen for further antibody development, aa96-117 and aa785-799, named OTV1 and OTV2 respectively. Visualization of the epitopes within the TRPV1 structure can be seen in FIGS. 4 and 5. The peptide sequence for OTV1 includes arg115 (arg114 for rTRPV1) which have been shown to be important for activation with capsaicin or protons. Both proteases digested regions in the vicinity of this amino acid, increasing the possibility that this is an exposed region in the tertiary protein structure. The peptide sequence for OTV2 include the calmodulin binding site aa786-aa798 (aa785-aa797 for rTRPV1) and was digested by trypsin only. There are no digestion sites for Asp-N, which cleaves on the N-terminal side of Asp and Cys, in that part of TRPV1. Synthetic peptides of aa96-117 and aa785-799 were linked to limpet hemocyanin (KLH) and further used to produce polyclonal antibodies by immunization of rabbits following injection of the KLH linked peptides. The produced antibodies show tendencies to aggregate during freezing and with time in solution. Freshly thawed antibodies were, as a result, tip-sonicated prior to use, and all experiments were performed within 30 minutes of tip-sonication.

TABLE 1

Peptides digested with Asp-N and trypsin and their biological relevance

| Asp-N | | | Trypsin | | | |
|---|---|---|---|---|---|---|
| Sequence | Start | Stop | Sequence | Start | Stop | Interaction |
| DSVAASTEKTLRLY (SEQ ID NO: 49) | 100 | 113 | LLSQDSVAASTEK (SEQ ID NO: 2) | 96 | 108 | Capsaicin |
| | | | NFALVPLLR (SEQ ID NO: 42) | 790 | 798 | Calmodulin |
| | | | QSAQPEEVYLR (SEQ ID NO: 45) | 806 | 816 | |

Immunocytochemistry

Figure 6:
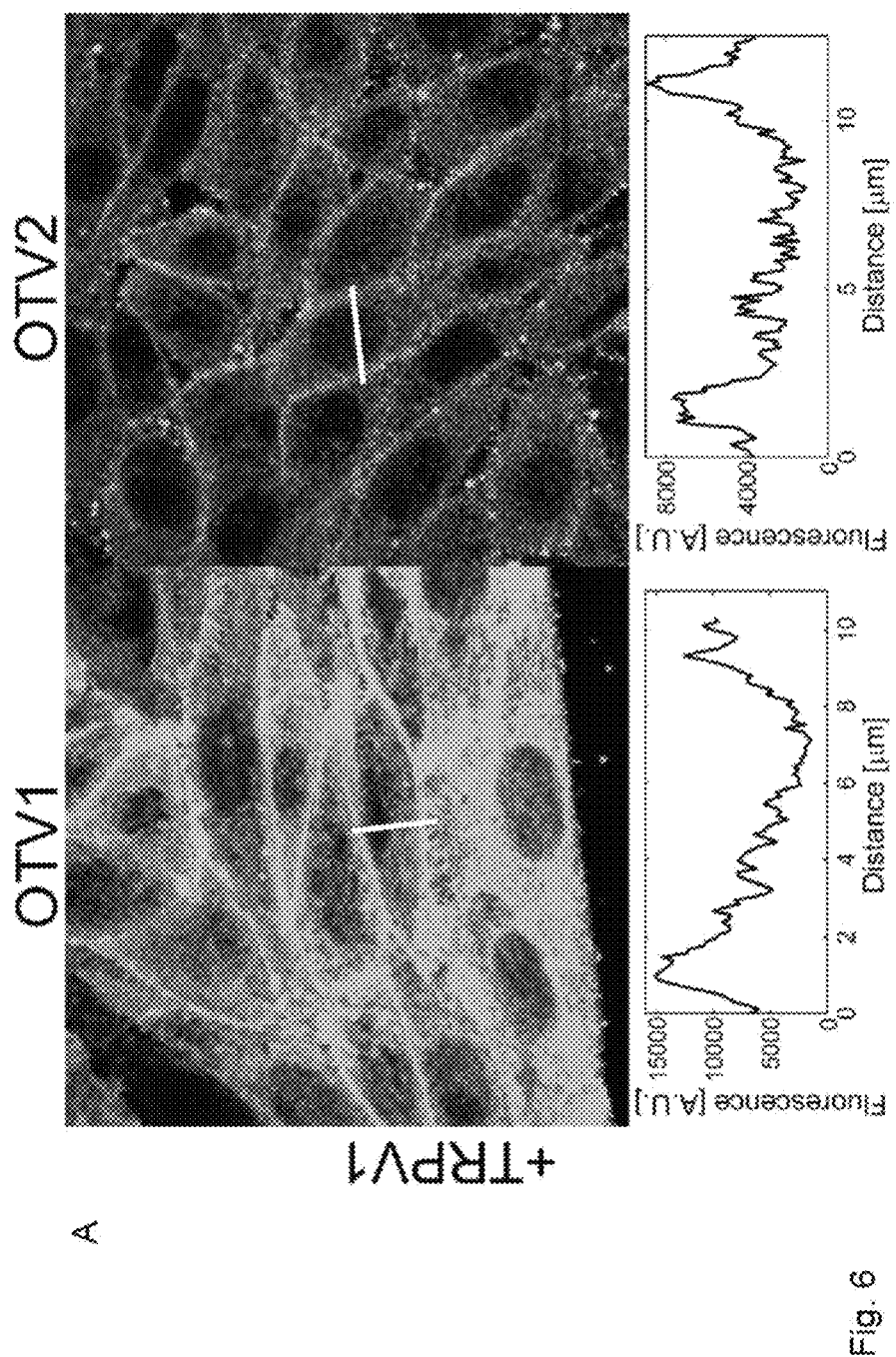
Figure 6:
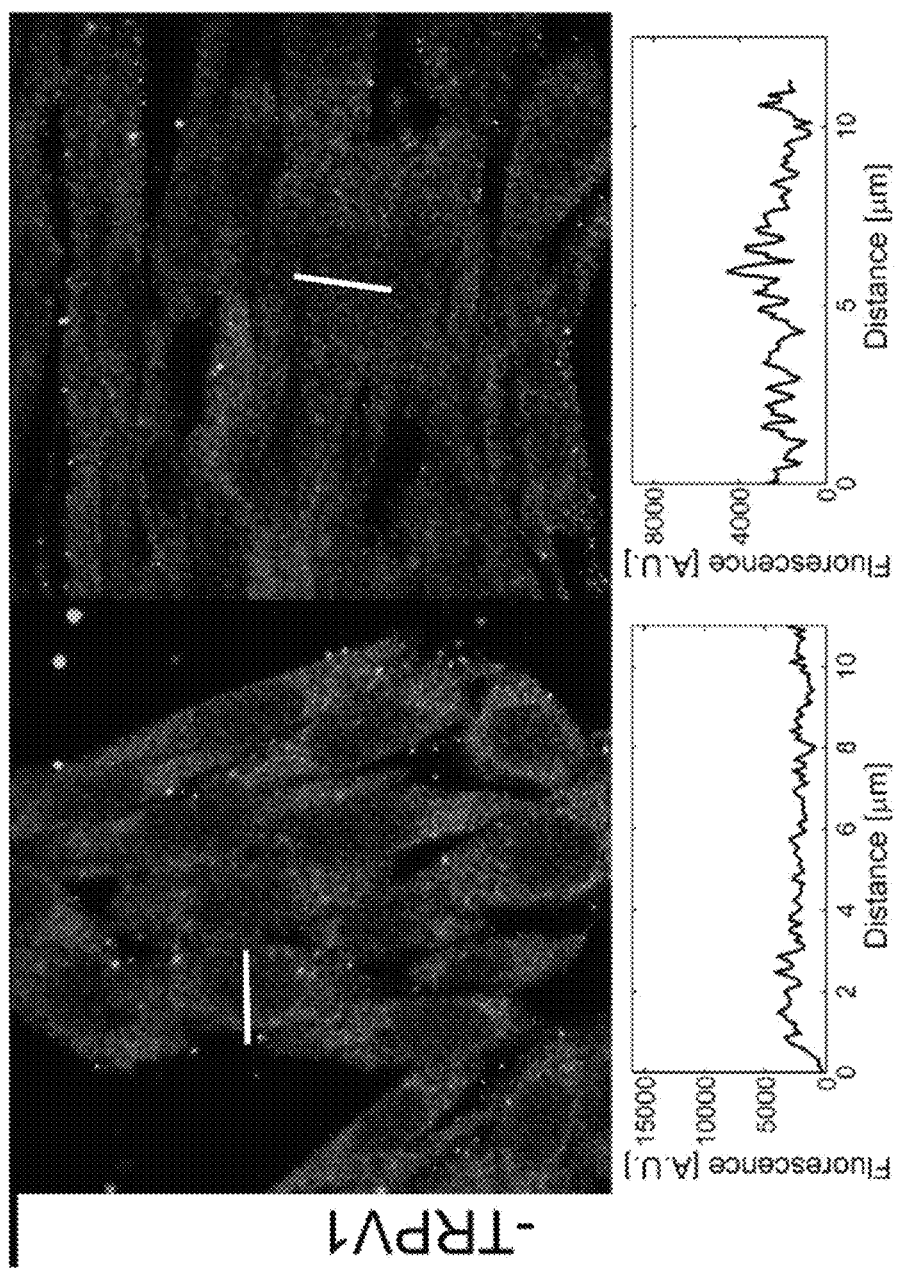

Immunocytochemistry was performed in order to visualize the antibody distribution within TRPV1 expressing CHO cells (FIG. 6). Non-induced cells served as a control for unspecific binding. Cells were fixed and stained with either OTV1 or OTV2 followed by a goat antirabbit Alexa 488 secondary antibody. A clear staining in the plasma membrane that was only visible in induced cells, was observed for both OTV1 and OTV2. Nonspecific binding of the secondary antibody was negligible (data not shown).

Electrophysiology

Figure 7:
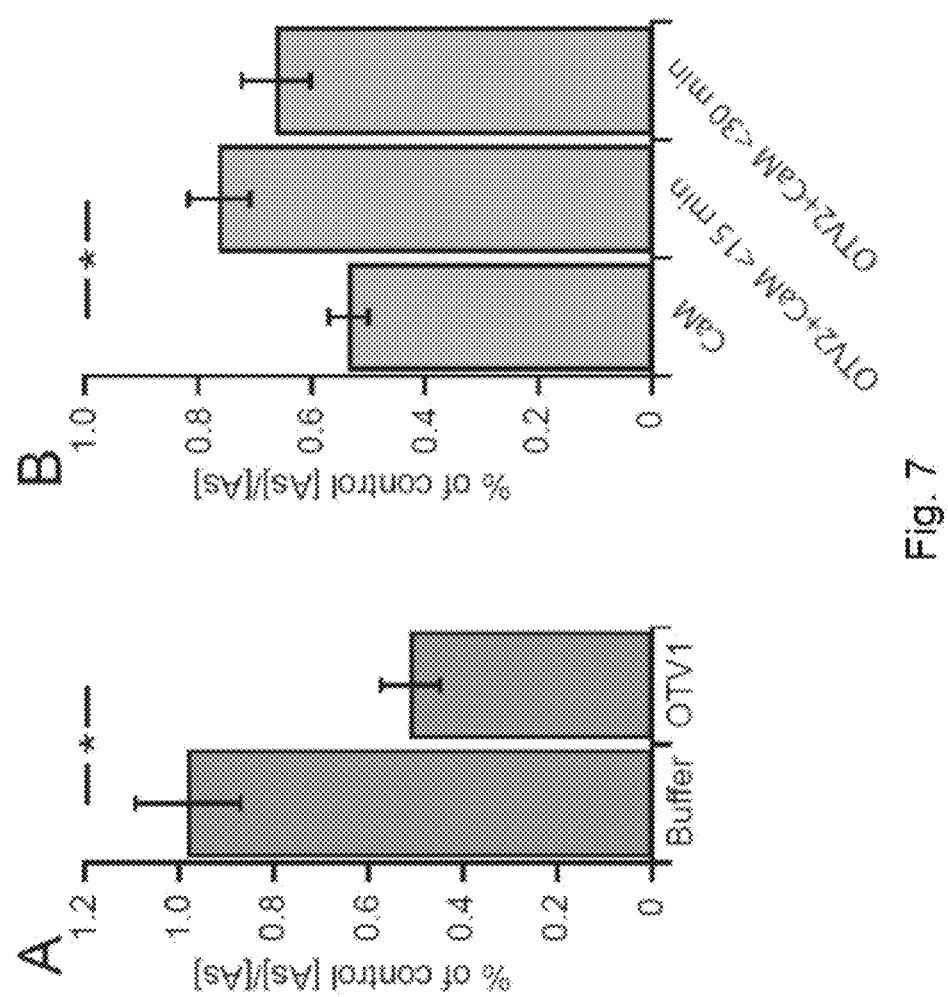

The functional effect of OTV1 on capsaicin induced TRPV1 activity as well as the effect of OTV2 on calmodulin/$Ca^{2+}$ dependent desensitization was evaluated using inside-out patch clamp recordings. Membrane patches, containing several ion channels, were excised from CHO cells, enabling antibody exposure to the intracellular region of TRPV1. For OTV1, TRPV1 was activated with capsaicin, then treated with OTV1, followed by activation with capsaicin in the presence of OTV1. Controls were activated with capsaicin, treated with buffer and activated with capsaicin again. A 50% decrease in capsaicin mediated currents was observed when comparing treatment with OTV1 to treatment with only buffer (FIG. 7). OTV2 was tested for its capability to interfere with calmodulin/$Ca^{2+}$ dependent desensitization. TRPV1 was activated with capsaicin, then treated with calmodulin, $Ca^{2+}$ and OTV2, followed by activation with capsaicin in the presence of calmodulin, $Ca^{2+}$ and OTV2. Controls were activated with capsaicin, treated with calmodulin and $Ca^{2+}$ and activated with capsaicin in the presence of calmodulin and $Ca^{2+}$. Calmodulin desensitize TRPV1 in the presence of calcium. Treatment with OTV2 reduced this effect with 45% (FIG. 7).

TRPV1 Mediated YO-PRO Uptake Assay

Figure 8:
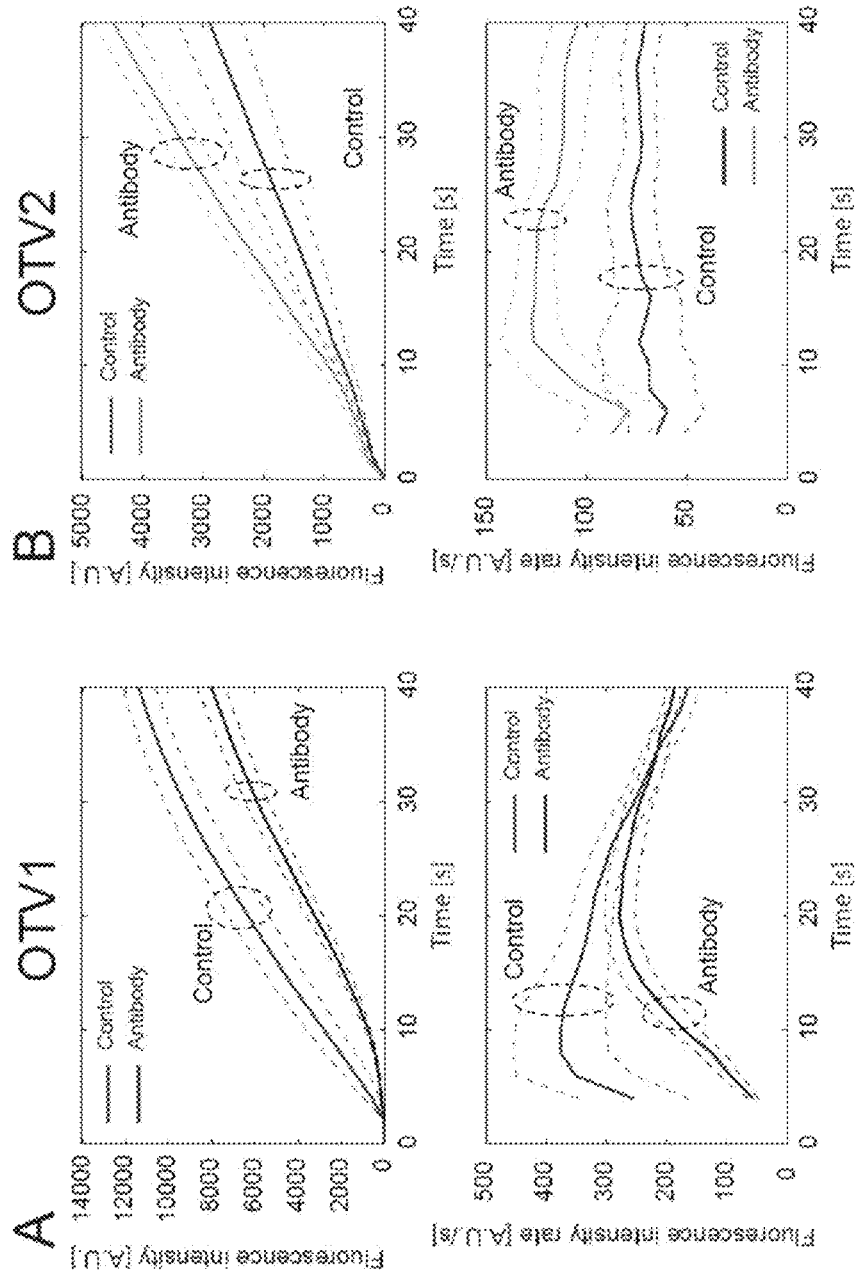
Figure 9:
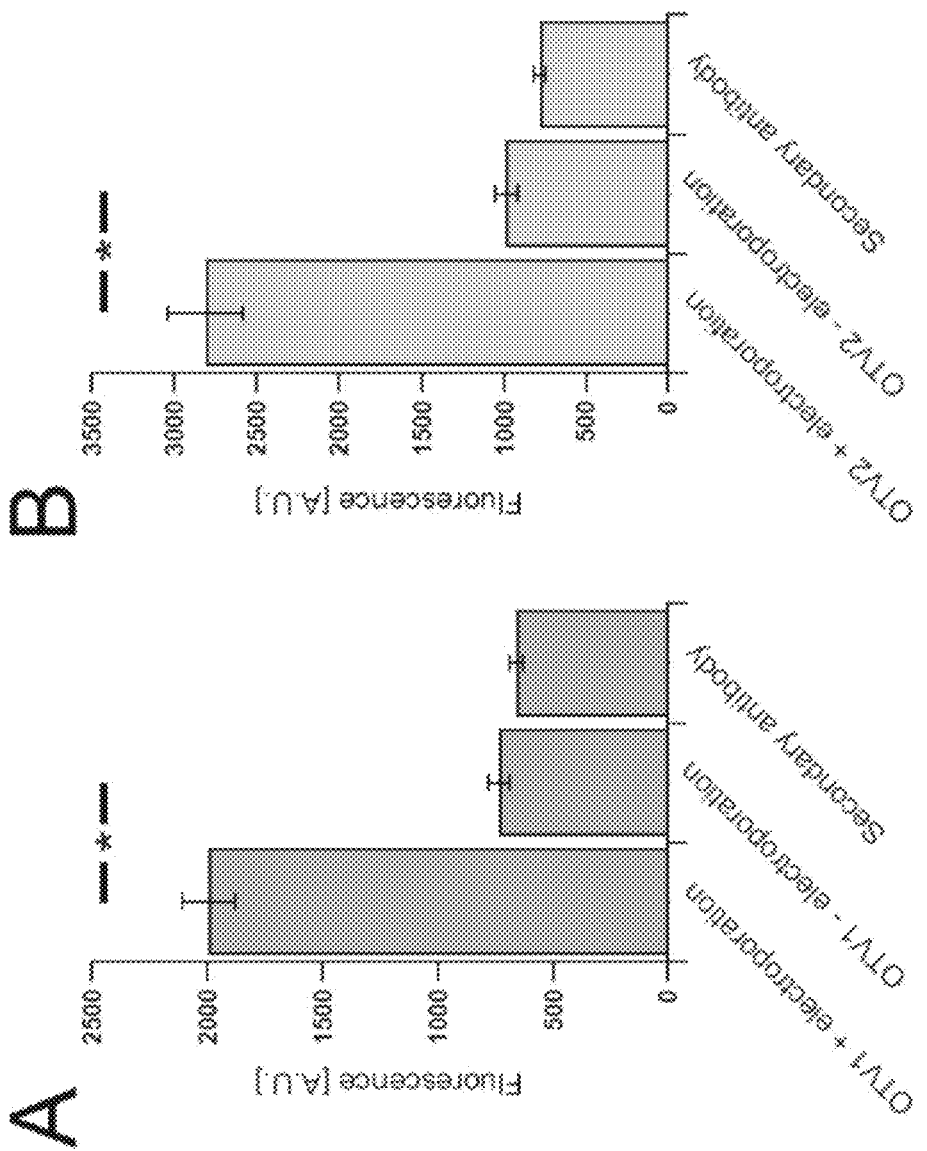

The efficacies of the antibodies within whole cells were tested using electroporation as a delivery method, followed by measurement of TRPV1 mediated YO-PRO uptake with laser scanning confocal microscopy. Cells were electroporated using a Neon transfection system (Life Technologies) in the presence of either OTV1, OTV2 or buffer. Cells electroporated with OTV1 or buffer were subjected to capsaicin and YO-PRO in PBS containing a calcium chelator. The intracellular increase in fluorescence due to TRPV1 mediated YO-PRO uptake was subsequently monitored. A 60% decrease in uptake rate for OTV1 treated cells could be observed during the initial 12 s of activation and the highest uptake rate for OTV1 treated cells were observed after 20 s compared to 8 s for the control (FIG. 8). Cells electroporated with OTV2 or buffer were subjected to capsaicin and YO-PRO in PBS containing calcium, relaying on desensitization through endogenous calmodulin triggered by the applied calcium. An 80% increase in uptake rate could be observed after 15 s of activation for OTV2 treated cells. Internalization of antibodies with electroporation was validated using immunocytochemistry (FIG. 9).

We have developed a microfluidic method for antibody generation that locates exposed and accessible antigenic sites in and/or in the vicinity of functionally important regions of a target protein. Accessible regions are probed, using kinetically restricted proteolysis, within the LPI flow cell. The target protein is held in its native state while the complexity of its environment can be carefully controlled, e.g. by allowing for co-factors to be present. This yields a better understanding of the accessibility of antigenic sites compared to binding assays using purified proteins. The method is well suited for transmembrane targets that otherwise are difficult to purify and use in binding assays without the need of detergents. Both intracellular and extracellular domains can be targeted using this approach.

Knowledge of the location of the antigenic site as well as its biological function is of great importance for prediction and evaluation of unspecific binding and cross-reactivity with other proteins. Epitopes located in very conserved regions could be excluded from the analysis of potential epitope candidates in order to minimize cross-reactivity.

The antibodies developed herein are polyclonals although not resulting from immunization with an entire protein. Our method is compatible with conventional protocols for production of monoclonal antibodies using hybridomas and subsequent screening procedures. Using polyclonal antibodies as a first step to experimentally validate biological efficacy for several promising epitope candidates followed by production of monoclonal antibodies using the best epitope/epitopes, and screening procedures for high binding affinity, combines the best of two worlds.

Verification of Antibody Internalization

The internalization of antibodies with electroporation was validated 24 hours after electroporation, with immunocytochemistry. Cells were electroporated in the presence of 0.14 mg/ml OTV1 or 0.27 mg/ml OTV2 in PBS. Electroporated cells were then cultured for 24 hours in glass bottom dishes (Willco wells). Two different controls were made. One set that weren't electroporated but were otherwise treated equally and subjected to the same antibody solutions, and another set that weren't subjected to OTV1 and OTV2. The latter were used to quantify unspecific binding of the secondary antibody. After 24 hours of cultivation, cells were washed carefully with PBS to remove any residual antibodies which could otherwise enter the cells during fixation. Cells were then fixed and permeabilized using the Image-iT® Fixation/permeabilization kit (Invitrogen). Fixed and permeabilized cells were incubated with a goat anti-rabbit Alexa 488 secondary antibody (Invitrogen) for 30 min in room temperature. Cells were visualized after a final washing step and fluorescence intensities were compared between electroporated cells, non electroporated cells and cells subjected to only secondary antibodies (FIG. 9). A clear difference in intensity values between electroporated and non electroporated cells was observed. Statistical analysis was performed with Students T-test and p<0.05 was considered as statistically significant. Low levels of primary antibodies were found in non electroporated cells which is likely residual antibodies that entered during fixation and permeabilization.

We herein presented a method for generation of high affinity, biologically active antibodies utilizing a combination of microfluidics and limited proteolysis. The method was validated using the human TRPV1 ion channel and two antibodies were developed. Both antibodies caused a predicted alteration in TRPV1 response based on the functional importance of their respective epitope region.

Materials and Methods

Chemicals

Cell culturing medium (DMEM/Ham's F12 with glutamine), fetal bovine serum, and Accutase were purchased from PAA. Zeocin, $Na_4BAPTA$, $K_4BAPTA$ and Goat anti rabbit Alexa 488 secondary antibody were purchased from Invitrogen. Sequencing grade modified trypsin and sequencing grade Asp-N were purchased from Promega. All other chemicals were purchased from Sigma. The following buffers were used: A: 300 mM NaCl, 10 mM Tris, pH 8.0, B: 20 mM $NH_4HCO_3$, pH 8.0. C: 140 mM NaCl, 5 mM KCl, 1 mM $MgCl_2$ 10 mM HEPES, 10 mM D-glucose, 10 mM $Na_4BAPTA$ pH 7.4, D: 140 mM NaCl, 2.7 mM KCl, 10 mM $Na_2HPO_4$, 10 mM $K_4BAPTA$ pH 7.2, E: 140 mM NaCl, 2.7 mM KCl, 10 mM $Na_2HPO_4$, pH 7.2. F: 140 mM NaCl, 2.7 mM KCl, 10 mM $Na_2HPO_4$, pH 7.4. G: 120 mM KCl, 2 mM $MgCl_2$, 10 mM HEPES, 10 mM $K_4BAPTA$ pH 8.0

Cell Culture

Adherent Chinese hamster ovary (CHO) cells with a tetracycline regulated expression system (T-REx) were cultivated in medium (DMEM/F12 with glutamine) supplemented with 10% fetal bovine serum, Zeocin (350 µg/ml), and Blasticidin (5 µg/ml) in culture flasks or culture dishes (Nunc) with and without glass slides. 18-24 hours before use, the cells were incubated in medium (DMEM/F12 with glutamine) supplemented with 10% fetal bovine serum and Doxycycline (1 µg/ml) in order to induce expression of human TRPV1. The cell line was routinely tested for *Mycoplasma* infection.

Proteoliposome Preparation

Proteoliposomes were prepared as previously elsewhere [1] in buffer A. Each proteoliposome preparation originated from several different culture flasks.

Digestion Protocols

Single digestions within the flow cell were conducted as described elsewhere [1]. 5 µg/ml Trypsin and 5 µg/ml Asp-N was dissolved in buffer G and B, respectively. Digestion within the flow cell with each protease was performed in room temperature for 5 min. Further digestion in the elutes was inhibited by addition of formic acid to a final concentration of 12%.

Liquid Chromatography with Tandem Mass Spectrometry

Peptide samples from digestions of CHO-proteoliposomes were analyzed at the Proteomics Core Facility at Gothenburg University, Goteborg, Sweden, as previously described [1]. All tandem mass spectra were searched by MASCOT (Matrix Science, London, UK) against UniProtKB release 2013_04, (Human, [*Homo sapiens*]) for digestion with trypsin and release 2015_06 (Human, [*Homo sapiens*]) for digestion with Asp-N. Thermo Proteome Discoverer v. 1.3 (Thermo Scientific) was used to validate MS/MS based peptide and protein identifications. A false discovery rate of 0.01 on peptide level were used and determined by searching a reversed database.

Antibody Development

Synthetic peptides of aa96-117 and aa785-799 with reference to the amino acid sequence of hTRPV1, including an additional cysteine residue on the N-terminal side, were synthesized and purified. The peptides were then linked by the cysteine residue to keyhole limpet hemocyanin (KLH) and then used to produce polyclonal antibodies by immunization of specific pathogen-free (SPF) rabbits following injection of the KLH linked peptides. The antibodies were purified and subjected to an ELISA test. Generation of both synthetic peptides and polyclonal antibodies were performed by Innovagen AB (Lund, Sweden).

Antibodies were used freshly thawed and within 30 min of tip-sonication. The antibodies were sonicated at 14% amplitude three times, interspaced with 1 min of resting, using a Vibra Cell VCX 600 from Sonics & Materials Inc. (Newtown, Conn., USA). Total sonication time were 40 s with 0.5 s pulse time and 0.5 s resting time in order to reduce heating by the probe.

Electrophysiology

Inside-out recordings were performed using a microfluidic device for patch clamp recordings (Dynaflow, Cellectricon AB, Goteborg, Sweden) together with a HEKA EPC10 (Heka Elektronik, Germany) patch clamp amplifier. Bath and pipette solutions contained buffer C. The patches were clamped at +60 mV and the current signals were recorded with a sampling frequency of 20 kHz and low pass filtered at 5 kHz.

For OTV1, current amplitudes were measured by exposing patches, containing several ion channels, to capsaicin, with and without antibody. Controls were exposed to 1 µM capsaicin in buffer D for 30 s, followed by buffer D for 70 s and then again 1 µM capsaicin in buffer D for 30 s. OTV1 treated patches were exposed to 1 µM capsaicin in buffer D for 30 s, followed by 0.14 mg/ml antibody in buffer D for 70 s and then 1 µM capsaicin together with 0.14 mg/ml antibody in buffer D for 30 s. For OTV2, current amplitudes were measured by exposing patches to capsaicin, with and without antibody and calmodulin/$Ca^{2+}$. Controls were exposed to 1 µM capsaicin in buffer E for 30 s, followed by exposure to 0.5 µM calmodulin and 50 µM $Ca^{2+}$ in buffer E for 70 s and then again 1 µM capsaicin in buffer E for 30 s. Antibody treated patches were exposed to 1 µM capsaicin in buffer E for 30 s, followed by 0.14 mg/ml antibody, 0.5 µM calmodulin and 50 µM $Ca^{2+}$ in buffer E for 70 s and then 1 µM capsaicin together with 0.14 mg/ml antibody, 0.5 µM calmodulin and 50 µM $Ca^{2+}$ in buffer E for 30 s. Measurements that shifted largely in seal resistance after treatment were excluded from further analysis.

Data Analysis Electrophysiology

For all measurements, activity after antibody treatment was compared to activity after exposure to only buffer, in order to exclude any effects of desensitization or potentiation resulting from recurring activations. For data containing current traces, current-time integrated areas were calculated using Fitmaster (HEKA Elektronik, Germany) and Matlab (Mathworks, Mass., USA) for each activation with capsaicin between application and removal for OTV1 and between full activation (after 10 s) and removal for OTV2. The ratio between the integrated areas for the second and first current were calculated and compared between treatments. For OTV2, data points were grouped into two categories (<15 min after tip sonication and <30 min after tip-sonication) due to a time dependent decrease of effect.

Statistical analysis was performed with one-way analysis of variance in combination with Dunnett's post-hoc test and Students T-test where applicable. $p<0.05$ was considered as statistically significant. Data is presented as mean±SEM.

Electroporation

Cytosolic antibody delivery was performed using a Neon transfection system (Life Technologies). Adherent CHO cells were detached using accutase and washed with buffer F. 105 cells were pelleted and resuspended in either buffer F, 0.14 mg/ml OTV1 in buffer F or 0.27 mg/ml OTV2 in buffer F. 10 µl of cell/antibody suspension were pipetted using a Neon pipette tip and subjected to electroporation in the system pipette station. A protocol optimized for antibody delivery [5] were used, where the cells were exposed to 1550 V during 10 ms and for 3 pulses. Electroporated cells were transferred to glass bottom dishes (Willco wells)

Imaging

Antibody localization through immunocytochemistry and TRPV1 mediated YO-PRO uptake was measured using region of interest (ROI) measurements from fluorescent micrographs. The micrographs were formed using a Thorlabs CLS system, equipped with a Galvo:Resonant scanner and High-Sensitivity GaAsP PMTs recording into ThorImageLS software (Thorlabs Inc, New Jersey, U.S.A.). The scanner unit was mounted onto a Leica DMIRB microscope equipped with an oil immersion 63×NA 1.47 Leica HCX PL APO objective. Fluorescence detection was measured from single cells, with an excitation at 488 nm using a Coherent Sapphire 488 LP laser (Coherent Inc., CA, U.S.A.) and emission was collected between 500-550 nm. ROI data was analyzed using Image J and Matlab (Mathworks, Mass., U.S.A.).

Immunocytochemistry

Cells were cultured on glass bottom dishes (Willco wells) and TRPV1 expression was induced in some dishes 18-24 hours before use. Both dishes containing cells expressing TRPV1 and non-induced cells were washed with buffer F then fixed and permeabilized using the Image-iT® Fixation/permeabilization kit (Invitrogen). Fixed and permeabilized cells were subjected to 25 µg/ml antibody in buffer F for 30 min at 37° C., then washed with buffer F followed by incubation with a goat anti-rabbit Alexa 488 secondary antibody for 30 min in room temperature. Cells were visualized after a final washing step and antibody distribution was compared between induced and non-induced cells.

TRPV1 Mediated YO-PRO Uptake

Glass bottom dishes containing 10 µl of electroporated cells were mounted to the microscope. Recording were initialized at a rate of 0.5 Hz. For OTV1 a 20 µl droplet containing capsaicin, YO-PRO and K4BAPTA in buffer F were carefully pipetted onto the electroporated cells in order to minimize detachment, causing a final concentration of 1 µM capsaicin, 1 µM YO-PRO and 10 mM $K_4$BAPTA. For OTV2 a 20 µl droplet containing capsaicin, YO-PRO and $Ca^{2+}$ in buffer F were similarly pipetted onto the electroporated cells causing a final concentration of 1 µM capsaicin, 1 µM YO-PRO and 50 µM $Ca^{2+}$.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible.

REFERENCES

1 Jansson, E. T.; et. al., *Anal. Chem.* 2012, 84: 5582-5588
2 International application no. WO 2006/068619
3 European patent application no. EP 2174908
4 Trkulja, C. L., et al., *J. Am. Chem. Soc.* 2014, 136: 14875-14882
5 Freund, G. et al., MAbs, 2013, 5: 518-522

Example 3

Peptide Identification by Limited Digestion and Mass Spectrometry of the Ion Channel TRPV1 Expressed in CHO Cells, Using Multiple Proteases This example describes the use of multiple proteases in parallel to identify protease-specific sets of peptides from TRPV1. The proteases used in this example are trypsin, Asp-N, Pepsin, Proteinase K and chymotrypsin. When compared with each other, the protease-specific sets of peptides can be overlapping, complementary, or unique. Different proteolytic activities were achieved by using different protease concentrations and in a few examples by using different incubation times.

Materials and Methods

Cell Culture

In brief, CHO cells were cultured according to Trkulja et al. (*J. Am. Chem. Soc.* 2014, 136, 14875-14882). In brief, adherent Chinese hamster ovary (CHO) cells with a tetracycline-regulated expression system (T-REx) were cultivated in medium (DMEM/F12 with glutamine) supplemented with 10% FBS, Zeocin (350 µg/mL), and Blasticidin (5 µg/mL) in T175 or T500 culture flasks (Nunc) or on glass dishes. Before use (18-24 h), the cells were incubated in medium (DMEM/F12 with glutamine) supplemented with 10% FBS and Doxycycline (1 µg/mL) in order to induce expression of human TRPV1. The cell line was routinely tested for *Mycoplasma* infection. After cell harvest, the cells were frozen and stored in −80 degrees. The cells were further processed as described below.

Cell Lysis and Homogenization

Cell suspensions were centrifuged for 580×g for 3 minutes. Supernatant were discarded and the tubes were filled carefully with 4 ml of ice-cold PBS. The cell pellets were re-suspended carefully and then the tubes were topped up to 14 ml with ice-cold PBS. Cell suspensions were again centrifuged for 580×g for 3 minutes, and the procedure was repeated two times.

The cell pellets (~800 µl volume) were re-suspended in approx. 6 ml of lysis buffer (10 mM $NaHCO_3$, pH 7.4) and kept on ice for 10 minutes.

The cells in lysis buffer were then transferred to a Dounce homogenizer (7 ml), one for each cell suspension. The cells were then subjected to homogenization with a tight pestle using 20 strokes. After homogenization, the lysed cells were subjected to a centrifugation step, 580×g for 3 minutes. The supernatant was collected and the cell pellets were discarded. The supernatants were subjected to a second centrifugation step, 580×g for 3 minutes and the cell pellet (small) was discarded.

The supernatants were pooled and transferred to a Beckman centrifuge tube (50 ml) and lysis buffer was added up to 20 ml. The supernatants were centrifuged for 10 minutes at 7300×g to remove mitochondria and cell debris. The supernatant was divided into two Falcon tubes (10 ml each) and frozen in a −80 freezer for further processing.

Ultracentrifugation

The supernatants were thawed on ice and transferred to two Beckman clear ultracentrifugation tubes (Beckman Coulter, item number 344057). The tubes were topped up with ice-cold buffer (10 mM Tris, 300 mM NaCl, pH 8) and carefully balanced prior centrifugation at 100,000×g (32900 rpm) for 45 minutes using a SW55 Ti rotor (Beckman Coulter). The supernatants were discarded and the pellets were re-suspended in ice-cold buffer (10 mM Tris, 300 mM NaCl, pH 8) and the tubes were again topped up with the same ice-cold buffer. After careful balancing and centrifugation at 100,000×g (32900 rpm) for 45 minutes, the supernatant was discarded and the pellets were re-suspended in ice-cold buffer (10 mM Tris, 300 mM NaCl, pH 8), approximately 800 μl per pellet. In total a membrane preparation of approximately 1.6 ml was collected and frozen in −80 degrees.

Tipsonication

The frozen membrane preparation was thawed on ice and pooled together prior sonication in an ice-cold conical vial using a sonicator (Vibracell). The membrane preparation was first diluted to 4 ml with ice-cold buffer (10 mM Tris, 300 mM NaCl, pH 8) and subjected to 30 seconds of sonication using 15% amplitude, 0.5 second pulse/rest cycle. The conical vial and membrane preparation were then cooled on ice for a few minutes and then another cycle using 15% amplitude, 0.5 second pulse/rest for 30 seconds were subjected to the membrane preparation and this was repeated again. The resulting membrane preparation (proteoliposomes) was frozen in 310 μl aliquots in −80 degrees.

Proteases

All proteases were purchased from Promega. All solutions were made using LC-MS grade water from Fisher Scientific.

Cat. No. V1621
Asp-N, Sequencing Grade, 2 μg
Cat. No. V1959
Pepsin, 250 mg
Cat. No. V3021
Proteinase K, 100 mg
Cat. No. V1062
Chymotrypsin, Sequencing Grade, 25 μg
Cat. No. V5111
Sequencing Grade Modified Trypsin, 20 μg
Trypsin
Trypsin was dissolved in 100 mM Ammonium bicarbonate, Ambic, pH 8
Asp-N
Asp-N was dissolved in 100 mM Ammonium bicarbonate, Ambic, pH 8
Pepsin
Pepsin was dissolved in 100 mM Ammonium bicarbonate, Ambic, pH 8
Proteinase K
Proteinase K was dissolved in 100 mM Ammonium bicarbonate, Ambic, pH 8
Chymotrypsin
Chymotrypsin was dissolved in 100 mM Tris-HCl, 10 mM $CaCl_2$, pH 8.

LPI processing

The experiments were performed using LPI HexaLanechips for the digestion. One lane within each chip were used for one digestion. In brief, aliquots of proteoliposomes were thawed to room temperature, manually injected into the lanes using a 100 μl pipette and immobilized for 1 hour.

Washing of the lanes was also performed manually using a 100 μl pipette. Each of the wells was washed with 200 μl wash buffer (same as digestion buffer, except for pepsin digestion protocol where 100 mM Ambic pH 8 was used as wash buffer. This was done to avoid low pH in the flow cell for a long time). The lanes were then washed with 4×100 μl of wash buffer using a 100 μl pipette.

Then protease was injected into the lane and incubated according to the specifications below. After digestion the peptides were eluted from the lane using 200 μl of digestion buffer (2×100 μl). By adding 4 μl of Formic acid, the protease activity was stopped by acidifying the resulting peptide solution to about pH 2. This was done for all samples except for pepsin, where 16 μl of ammonia solution (25%) was added instead to make the solution basic (pH 9).

The following digestion conditions were performed, one in each lane:

Trypsin:
0.5 μg/ml for 2.5 min
0.5 μg/ml for 5 min
2 μg/ml for 5 min
5 μg/ml for 5 min
10 μg/ml for 5 min
20 μg/ml for 5 min
Asp-N
20 μg/ml for 5 min
2 μg/ml for 24 hours
Chymotrypsin
5 μg/ml for 5 min
10 μg/ml for 5 min
20 μg/ml for 5 min
Proteinase-K
5 μg/ml for 5 min
10 μg/ml for 5 min
20 μg/ml for 5 min
Pepsin
2 μg/ml for 5 min
5 μg/ml for 5 min
10 μg/ml for 5 min
20 μg/ml for 5 min The samples were labelled and frozen in −80° C.

MS Analysis

The tryptic peptides were desalted on PepClean C18 spin columns (Thermo Fisher Scientific, Inc., Waltham, Mass., USA) according to the manufacturers guidelines, dried and reconstituted with 15 micro-liter of 0.1% formic acid (Sigma Aldrich, St Louis, Mo.) in 3% gradient grade acetonitrile (Merck KGaA, Darmstadt, Germany). A two micro-liter sample injection was made with an Easy-nLC autosampler (Thermo Fisher Scientific, Inc., Waltham, Mass., USA) and analyzed with an interfaced Q Exactive hybrid mass spectrometer (Thermo Fisher Scientific). The peptides were trapped on a precolumn (45×0.075 mm i.d.) and separated on a reversed phase column, 200×0.075 mm, packed in-house with 3 μm Reprosil-Pur C18-AQ particles (Dr. Maisch, Ammerbuch, Germany). The nanoLC (liquid chromatography) gradient was running at 200 nl/min, starting at 7% acetonitrile (ACN) in 0.2% formic acid, increased to 27% ACN during 25 min, then increased to 40% during 5 min and finally to 80% ACN during 5 min and hold at 80% ACN for 10 min.

Ions were created and sprayed into the mass spectrometer under a voltage of 1.8 kV and capillary temperature of 320 degrees Celsius in data-dependent positive ion mode. Full scan (MS1) spectra were acquired in the Orbitrap over the m/z range 400-1,600, charge range 2-6 at a resolution of 70,000 until an AGC target value of 1e6 at a maximum of 250 ms. MS/MS spectra were acquired using higher energy collision dissociation (HCD) at 30% from m/z 110 for the ten most abundant parent ions at a resolution of 35,000 using a precursor isolation window of 2 Da until an AGC target value of 1e5 during an injection time of 110 ms. Dynamic exclusion during 30 s after selection for MS/MS was enabled to allow for detection of as many precursors as possible.

Summary of Results

Figure 10:
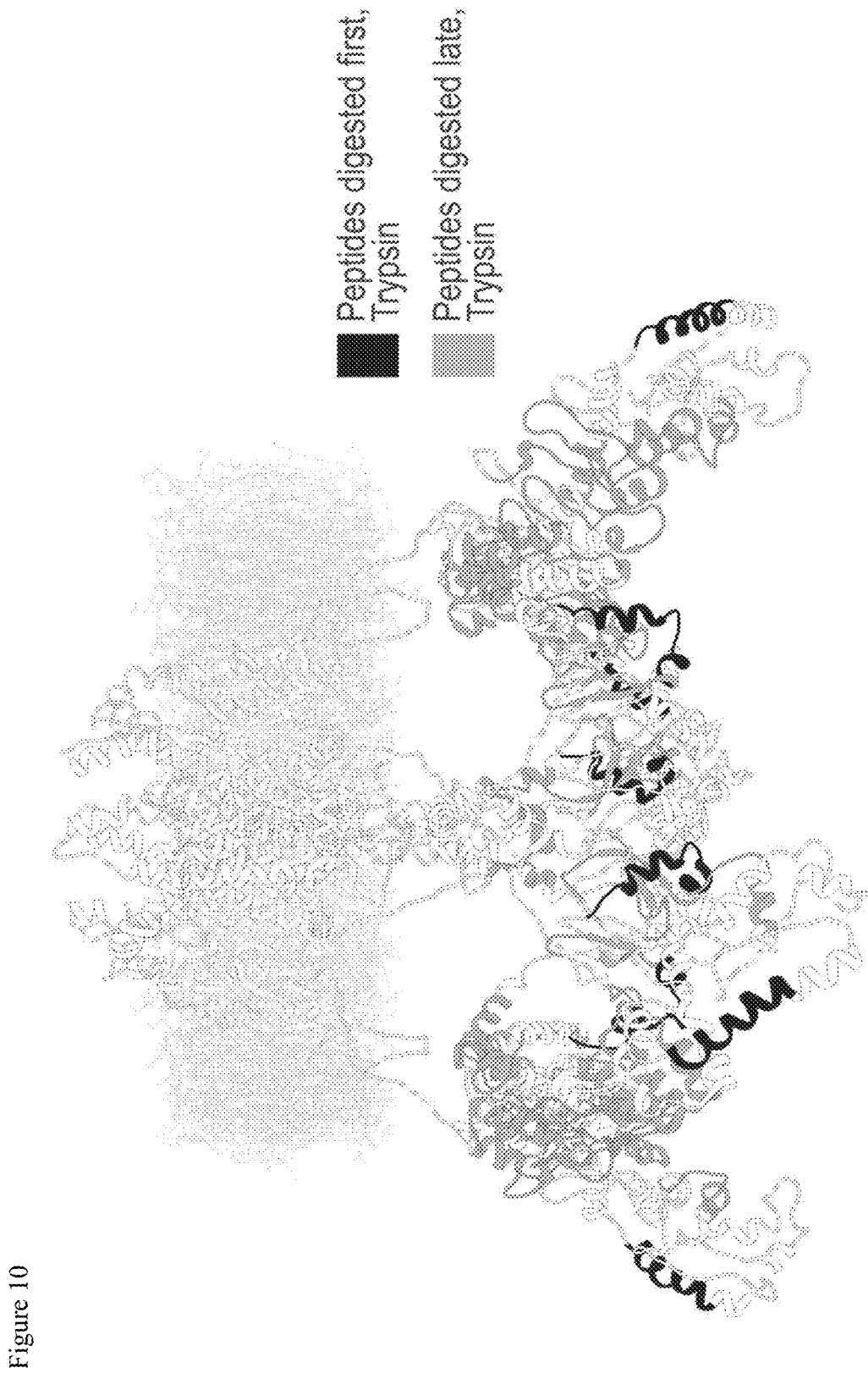

FIG. 10 shows the location on a 3D model of TRPV1 of peptides detected after limited proteolysis by trypsin. The sequences of detected peptides after limited proteolysis by trypsin are shown below in Table 2. Peptides digested with 0.5 µg/ml trypsin for 2.5 min are shown first. Peptides digested with 0.5 µg/ml trypsin for 5 min, 2 µg/ml trypsin for 5 min, 5 µg/ml trypsin for 5 min, 10 µg/ml trypsin for 5 min and 20 µg/ml trypsin for 5 min respectively have been pooled for presentation purposes and are shown secondly.

TABLE 2

| Start | Stop | Sequence |
|---|---|---|
| Peptides digested with 0.5 µg/ml trypsin for 2.5 min (*) | | |
| 96 | 108 | LLSQDSVAASTEK (SEQ ID NO: 2) |
| 96 | 111 | LLSQDSVAASTEKTLR (SEQ ID NO: 3) |
| 817 | 839 | QFSGSLKPEDAEVFKSPAASGEK (SEQ ID NO: 4) |
| Peptides digested with 0.5 µg/ml trypsin for 5 min, 2 µg/ml trypsin for 5 min, 5 µg/ml trypsin for 5 min, 10 µg/ml trypsin for 5 min and 20 µg/ml trypsin for 5 min. (**) | | |
| 4 | 18 | WSSTDLGAAADPLQK (SEQ ID NO: 27) |
| 96 | 108 | LLSQDSVAASTEK (SEQ ID NO: 28) |
| 96 | 111 | LLSQDSVAASTEKTLR (SEQ ID NO: 29) |
| 162 | 182 | AMLNLHDGQNTTIPLLLEIAR (SEQ ID NO: 30) |
| 183 | 201 | QTDSLKELVNASYTDSYYK (SEQ ID NO: 31) |
| 202 | 212 | GQTALHIAIER (SEQ ID NO: 32) |
| 214 | 239 | NMALVTLLVENGADVQAAAHGDFFKK (SEQ ID NO: 33) |
| 267 | 281 | FLLQNSWQTADISAR (SEQ ID NO: 34) |
| 282 | 304 | DSVGNTVLHALVEVADNTADNTK (SEQ ID NO: 35) |
| 320 | 332 | LHPTLKLEELTNK (SEQ ID NO: 36) |
| 333 | 346 | KGMTPLALAAGTGK (SEQ ID NO: 37) |
| 334 | 346 | GMTPLALAAGTGK (SEQ ID NO: 38) |
| 347 | 356 | IGVLAYILQR (SEQ ID NO: 39) |
| 703 | 711 | AITILDTEK (SEQ ID NO: 40) |
| 773 | 779 | TLSFSLR (SEQ ID NO: 41) |
| 790 | 798 | NFALVPLLR (SEQ ID NO: 42) |
| 799 | 816 | EASARDRQSAQPEEVYLR (SEQ ID NO: 43) |
| 804 | 816 | DRQSAQPEEVYLR (SEQ ID NO: 44) |
| 806 | 816 | QSAQPEEVYLR (SEQ ID NO: 45) |

TABLE 2-continued

| Start | Stop | Sequence |
|---|---|---|
| 817 | 831 | QFSGSLKPEDAEVFK (SEQ ID NO: 46) |
| 817 | 839 | QFSGSLKPEDAEVFKSPAASGEK (SEQ ID NO: 47) |

Figure 11:
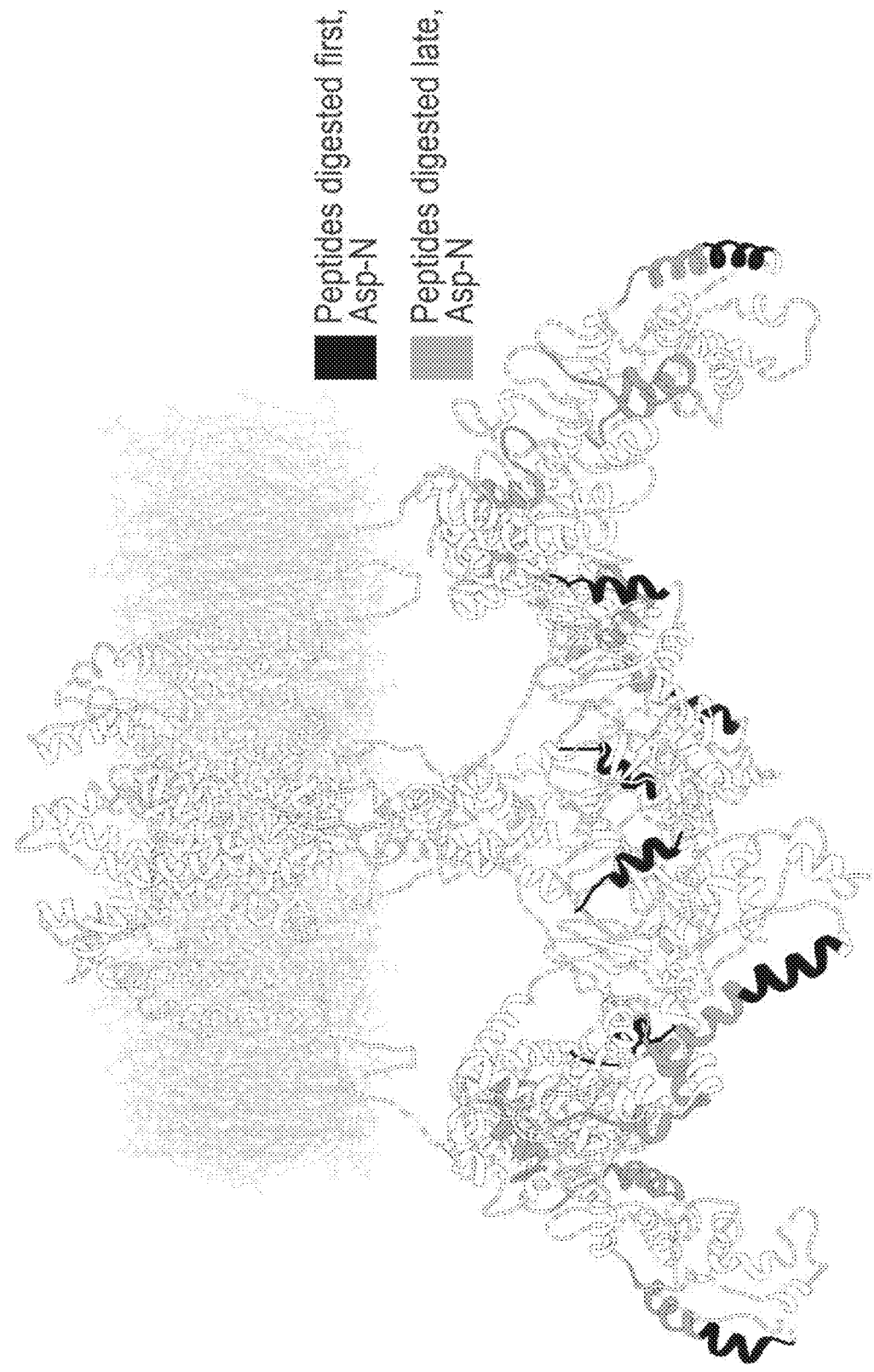

FIG. 11 shows the location on a 3D model of TRPV1 of peptides detected after limited proteolysis by Asp-N. The sequences of detected peptides after limited proteolysis by Asp-N are shown below in Table 3. Peptides digested with 20 µg/ml Asp-N for 5 min are shown first. Peptides digested with 2 µg/ml Asp-N for 24 hours are shown secondly.

TABLE 3

| Start | Stop | Sequence |
|---|---|---|
| Peptides digested with 20 µg/ml Asp-N for 5 min (*) | | |
| 89 | 99 | DGPTGARLLSQ (SEQ ID NO: 8) |
| 826 | 839 | DAEVFKSPAASGEK (SEQ ID NO: 9) |
| Peptides digested with 2 µg/ml Asp-N for 24 hours (**) | | |
| 89 | 99 | DGPTGARLLSQ (SEQ ID NO: 48) |
| 100 | 113 | DSVAASTEKTLRLY (SEQ ID NO: 49) |
| 168 | 184 | DGQNTTIPLLLEIARQT (SEQ ID NO: 50) |
| 185 | 196 | DSLKELVNASYT (SEQ ID NO: 51) |
| 282 | 296 | DSVGNTVLHALVEVA (SEQ ID NO: 52) |
| 826 | 839 | DAEVFKSPAASGEK (SEQ ID NO: 53) |

Figure 12:
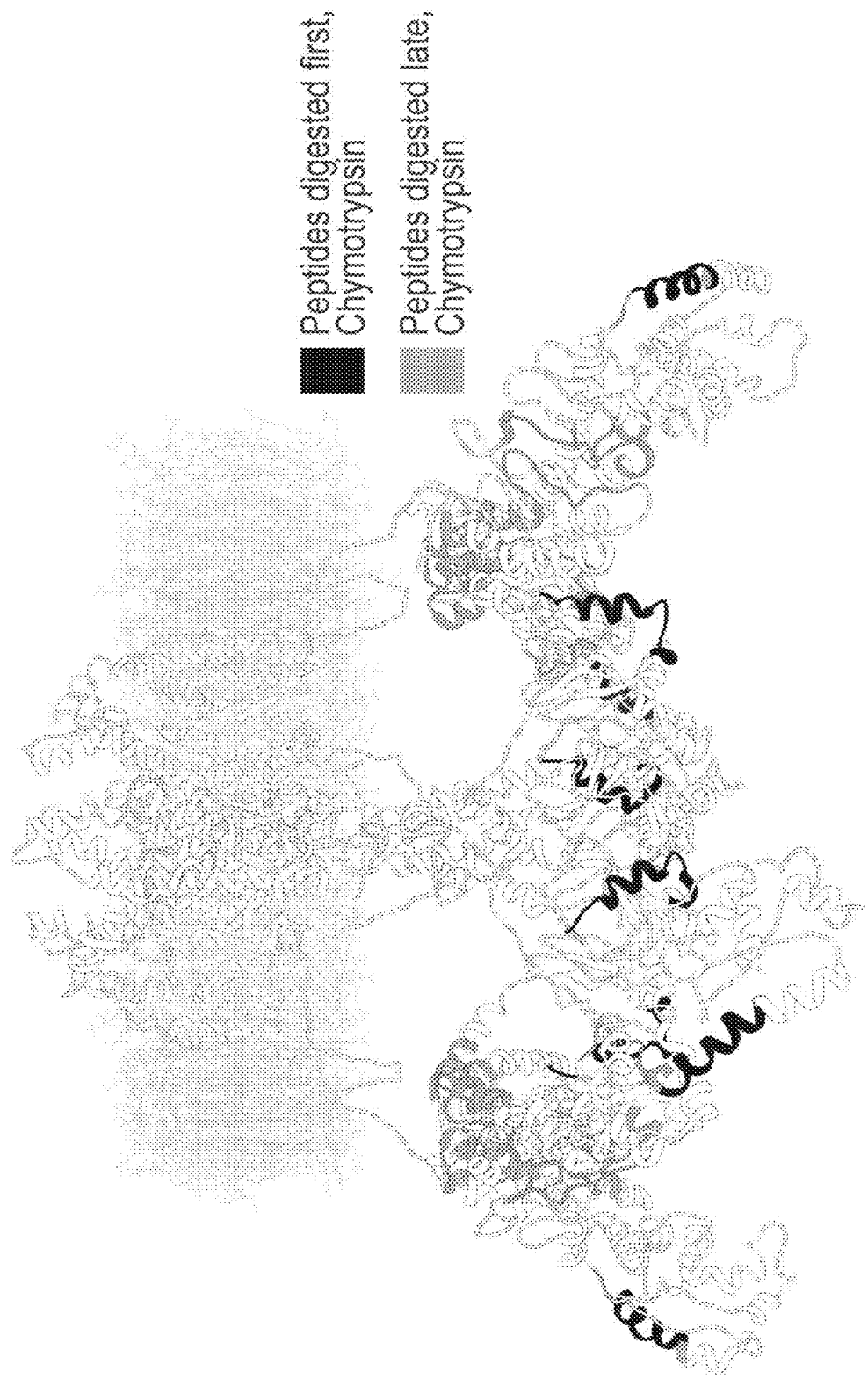

FIG. 12 shows the location on a 3D model of TRPV1 of peptides detected after limited proteolysis by chymotrypsin. The sequences of detected peptides after limited proteolysis by chymotrypsin are shown below in Table 4. Peptides digested with 5 µg/ml chymotrypsin for 5 min are shown first. Peptides digested with 10 µg/ml chymotrypsin for 5 min and 20 µg/ml chymotrypsin for 5 min respectively have been pooled for presentation purposes and are shown secondly.

TABLE 4

| Start | Stop | Sequence |
|---|---|---|
| Peptides digested with 5 µg/ml chymotrypsin for 5 min (*) | | |
| 98 | 110 | SQDSVAASTEKTL (SEQ ID NO: 10) |
| 819 | 830 | SGSLKPEDAEVF (SEQ ID NO: 11) |
| Peptides digested with 10 µg/ml chymotrypsin for 5 min and 20 µg/ml for 5 min (**) | | |
| 97 | 110 | LSQDSVAASTEKTL (SEQ ID NO: 54) |
| 98 | 110 | SQDSVAASTEKTL (SEQ ID NO: 55) |
| 98 | 113 | SQDSVAASTEKTLRLY (SEQ ID NO: 56) |
| 165 | 176 | NLHDGQNTTIPL (SEQ ID NO: 57) |
| 221 | 237 | LVENGADVQAAAHGDFF (SEQ ID NO: 58) |

TABLE 4-continued

| Start | Stop | Sequence |
|---|---|---|
| 274 | 289 | QTADISARDSVGNTVL (SEQ ID NO: 59) |
| 290 | 305 | HALVEVADNTADNTKF (SEQ ID NO: 60) |
| 341 | 352 | AAGTGKIGVLAY (SEQ ID NO: 61) |
| 819 | 830 | SGSLKPEDAEVF (SEQ ID NO: 62) |

Figure 13:
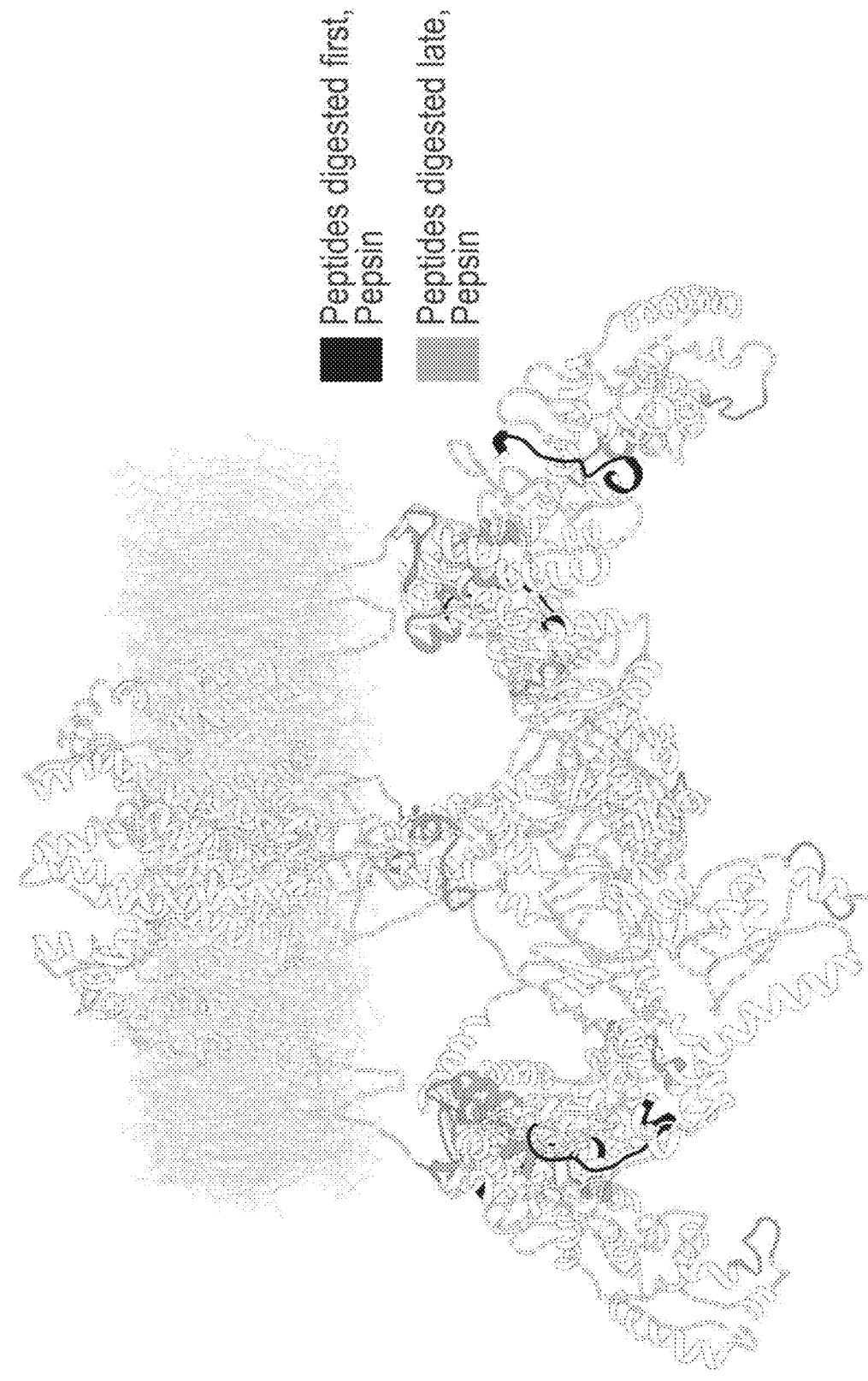

FIG. 13 shows the location on a 3D model of TRPV1 of peptides detected after limited proteolysis by pepsin. The sequences of detected peptides after limited proteolysis by pepsin are shown below in Table 5. Peptides digested with 2 μg/ml pepsin for 5 min are shown first. Peptides digested with 5 μg/ml pepsin for 5 min, 10 μg/ml pepsin for 5 min and 20 μg/ml pepsin for 5 min respectively have been pooled for presentation purposes and are shown secondly.

TABLE 5

| Start | Stop | Sequence |
|---|---|---|
| | | Peptides digested with 2 μg/ml pepsin for 5 min (*) |
| 221 | 236 | LVENGADVQAAAHGDF (SEQ ID NO: 7) |
| | | Peptides digested with 5 μg/ml pepsin for 5 min, 10 μg/ml pepsin for 5 min and 20 μg/ml pepsin for 5 min |
| 50 | 59 | FGKGDSEEAF (SEQ ID NO: 63) |
| 167 | 177 | HDGQNTTIPLL (SEQ ID NO: 64) |
| 221 | 236 | LVENGADVQAAAHGDF (SEQ ID NO: 65) |
| 222 | 235 | VENGADVQAAAHGDF (SEQ ID NO: 66) |
| 222 | 236 | VENGADVQAAAHGDF (SEQ ID NO: 67) |
| 290 | 305 | HALVEVADNTADNTKF (SEQ ID NO: 68) |
| 293 | 305 | VEVADNTADNTKF (SEQ ID NO: 69) |
| 398 | 414 | EVIAYSSSETPNRHDML (SEQ ID NO: 70) |

Figure 14:
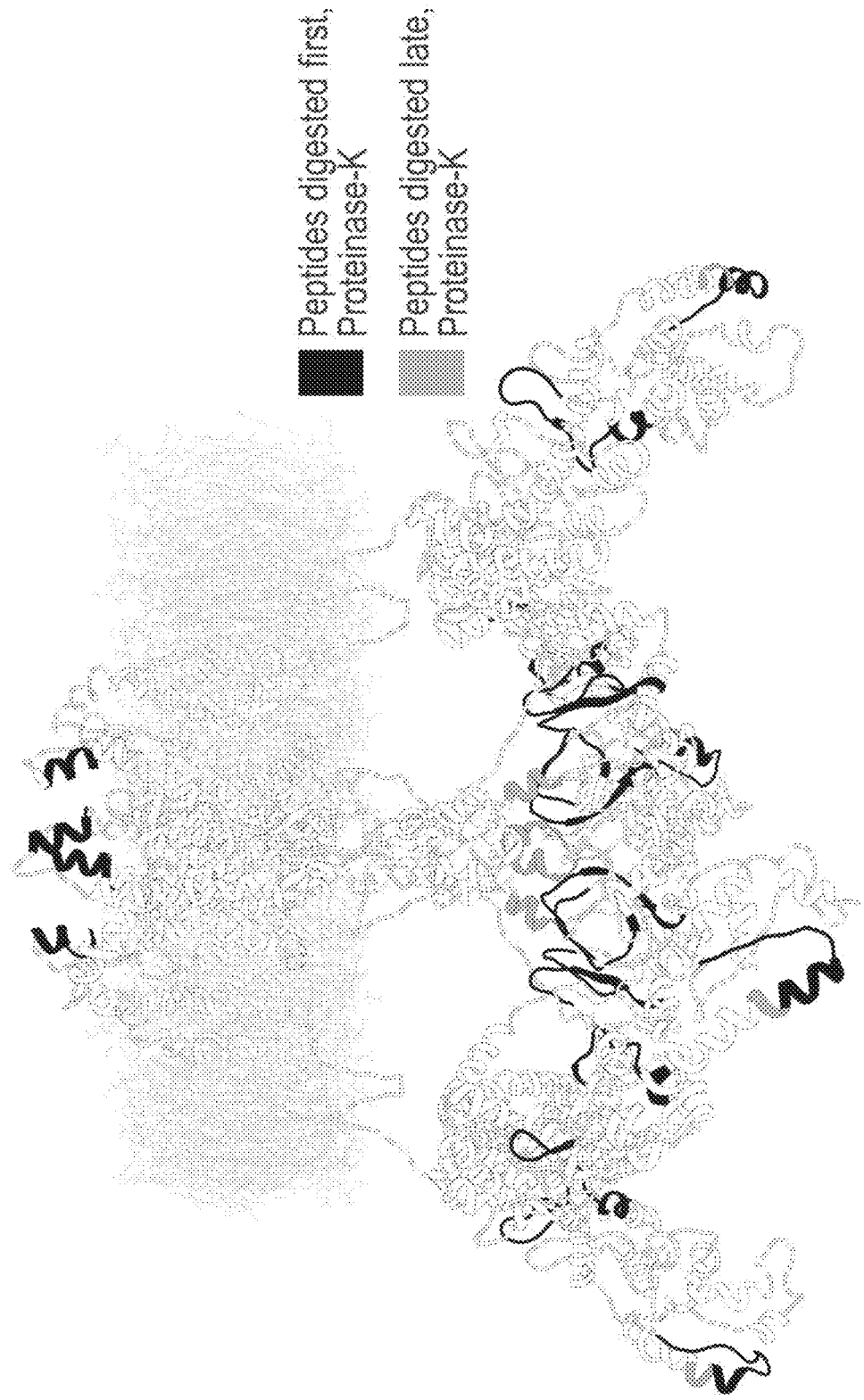

FIG. 14 shows the location on a 3D model of TRPV1 of peptides detected after limited proteolysis by Proteinase K. The sequences of detected peptides after limited proteolysis by Proteinase K are shown below in Table 6. Peptides digested with 5 μg/ml proteinase K for 5 min are shown first. Peptides digested with 10 μg/ml proteinase K for 5 min, and 20 μg/ml proteinase K for 5 min respectively have been pooled for presentation purposes and are shown secondly.

TABLE 6

| Start | Stop | Sequence |
|---|---|---|
| | | Peptides digested with 5 μg/ml proteinase K for 5 min (*) |
| 78 | 89 | VSPVITIQRPGD (SEQ ID NO: 12) |
| 78 | 94 | VSPVITIQRPGDGPTGA (SEQ ID NO: 13) |
| 164 | 178 | LNLHDGQNTTIPLLL (SEQ ID NO: 14) |
| 195 | 203 | YTDSYYKGQ (SEQ ID NO: 15) |
| 606 | 614 | SLPSESTSH (SEQ ID NO: 16) |
| 762 | 772 | EDPGNCEGVKR (SEQ ID NO: 17) |
| 804 | 816 | DRQSAQPEEVYLR (SEQ ID NO: 18) |
| 806 | 816 | QSAQPEEVYLR (SEQ ID NO: 19) |
| | | Peptides digested with 10 μg/ml proteinase K for 5 min, and 20 μg/ml proteinase K for 5 min (**) |
| 78 | 94 | VSPVITIQRPGDGPTGA (SEQ ID NO: 71) |
| 84 | 95 | IQRPGDGPTGAR (SEQ ID NO: 72) |
| 86 | 97 | RPGDGPTGARLL (SEQ ID NO: 73) |
| 164 | 178 | LNLHDGQNTTIPLLL (SEQ ID NO: 74) |
| 708 | 715 | DTEKSFLK (SEQ ID NO: 75) |
| 762 | 772 | EDPGNCEGVKR (SEQ ID NO: 76) |
| 762 | 773 | EDPGNCEGVKRT (SEQ ID NO: 77) |
| 762 | 774 | EDPGNCEGVKRTL (SEQ ID NO: 78) |
| 801 | 816 | SARDRQSAQPEEVYLR (SEQ ID NO: 79) |
| 804 | 816 | DRQSAQPEEVYLR (SEQ ID NO: 80) |
| 806 | 816 | QSAQPEEVYLR (SEQ ID NO: 81) |

In Tables 2, 3, 4, 5 and 6 the terms "start" and "stop" refer to the positions of the amino acid residues in the TRPV1 sequence.

During evaluation of the data a Mascot Significance Threshold of 0.01 has been set under Results Filters (Peptide).

Trypsin produced an increased number of peptides and increased confidence with an increased protease concentration.

Pepsin and Chymotrypsin both gave rise to a number of peptides both at low and higher concentrations.

The invention claimed is:

1. A method of generating an antibody to a protein, said method comprising:
   (i) exposing the protein to limited or restricted proteolysis by contacting the protein with at least one protease to form at least one digested, deconstructed or truncated version of the protein and at least one surface-exposed peptide that is cleaved off from the protein by the action of said protease; and
   (ii) identifying an antigenic epitope by identifying a surface-exposed epitope among the at least one surface-exposed peptide that is present in a region of the protein that results in a lack of, or significantly altered, biological function of the protein when the peptide is cleaved off or removed from the protein during the limited or restricted proteolysis; or
   selecting at least one target region within the protein based on bioinformatics and/or known data of biological function of the protein and identifying an antigenic epitope by identifying a surface-exposed epitope among the at least one surface-exposed peptide present in said at least one target region; and (iii) raising an antibody against the antigenic epitope.

2. The method of claim 1, wherein said at least one protease is used under conditions which result in at most 8 or at most 7 or at most 5 surface exposed peptides, or at most 8 or at most 7 or at most 5 unique surface exposed peptides, being cleaved off from the protein by the action of said protease in a sample of the proteolytically digested material, and optionally multiple samples are taken or run in sequence or in parallel, optionally at different periods of time and/or at different concentrations of said protease.

3. The method of claim 1, wherein said at least one protease is used under conditions which result in at most 8 or at most 7 or at most 5 surface exposed peptides being cleaved off from the protein by the action of said protease.

4. The method of claim 1, wherein the kinetic activity of said at least one protease is slowed down so much that said surface exposed peptides are cleaved off one at a time or at most a few at a time, for example at most 8 or at most 7 or at most 5 at a time in a sample, and optionally multiple samples are taken or run in sequence or in parallel.

5. The method of claim 1, wherein said cleaved off surface-exposed peptides are ranked based on order of appearance after being contacted with said at least one protease, wherein the surface exposed peptides that are cleaved off first or at the lowest concentration of said protease are given a high rank and the surface exposed peptides that are cleaved off late or at the highest concentration of said protease are given a low rank, and optionally surface exposed peptides that are cleaved off in between may be ranked in order of their appearance.

6. The method of claim 5, wherein said method comprises picking a surface-exposed peptide having a high rank for antigenic epitope development and raising an antibody against said antigenic epitope.

7. The method of claim 5, wherein said method comprises picking a surface-exposed peptide having a high rank, constructing an antigenic epitope based on said surface-exposed peptide and raising an antibody against said antigenic epitope.

8. The method of claim 5, wherein said method comprises picking a surface-exposed peptide having a high rank, correlating said surface exposed-peptide with a defined biological property of the protein, constructing an antigenic epitope based on said surface-exposed peptide and raising an antibody against said antigenic epitope.

9. The method of claim 1, wherein a single protease is used to digest, deconstruct and/or truncate said protein.

10. The method of claim 1, wherein multiple proteases are used to digest, deconstruct and/or truncate said protein.

11. The method of claim 10, wherein the multiple proteases are used sequentially one at a time, are used in parallel, or are used in a single cocktail of multiple proteases.

12. The method of claim 10, wherein said multiple proteases are used to identify overlapping, complementary, or unique surface-exposed peptides.

13. The method of claim 1, wherein said protease is selected from the group consisting of: trypsin, Arg-C proteinase, Asp-N endopeptidase, Clostripain, Glutamyl endopeptidase, Lys-C, Lys-N, Chymotrypsin, Proteinase K, Thermolysin, Pepsin, Caspase 1, Caspase 2, Caspase 3, Caspase 4, Caspase 5, Caspase 6, Caspase 7, Caspase 8, Caspase 9, Caspase 10, Enterokinase, Factor Xa, GranzymeB, Neutrophil elastase, Proline-endopeptidase, Staphylococcal peptidase I, and Thrombin.

14. The method of claim 1, wherein said protease is trypsin.

15. The method of claim 1, wherein said protein is a membrane protein that is present in a proteoliposome derived from cells.

16. The method claim 15, wherein said proteoliposome is immobilized in a flow cell to create a stationary phase of membrane proteins.

17. The method of claim 1, wherein said protein is in a protein-containing lipid vesicle that is surface-bound or suspended in a solution.

18. The method of claim 1, wherein said protein is in an intact cell that is surface-bound or suspended in a solution.

19. The method of claim 1, wherein said protein is in a solution.

20. The method of claim 1, wherein said protein is any protein of the human proteome.

21. The method of claim 1, wherein said protein is a membrane bound protein, a soluble protein, an extracellular protein or an intracellular protein.

22. The method of claim 1, wherein said protein is a membrane or a membrane associated protein.

23. The method of claim 1, wherein said protein is an ion channel in the TRP superfamily.

24. The method of claim 23, wherein said protein is TRPV1 or TRPV2.

25. The method of claim 1, wherein said protein is an excitatory amino acid receptor.

26. The method of claim 25, wherein said protein is the NMDA receptor or a G-protein.

27. The method of claim 1, wherein said protein is an oncogenic protein.

28. The method of claim 27, wherein said protein is an oncogenic small GTPase selected from the group consisting of KRAS, NRAS and HRAS.

29. The method of claim 1, wherein said protein is an immunomodulatory protein.

30. The method of claim 29, wherein said protein is selected from the group consisting of PD1, PDL1, CD40, OX40, VISTA, LAG-3, TIM-3, GITR and CD20.

31. The method of claim 1, wherein said cleaved-off peptides are identified with mass spectrometry.

32. The method of claim 31, wherein said cleaved-off peptides are identified with LC-MS/MS.

33. The method of claim 1, wherein said biological function is selected from the group consisting of capability of said protein to bind to a target such as a ligand or receptor, enzymatic activity of said protein, ion channel activity, transporter activity, and release such as insulin release and uptake machinery.

34. The method of claim 1, wherein raising an antibody against an antigenic epitope is performed by hybridoma technology, phage display technology, or by immunizing an animal with said antigenic epitope.

35. The method according to claim 1, wherein said antibody is monoclonal or polyclonal.

* * * * *

SEQUENCE LISTING

<160> NUMBER OF SEQ ID NOS: 81

<210> SEQ ID NO 1
<211> LENGTH: 839
<212> TYPE: PRT
<213> ORGANISM: Homo sapiens

<400> SEQUENCE: 1

Met Lys Lys Trp Ser Ser Thr Asp Leu Gly Ala Ala Ala Asp Pro Leu
1               5                   10                  15

-continued

```
Gln Lys Asp Thr Cys Pro Asp Pro Leu Asp Gly Asp Pro Asn Ser Arg
             20                  25                  30

Pro Pro Pro Ala Lys Pro Gln Leu Ser Thr Ala Lys Ser Arg Thr Arg
         35                  40                  45

Leu Phe Gly Lys Gly Asp Ser Glu Glu Ala Phe Pro Val Asp Cys Pro
     50                  55                  60

His Glu Glu Gly Glu Leu Asp Ser Cys Pro Thr Ile Thr Val Ser Pro
 65                  70                  75                  80

Val Ile Thr Ile Gln Arg Pro Gly Asp Gly Pro Thr Gly Ala Arg Leu
                 85                  90                  95

Leu Ser Gln Asp Ser Val Ala Ala Ser Thr Glu Lys Thr Leu Arg Leu
            100                 105                 110

Tyr Asp Arg Arg Ser Ile Phe Glu Ala Val Ala Gln Asn Asn Cys Gln
        115                 120                 125

Asp Leu Glu Ser Leu Leu Leu Phe Leu Gln Lys Ser Lys Lys His Leu
    130                 135                 140

Thr Asp Asn Glu Phe Lys Asp Pro Glu Thr Gly Lys Thr Cys Leu Leu
145                 150                 155                 160

Lys Ala Met Leu Asn Leu His Asp Gly Gln Asn Thr Thr Ile Pro Leu
                165                 170                 175

Leu Leu Glu Ile Ala Arg Gln Thr Asp Ser Leu Lys Glu Leu Val Asn
            180                 185                 190

Ala Ser Tyr Thr Asp Ser Tyr Tyr Lys Gly Gln Thr Ala Leu His Ile
        195                 200                 205

Ala Ile Glu Arg Arg Asn Met Ala Leu Val Thr Leu Leu Val Glu Asn
    210                 215                 220

Gly Ala Asp Val Gln Ala Ala Ala His Gly Asp Phe Phe Lys Lys Thr
225                 230                 235                 240

Lys Gly Arg Pro Gly Phe Tyr Phe Gly Glu Leu Pro Leu Ser Leu Ala
                245                 250                 255

Ala Cys Thr Asn Gln Leu Gly Ile Val Lys Phe Leu Leu Gln Asn Ser
            260                 265                 270

Trp Gln Thr Ala Asp Ile Ser Ala Arg Asp Ser Val Gly Asn Thr Val
        275                 280                 285

Leu His Ala Leu Val Glu Val Ala Asp Asn Thr Ala Asp Asn Thr Lys
    290                 295                 300

Phe Val Thr Ser Met Tyr Asn Glu Ile Leu Met Leu Gly Ala Lys Leu
305                 310                 315                 320

His Pro Thr Leu Lys Leu Glu Glu Leu Thr Asn Lys Lys Gly Met Thr
                325                 330                 335

Pro Leu Ala Leu Ala Ala Gly Thr Gly Lys Ile Gly Val Leu Ala Tyr
            340                 345                 350

Ile Leu Gln Arg Glu Ile Gln Glu Pro Glu Cys Arg His Leu Ser Arg
        355                 360                 365

Lys Phe Thr Glu Trp Ala Tyr Gly Pro Val His Ser Ser Leu Tyr Asp
    370                 375                 380

Leu Ser Cys Ile Asp Thr Cys Glu Lys Asn Ser Val Leu Glu Val Ile
385                 390                 395                 400

Ala Tyr Ser Ser Ser Glu Thr Pro Asn Arg His Asp Met Leu Leu Val
                405                 410                 415

Glu Pro Leu Asn Arg Leu Leu Gln Asp Lys Trp Asp Arg Phe Val Lys
            420                 425                 430

Arg Ile Phe Tyr Phe Asn Phe Leu Val Tyr Cys Leu Tyr Met Ile Ile
```

```
                    435                 440                 445
Phe Thr Met Ala Ala Tyr Tyr Arg Pro Val Asp Gly Leu Pro Phe
    450                 455                 460

Lys Met Glu Lys Thr Gly Asp Tyr Phe Arg Val Thr Gly Glu Ile Leu
465                 470                 475                 480

Ser Val Leu Gly Gly Val Tyr Phe Phe Arg Gly Ile Gln Tyr Phe
                485                 490                 495

Leu Gln Arg Arg Pro Ser Met Lys Thr Leu Phe Val Asp Ser Tyr Ser
    500                 505                 510

Glu Met Leu Phe Phe Leu Gln Ser Leu Phe Met Leu Ala Thr Val Val
        515                 520                 525

Leu Tyr Phe Ser His Leu Lys Glu Tyr Val Ala Ser Met Val Phe Ser
    530                 535                 540

Leu Ala Leu Gly Trp Thr Asn Met Leu Tyr Tyr Thr Arg Gly Phe Gln
545                 550                 555                 560

Gln Met Gly Ile Tyr Ala Val Met Ile Glu Lys Met Ile Leu Arg Asp
                565                 570                 575

Leu Cys Arg Phe Met Phe Val Tyr Ile Val Phe Leu Phe Gly Phe Ser
                580                 585                 590

Thr Ala Val Val Thr Leu Ile Glu Asp Gly Lys Asn Asp Ser Leu Pro
            595                 600                 605

Ser Glu Ser Thr Ser His Arg Trp Arg Gly Pro Ala Cys Arg Pro Pro
610                 615                 620

Asp Ser Ser Tyr Asn Ser Leu Tyr Ser Thr Cys Leu Glu Leu Phe Lys
625                 630                 635                 640

Phe Thr Ile Gly Met Gly Asp Leu Glu Phe Thr Glu Asn Tyr Asp Phe
                645                 650                 655

Lys Ala Val Phe Ile Ile Leu Leu Leu Ala Tyr Val Ile Leu Thr Tyr
                660                 665                 670

Ile Leu Leu Leu Asn Met Leu Ile Ala Leu Met Gly Glu Thr Val Asn
                675                 680                 685

Lys Ile Ala Gln Glu Ser Lys Asn Ile Trp Lys Leu Gln Arg Ala Ile
690                 695                 700

Thr Ile Leu Asp Thr Glu Lys Ser Phe Leu Lys Cys Met Arg Lys Ala
705                 710                 715                 720

Phe Arg Ser Gly Lys Leu Leu Gln Val Gly Tyr Thr Pro Asp Gly Lys
                725                 730                 735

Asp Asp Tyr Arg Trp Cys Phe Arg Val Asp Glu Val Asn Trp Thr Thr
                740                 745                 750

Trp Asn Thr Asn Val Gly Ile Ile Asn Glu Asp Pro Gly Asn Cys Glu
    755                 760                 765

Gly Val Lys Arg Thr Leu Ser Phe Ser Leu Arg Ser Ser Arg Val Ser
    770                 775                 780

Gly Arg His Trp Lys Asn Phe Ala Leu Val Pro Leu Leu Arg Glu Ala
785                 790                 795                 800

Ser Ala Arg Asp Arg Gln Ser Ala Gln Pro Glu Val Tyr Leu Arg
                805                 810                 815

Gln Phe Ser Gly Ser Leu Lys Pro Glu Asp Ala Glu Val Phe Lys Ser
                820                 825                 830

Pro Ala Ala Ser Gly Glu Lys
                835

<210> SEQ ID NO 2
```

```
<211> LENGTH: 13
<212> TYPE: PRT
<213> ORGANISM: Artificial Sequence
<220> FEATURE:
<223> OTHER INFORMATION: peptide sequence

<400> SEQUENCE: 2

Leu Leu Ser Gln Asp Ser Val Ala Ala Ser Thr Glu Lys
1               5                   10

<210> SEQ ID NO 3
<211> LENGTH: 16
<212> TYPE: PRT
<213> ORGANISM: Artificial Sequence
<220> FEATURE:
<223> OTHER INFORMATION: peptide sequence

<400> SEQUENCE: 3

Leu Leu Ser Gln Asp Ser Val Ala Ala Ser Thr Glu Lys Thr Leu Arg
1               5                   10                  15

<210> SEQ ID NO 4
<211> LENGTH: 23
<212> TYPE: PRT
<213> ORGANISM: Artificial Sequence
<220> FEATURE:
<223> OTHER INFORMATION: peptide sequence

<400> SEQUENCE: 4

Gln Phe Ser Gly Ser Leu Lys Pro Glu Asp Ala Glu Val Phe Lys Ser
1               5                   10                  15

Pro Ala Ala Ser Gly Glu Lys
            20

<210> SEQ ID NO 5
<211> LENGTH: 22
<212> TYPE: PRT
<213> ORGANISM: Artificial Sequence
<220> FEATURE:
<223> OTHER INFORMATION: peptide sequence

<400> SEQUENCE: 5

Leu Leu Ser Gln Asp Ser Val Ala Ala Ser Thr Glu Lys Thr Leu Arg
1               5                   10                  15

Leu Tyr Asp Arg Arg Ser
            20

<210> SEQ ID NO 6
<211> LENGTH: 15
<212> TYPE: PRT
<213> ORGANISM: Artificial Sequence
<220> FEATURE:
<223> OTHER INFORMATION: peptide sequence

<400> SEQUENCE: 6

Gly Arg His Trp Lys Asn Phe Ala Leu Val Pro Leu Leu Arg Glu
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: peptide sequence

<400> SEQUENCE: 7
```

```
Leu Val Glu Asn Gly Ala Asp Val Gln Ala Ala His Gly Asp Phe
 1               5                  10                  15

<210> SEQ ID NO 8
<211> LENGTH: 11
<212> TYPE: PRT
<213> ORGANISM: Artificial Sequence
<220> FEATURE:
<223> OTHER INFORMATION: peptide sequence

<400> SEQUENCE: 8

Asp Gly Pro Thr Gly Ala Arg Leu Leu Ser Gln
 1               5                  10

<210> SEQ ID NO 9
<211> LENGTH: 14
<212> TYPE: PRT
<213> ORGANISM: Artificial Sequence
<220> FEATURE:
<223> OTHER INFORMATION: peptide sequence

<400> SEQUENCE: 9

Asp Ala Glu Val Phe Lys Ser Pro Ala Ala Ser Gly Glu Lys
 1               5                  10

<210> SEQ ID NO 10
<211> LENGTH: 13
<212> TYPE: PRT
<213> ORGANISM: Artificial Sequence
<220> FEATURE:
<223> OTHER INFORMATION: peptide sequence

<400> SEQUENCE: 10

Ser Gln Asp Ser Val Ala Ala Ser Thr Glu Lys Thr Leu
 1               5                  10

<210> SEQ ID NO 11
<211> LENGTH: 12
<212> TYPE: PRT
<213> ORGANISM: Artificial Sequence
<220> FEATURE:
<223> OTHER INFORMATION: peptide sequence

<400> SEQUENCE: 11

Ser Gly Ser Leu Lys Pro Glu Asp Ala Glu Val Phe
 1               5                  10

<210> SEQ ID NO 12
<211> LENGTH: 12
<212> TYPE: PRT
<213> ORGANISM: Artificial Sequence
<220> FEATURE:
<223> OTHER INFORMATION: peptide sequence

<400> SEQUENCE: 12

Val Ser Pro Val Ile Thr Ile Gln Arg Pro Gly Asp
 1               5                  10

<210> SEQ ID NO 13
<211> LENGTH: 17
<212> TYPE: PRT
<213> ORGANISM: Artificial Sequence
<220> FEATURE:
<223> OTHER INFORMATION: peptide sequence

<400> SEQUENCE: 13

Val Ser Pro Val Ile Thr Ile Gln Arg Pro Gly Asp Gly Pro Thr Gly
```

Ala

<210> SEQ ID NO 14
<211> LENGTH: 15
<212> TYPE: PRT
<213> ORGANISM: Artificial Sequence
<220> FEATURE:
<223> OTHER INFORMATION: peptide sequence

<400> SEQUENCE: 14

Leu Asn Leu His Asp Gly Gln Asn Thr Thr Ile Pro Leu Leu Leu
1               5                   10                  15

<210> SEQ ID NO 15
<211> LENGTH: 9
<212> TYPE: PRT
<213> ORGANISM: Artificial Sequence
<220> FEATURE:
<223> OTHER INFORMATION: peptide sequence

<400> SEQUENCE: 15

Tyr Thr Asp Ser Tyr Tyr Lys Gly Gln
1               5

<210> SEQ ID NO 16
<211> LENGTH: 9
<212> TYPE: PRT
<213> ORGANISM: Artificial Sequence
<220> FEATURE:
<223> OTHER INFORMATION: peptide sequence

<400> SEQUENCE: 16

Ser Leu Pro Ser Glu Ser Thr Ser His
1               5

<210> SEQ ID NO 17
<211> LENGTH: 11
<212> TYPE: PRT
<213> ORGANISM: Artificial Sequence
<220> FEATURE:
<223> OTHER INFORMATION: peptide sequence

<400> SEQUENCE: 17

Glu Asp Pro Gly Asn Cys Glu Gly Val Lys Arg
1               5                   10

<210> SEQ ID NO 18
<211> LENGTH: 13
<212> TYPE: PRT
<213> ORGANISM: Artificial Sequence
<220> FEATURE:
<223> OTHER INFORMATION: peptide sequence

<400> SEQUENCE: 18

Asp Arg Gln Ser Ala Gln Pro Glu Glu Val Tyr Leu Arg
1               5                   10

<210> SEQ ID NO 19
<211> LENGTH: 11
<212> TYPE: PRT
<213> ORGANISM: Artificial Sequence
<220> FEATURE:
<223> OTHER INFORMATION: peptide sequence

<400> SEQUENCE: 19

```
Gln Ser Ala Gln Pro Glu Glu Val Tyr Leu Arg
1               5                   10
```

<210> SEQ ID NO 20
<211> LENGTH: 16
<212> TYPE: PRT
<213> ORGANISM: Artificial Sequence
<220> FEATURE:
<223> OTHER INFORMATION: peptide sequence

<400> SEQUENCE: 20

```
Phe Ala Pro Gln Ile Arg Val Asn Leu Asn Tyr Arg Lys Gly Thr Gly
1               5                   10                  15
```

<210> SEQ ID NO 21
<211> LENGTH: 13
<212> TYPE: PRT
<213> ORGANISM: Artificial Sequence
<220> FEATURE:
<223> OTHER INFORMATION: peptide sequence

<400> SEQUENCE: 21

```
Ala Ser Gln Pro Asp Pro Asn Arg Phe Asp Arg Asp Arg
1               5                   10
```

<210> SEQ ID NO 22
<211> LENGTH: 15
<212> TYPE: PRT
<213> ORGANISM: Artificial Sequence
<220> FEATURE:
<223> OTHER INFORMATION: peptide sequence

<400> SEQUENCE: 22

```
Leu Asn Leu Lys Asp Gly Val Asn Ala Cys Ile Leu Pro Leu Leu
1               5                   10                  15
```

<210> SEQ ID NO 23
<211> LENGTH: 9
<212> TYPE: PRT
<213> ORGANISM: Artificial Sequence
<220> FEATURE:
<223> OTHER INFORMATION: peptide sequence

<400> SEQUENCE: 23

```
Cys Thr Asp Asp Tyr Tyr Arg Gly His
1               5
```

<210> SEQ ID NO 24
<211> LENGTH: 16
<212> TYPE: PRT
<213> ORGANISM: Artificial Sequence
<220> FEATURE:
<223> OTHER INFORMATION: peptide sequence

<400> SEQUENCE: 24

```
Leu Val Glu Asn Gly Ala Asn Val His Ala Arg Ala Cys Gly Arg Phe
1               5                   10                  15
```

<210> SEQ ID NO 25
<211> LENGTH: 10
<212> TYPE: PRT
<213> ORGANISM: Artificial Sequence
<220> FEATURE:
<223> OTHER INFORMATION: peptide sequence

<400> SEQUENCE: 25

```
Glu Asp Pro Ser Gly Ala Gly Val Pro Arg
```

```
1               5                   10

<210> SEQ ID NO 26
<211> LENGTH: 15
<212> TYPE: PRT
<213> ORGANISM: Artificial Sequence
<220> FEATURE:
<223> OTHER INFORMATION: peptide sequence

<400> SEQUENCE: 26

Gly Ala Ser Glu Glu Asn Tyr Val Pro Val Gln Leu Leu Gln Ser
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: peptide sequence

<400> SEQUENCE: 27

Trp Ser Ser Thr Asp Leu Gly Ala Ala Ala Asp Pro Leu Gln Lys
1               5                   10                  15

<210> SEQ ID NO 28
<211> LENGTH: 13
<212> TYPE: PRT
<213> ORGANISM: Artificial Sequence
<220> FEATURE:
<223> OTHER INFORMATION: peptide sequence

<400> SEQUENCE: 28

Leu Leu Ser Gln Asp Ser Val Ala Ala Ser Thr Glu Lys
1               5                   10

<210> SEQ ID NO 29
<211> LENGTH: 16
<212> TYPE: PRT
<213> ORGANISM: Artificial Sequence
<220> FEATURE:
<223> OTHER INFORMATION: peptide sequence

<400> SEQUENCE: 29

Leu Leu Ser Gln Asp Ser Val Ala Ala Ser Thr Glu Lys Thr Leu Arg
1               5                   10                  15

<210> SEQ ID NO 30
<211> LENGTH: 21
<212> TYPE: PRT
<213> ORGANISM: Artificial Sequence
<220> FEATURE:
<223> OTHER INFORMATION: peptide sequence

<400> SEQUENCE: 30

Ala Met Leu Asn Leu His Asp Gly Gln Asn Thr Thr Ile Pro Leu Leu
1               5                   10                  15

Leu Glu Ile Ala Arg
            20

<210> SEQ ID NO 31
<211> LENGTH: 19
<212> TYPE: PRT
<213> ORGANISM: Artificial Sequence
<220> FEATURE:
<223> OTHER INFORMATION: peptide sequence

<400> SEQUENCE: 31
```

Gln Thr Asp Ser Leu Lys Glu Leu Val Asn Ala Ser Tyr Thr Asp Ser
1               5                   10                  15

Tyr Tyr Lys

<210> SEQ ID NO 32
<211> LENGTH: 11
<212> TYPE: PRT
<213> ORGANISM: Artificial Sequence
<220> FEATURE:
<223> OTHER INFORMATION: peptide sequence

<400> SEQUENCE: 32

Gly Gln Thr Ala Leu His Ile Ala Ile Glu Arg
1               5                   10

<210> SEQ ID NO 33
<211> LENGTH: 26
<212> TYPE: PRT
<213> ORGANISM: Artificial Sequence
<220> FEATURE:
<223> OTHER INFORMATION: peptide sequence

<400> SEQUENCE: 33

Asn Met Ala Leu Val Thr Leu Leu Val Glu Asn Gly Ala Asp Val Gln
1               5                   10                  15

Ala Ala Ala His Gly Asp Phe Phe Lys Lys
            20                  25

<210> SEQ ID NO 34
<211> LENGTH: 15
<212> TYPE: PRT
<213> ORGANISM: Artificial Sequence
<220> FEATURE:
<223> OTHER INFORMATION: peptide sequence

<400> SEQUENCE: 34

Phe Leu Leu Gln Asn Ser Trp Gln Thr Ala Asp Ile Ser Ala Arg
1               5                   10                  15

<210> SEQ ID NO 35
<211> LENGTH: 23
<212> TYPE: PRT
<213> ORGANISM: Artificial Sequence
<220> FEATURE:
<223> OTHER INFORMATION: peptide sequence

<400> SEQUENCE: 35

Asp Ser Val Gly Asn Thr Val Leu His Ala Leu Val Glu Val Ala Asp
1               5                   10                  15

Asn Thr Ala Asp Asn Thr Lys
            20

<210> SEQ ID NO 36
<211> LENGTH: 13
<212> TYPE: PRT
<213> ORGANISM: Artificial Sequence
<220> FEATURE:
<223> OTHER INFORMATION: peptide sequence

<400> SEQUENCE: 36

Leu His Pro Thr Leu Lys Leu Glu Glu Leu Thr Asn Lys
1               5                   10

<210> SEQ ID NO 37

```
<211> LENGTH: 14
<212> TYPE: PRT
<213> ORGANISM: Artificial Sequence
<220> FEATURE:
<223> OTHER INFORMATION: peptide sequence

<400> SEQUENCE: 37

Lys Gly Met Thr Pro Leu Ala Leu Ala Ala Gly Thr Gly Lys
1               5                   10

<210> SEQ ID NO 38
<211> LENGTH: 13
<212> TYPE: PRT
<213> ORGANISM: Artificial Sequence
<220> FEATURE:
<223> OTHER INFORMATION: peptide sequence

<400> SEQUENCE: 38

Gly Met Thr Pro Leu Ala Leu Ala Ala Gly Thr Gly Lys
1               5                   10

<210> SEQ ID NO 39
<211> LENGTH: 10
<212> TYPE: PRT
<213> ORGANISM: Artificial Sequence
<220> FEATURE:
<223> OTHER INFORMATION: peptide sequence

<400> SEQUENCE: 39

Ile Gly Val Leu Ala Tyr Ile Leu Gln Arg
1               5                   10

<210> SEQ ID NO 40
<211> LENGTH: 9
<212> TYPE: PRT
<213> ORGANISM: Artificial Sequence
<220> FEATURE:
<223> OTHER INFORMATION: peptide sequence

<400> SEQUENCE: 40

Ala Ile Thr Ile Leu Asp Thr Glu Lys
1               5

<210> SEQ ID NO 41
<211> LENGTH: 7
<212> TYPE: PRT
<213> ORGANISM: Artificial Sequence
<220> FEATURE:
<223> OTHER INFORMATION: peptide sequence

<400> SEQUENCE: 41

Thr Leu Ser Phe Ser Leu Arg
1               5

<210> SEQ ID NO 42
<211> LENGTH: 9
<212> TYPE: PRT
<213> ORGANISM: Artificial Sequence
<220> FEATURE:
<223> OTHER INFORMATION: peptide sequence

<400> SEQUENCE: 42

Asn Phe Ala Leu Val Pro Leu Leu Arg
1               5

<210> SEQ ID NO 43
<211> LENGTH: 18
```

```
<212> TYPE: PRT
<213> ORGANISM: Artificial Sequence
<220> FEATURE:
<223> OTHER INFORMATION: peptide sequence

<400> SEQUENCE: 43

Glu Ala Ser Ala Arg Asp Arg Gln Ser Ala Gln Pro Glu Glu Val Tyr
1               5                   10                  15

Leu Arg

<210> SEQ ID NO 44
<211> LENGTH: 13
<212> TYPE: PRT
<213> ORGANISM: Artificial Sequence
<220> FEATURE:
<223> OTHER INFORMATION: peptide sequence

<400> SEQUENCE: 44

Asp Arg Gln Ser Ala Gln Pro Glu Glu Val Tyr Leu Arg
1               5                   10

<210> SEQ ID NO 45
<211> LENGTH: 11
<212> TYPE: PRT
<213> ORGANISM: Artificial Sequence
<220> FEATURE:
<223> OTHER INFORMATION: peptide sequence

<400> SEQUENCE: 45

Gln Ser Ala Gln Pro Glu Glu Val Tyr Leu Arg
1               5                   10

<210> SEQ ID NO 46
<211> LENGTH: 15
<212> TYPE: PRT
<213> ORGANISM: Artificial Sequence
<220> FEATURE:
<223> OTHER INFORMATION: peptide sequence

<400> SEQUENCE: 46

Gln Phe Ser Gly Ser Leu Lys Pro Glu Asp Ala Glu Val Phe Lys
1               5                   10                  15

<210> SEQ ID NO 47
<211> LENGTH: 23
<212> TYPE: PRT
<213> ORGANISM: Artificial Sequence
<220> FEATURE:
<223> OTHER INFORMATION: peptide sequence

<400> SEQUENCE: 47

Gln Phe Ser Gly Ser Leu Lys Pro Glu Asp Ala Glu Val Phe Lys Ser
1               5                   10                  15

Pro Ala Ala Ser Gly Glu Lys
            20

<210> SEQ ID NO 48
<211> LENGTH: 11
<212> TYPE: PRT
<213> ORGANISM: Artificial Sequence
<220> FEATURE:
<223> OTHER INFORMATION: peptide sequence

<400> SEQUENCE: 48

Asp Gly Pro Thr Gly Ala Arg Leu Leu Ser Gln
1               5                   10
```

<210> SEQ ID NO 49
<211> LENGTH: 14
<212> TYPE: PRT
<213> ORGANISM: Artificial Sequence
<220> FEATURE:
<223> OTHER INFORMATION: peptide sequence

<400> SEQUENCE: 49

Asp Ser Val Ala Ala Ser Thr Glu Lys Thr Leu Arg Leu Tyr
1               5                   10

<210> SEQ ID NO 50
<211> LENGTH: 17
<212> TYPE: PRT
<213> ORGANISM: Artificial Sequence
<220> FEATURE:
<223> OTHER INFORMATION: peptide sequence

<400> SEQUENCE: 50

Asp Gly Gln Asn Thr Thr Ile Pro Leu Leu Leu Glu Ile Ala Arg Gln
1               5                   10                  15

Thr

<210> SEQ ID NO 51
<211> LENGTH: 12
<212> TYPE: PRT
<213> ORGANISM: Artificial Sequence
<220> FEATURE:
<223> OTHER INFORMATION: peptide sequence

<400> SEQUENCE: 51

Asp Ser Leu Lys Glu Leu Val Asn Ala Ser Tyr Thr
1               5                   10

<210> SEQ ID NO 52
<211> LENGTH: 15
<212> TYPE: PRT
<213> ORGANISM: Artificial Sequence
<220> FEATURE:
<223> OTHER INFORMATION: peptide sequence

<400> SEQUENCE: 52

Asp Ser Val Gly Asn Thr Val Leu His Ala Leu Val Glu Val Ala
1               5                   10                  15

<210> SEQ ID NO 53
<211> LENGTH: 14
<212> TYPE: PRT
<213> ORGANISM: Artificial Sequence
<220> FEATURE:
<223> OTHER INFORMATION: peptide sequence

<400> SEQUENCE: 53

Asp Ala Glu Val Phe Lys Ser Pro Ala Ala Ser Gly Glu Lys
1               5                   10

<210> SEQ ID NO 54
<211> LENGTH: 14
<212> TYPE: PRT
<213> ORGANISM: Artificial Sequence
<220> FEATURE:
<223> OTHER INFORMATION: peptide sequence

<400> SEQUENCE: 54

Leu Ser Gln Asp Ser Val Ala Ala Ser Thr Glu Lys Thr Leu

```
1               5                   10
```

<210> SEQ ID NO 55
<211> LENGTH: 13
<212> TYPE: PRT
<213> ORGANISM: Artificial Sequence
<220> FEATURE:
<223> OTHER INFORMATION: peptide sequence

<400> SEQUENCE: 55

```
Ser Gln Asp Ser Val Ala Ala Ser Thr Glu Lys Thr Leu
1               5                   10
```

<210> SEQ ID NO 56
<211> LENGTH: 16
<212> TYPE: PRT
<213> ORGANISM: Artificial Sequence
<220> FEATURE:
<223> OTHER INFORMATION: peptide sequence

<400> SEQUENCE: 56

```
Ser Gln Asp Ser Val Ala Ala Ser Thr Glu Lys Thr Leu Arg Leu Tyr
1               5                   10                  15
```

<210> SEQ ID NO 57
<211> LENGTH: 12
<212> TYPE: PRT
<213> ORGANISM: Artificial Sequence
<220> FEATURE:
<223> OTHER INFORMATION: peptide sequence

<400> SEQUENCE: 57

```
Asn Leu His Asp Gly Gln Asn Thr Thr Ile Pro Leu
1               5                   10
```

<210> SEQ ID NO 58
<211> LENGTH: 17
<212> TYPE: PRT
<213> ORGANISM: Artificial Sequence
<220> FEATURE:
<223> OTHER INFORMATION: peptide sequence

<400> SEQUENCE: 58

```
Leu Val Glu Asn Gly Ala Asp Val Gln Ala Ala Ala His Gly Asp Phe
1               5                   10                  15

Phe
```

<210> SEQ ID NO 59
<211> LENGTH: 16
<212> TYPE: PRT
<213> ORGANISM: Artificial Sequence
<220> FEATURE:
<223> OTHER INFORMATION: peptide sequence

<400> SEQUENCE: 59

```
Gln Thr Ala Asp Ile Ser Ala Arg Asp Ser Val Gly Asn Thr Val Leu
1               5                   10                  15
```

<210> SEQ ID NO 60
<211> LENGTH: 16
<212> TYPE: PRT
<213> ORGANISM: Artificial Sequence
<220> FEATURE:
<223> OTHER INFORMATION: peptide sequence

<400> SEQUENCE: 60

His Ala Leu Val Glu Val Ala Asp Asn Thr Ala Asp Asn Thr Lys Phe
1               5                   10                  15

<210> SEQ ID NO 61
<211> LENGTH: 12
<212> TYPE: PRT
<213> ORGANISM: Artificial Sequence
<220> FEATURE:
<223> OTHER INFORMATION: peptide sequence

<400> SEQUENCE: 61

Ala Ala Gly Thr Gly Lys Ile Gly Val Leu Ala Tyr
1               5                   10

<210> SEQ ID NO 62
<211> LENGTH: 12
<212> TYPE: PRT
<213> ORGANISM: Artificial Sequence
<220> FEATURE:
<223> OTHER INFORMATION: peptide sequence

<400> SEQUENCE: 62

Ser Gly Ser Leu Lys Pro Glu Asp Ala Glu Val Phe
1               5                   10

<210> SEQ ID NO 63
<211> LENGTH: 10
<212> TYPE: PRT
<213> ORGANISM: Artificial Sequence
<220> FEATURE:
<223> OTHER INFORMATION: peptide sequence

<400> SEQUENCE: 63

Phe Gly Lys Gly Asp Ser Glu Glu Ala Phe
1               5                   10

<210> SEQ ID NO 64
<211> LENGTH: 11
<212> TYPE: PRT
<213> ORGANISM: Artificial Sequence
<220> FEATURE:
<223> OTHER INFORMATION: peptide sequence

<400> SEQUENCE: 64

His Asp Gly Gln Asn Thr Thr Ile Pro Leu Leu
1               5                   10

<210> SEQ ID NO 65
<211> LENGTH: 16
<212> TYPE: PRT
<213> ORGANISM: Artificial Sequence
<220> FEATURE:
<223> OTHER INFORMATION: peptide sequence

<400> SEQUENCE: 65

Leu Val Glu Asn Gly Ala Asp Val Gln Ala Ala Ala His Gly Asp Phe
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: peptide sequence

<400> SEQUENCE: 66

Val Glu Asn Gly Ala Asp Val Gln Ala Ala Ala His Gly Asp Phe

```
                1               5                  10                 15
```

<210> SEQ ID NO 67
<211> LENGTH: 15
<212> TYPE: PRT
<213> ORGANISM: Artificial Sequence
<220> FEATURE:
<223> OTHER INFORMATION: peptide sequence

<400> SEQUENCE: 67

```
Val Glu Asn Gly Ala Asp Val Gln Ala Ala Ala His Gly Asp Phe
1               5                  10                 15
```

<210> SEQ ID NO 68
<211> LENGTH: 16
<212> TYPE: PRT
<213> ORGANISM: Artificial Sequence
<220> FEATURE:
<223> OTHER INFORMATION: peptide sequence

<400> SEQUENCE: 68

```
His Ala Leu Val Glu Val Ala Asp Asn Thr Ala Asp Asn Thr Lys Phe
1               5                  10                 15
```

<210> SEQ ID NO 69
<211> LENGTH: 13
<212> TYPE: PRT
<213> ORGANISM: Artificial Sequence
<220> FEATURE:
<223> OTHER INFORMATION: peptide sequence

<400> SEQUENCE: 69

```
Val Glu Val Ala Asp Asn Thr Ala Asp Asn Thr Lys Phe
1               5                  10
```

<210> SEQ ID NO 70
<211> LENGTH: 17
<212> TYPE: PRT
<213> ORGANISM: Artificial Sequence
<220> FEATURE:
<223> OTHER INFORMATION: peptide sequence

<400> SEQUENCE: 70

```
Glu Val Ile Ala Tyr Ser Ser Ser Glu Thr Pro Asn Arg His Asp Met
1               5                  10                 15

Leu
```

<210> SEQ ID NO 71
<211> LENGTH: 17
<212> TYPE: PRT
<213> ORGANISM: Artificial Sequence
<220> FEATURE:
<223> OTHER INFORMATION: peptide sequence

<400> SEQUENCE: 71

```
Val Ser Pro Val Ile Thr Ile Gln Arg Pro Gly Asp Gly Pro Thr Gly
1               5                  10                 15

Ala
```

<210> SEQ ID NO 72
<211> LENGTH: 12
<212> TYPE: PRT
<213> ORGANISM: Artificial Sequence
<220> FEATURE:
<223> OTHER INFORMATION: peptide sequence

```
<400> SEQUENCE: 72

Ile Gln Arg Pro Gly Asp Gly Pro Thr Gly Ala Arg
1               5                   10

<210> SEQ ID NO 73
<211> LENGTH: 12
<212> TYPE: PRT
<213> ORGANISM: Artificial Sequence
<220> FEATURE:
<223> OTHER INFORMATION: peptide sequence

<400> SEQUENCE: 73

Arg Pro Gly Asp Gly Pro Thr Gly Ala Arg Leu Leu
1               5                   10

<210> SEQ ID NO 74
<211> LENGTH: 15
<212> TYPE: PRT
<213> ORGANISM: Artificial Sequence
<220> FEATURE:
<223> OTHER INFORMATION: peptide sequence

<400> SEQUENCE: 74

Leu Asn Leu His Asp Gly Gln Asn Thr Thr Ile Pro Leu Leu Leu
1               5                   10                  15

<210> SEQ ID NO 75
<211> LENGTH: 8
<212> TYPE: PRT
<213> ORGANISM: Artificial Sequence
<220> FEATURE:
<223> OTHER INFORMATION: peptide sequence

<400> SEQUENCE: 75

Asp Thr Glu Lys Ser Phe Leu Lys
1               5

<210> SEQ ID NO 76
<211> LENGTH: 11
<212> TYPE: PRT
<213> ORGANISM: Artificial Sequence
<220> FEATURE:
<223> OTHER INFORMATION: peptide sequence

<400> SEQUENCE: 76

Glu Asp Pro Gly Asn Cys Glu Gly Val Lys Arg
1               5                   10

<210> SEQ ID NO 77
<211> LENGTH: 12
<212> TYPE: PRT
<213> ORGANISM: Artificial Sequence
<220> FEATURE:
<223> OTHER INFORMATION: peptide sequence

<400> SEQUENCE: 77

Glu Asp Pro Gly Asn Cys Glu Gly Val Lys Arg Thr
1               5                   10

<210> SEQ ID NO 78
<211> LENGTH: 13
<212> TYPE: PRT
<213> ORGANISM: Artificial Sequence
<220> FEATURE:
<223> OTHER INFORMATION: peptide sequence

<400> SEQUENCE: 78
```

```
Glu Asp Pro Gly Asn Cys Glu Gly Val Lys Arg Thr Leu
1               5                   10

<210> SEQ ID NO 79
<211> LENGTH: 16
<212> TYPE: PRT
<213> ORGANISM: Artificial Sequence
<220> FEATURE:
<223> OTHER INFORMATION: peptide sequence

<400> SEQUENCE: 79

Ser Ala Arg Asp Arg Gln Ser Ala Gln Pro Glu Glu Val Tyr Leu Arg
1               5                   10                  15

<210> SEQ ID NO 80
<211> LENGTH: 13
<212> TYPE: PRT
<213> ORGANISM: Artificial Sequence
<220> FEATURE:
<223> OTHER INFORMATION: peptide sequence

<400> SEQUENCE: 80

Asp Arg Gln Ser Ala Gln Pro Glu Glu Val Tyr Leu Arg
1               5                   10

<210> SEQ ID NO 81
<211> LENGTH: 11
<212> TYPE: PRT
<213> ORGANISM: Artificial Sequence
<220> FEATURE:
<223> OTHER INFORMATION: peptide sequence

<400> SEQUENCE: 81

Gln Ser Ala Gln Pro Glu Glu Val Tyr Leu Arg
1               5                   10
```